United States Patent
Wood et al.

(10) Patent No.: US 12,268,749 B2
(45) Date of Patent: Apr. 8, 2025

(54) CELL-PENETRATING PEPTIDES

(71) Applicants: Oxford University Innovation Limited, Oxford (GB); United Kingdom Research and Innovation, Swindon (GB)

(72) Inventors: Matthew Wood, Oxford (GB); Raquel Manzano, Zargoza (ES); Caroline Godfrey, Oxford (GB); Graham McClorey, Oxford (GB); Richard Raz, London (GB); Michael Gait, Cambridge (GB); Andrey Arzumanov, Cambridge (GB); Liz O'Donovan, Ballyanly (IE); Gareth Hazell, Oxford (GB); Ashling Holland, Oxford (GB); Miguel Varela, Oxford (GB)

(73) Assignees: Oxford University Innovation Limited, Oxford (GB); United Kingdom Research and Innovation, Swindon (GB)

( * ) Notice: Subject to any disclaimer, the term of this patent is extended or adjusted under 35 U.S.C. 154(b) by 854 days.

(21) Appl. No.: 17/266,939

(22) PCT Filed: Aug. 9, 2019

(86) PCT No.: PCT/GB2019/052247
§ 371 (c)(1),
(2) Date: Feb. 8, 2021

(87) PCT Pub. No.: WO2020/030927
PCT Pub. Date: Feb. 13, 2020

(65) Prior Publication Data
US 2021/0299263 A1 Sep. 30, 2021

(30) Foreign Application Priority Data
Aug. 9, 2018 (GB) ................................ 1812972

(51) Int. Cl.
| | |
|---|---|
| A61K 47/64 | (2017.01) |
| C07K 7/08 | (2006.01) |
| C07K 14/00 | (2006.01) |
| C12N 15/113 | (2010.01) |

(52) U.S. Cl.
CPC .............. *A61K 47/645* (2017.08); *C07K 7/08* (2013.01); *C07K 14/00* (2013.01); *C12N 15/113* (2013.01); *C07K 2319/10* (2013.01); *C12N 2310/11* (2013.01); *C12N 2310/3513* (2013.01); *C12N 2320/32* (2013.01)

(58) Field of Classification Search
CPC ........ A61K 47/645; C07K 7/08; C07K 14/00; C07K 2319/10; C12N 15/113; C12N 2310/11; C12N 2310/3513
See application file for complete search history.

(56) References Cited

U.S. PATENT DOCUMENTS

| | | |
|---|---|---|
| 7,838,657 B2 | 11/2010 | Singh et al. |
| 8,324,371 B2 | 12/2012 | Popplewell et al. |
| 8,361,979 B2 | 1/2013 | Aartsma-Rus et al. |
| 8,575,305 B2 | 11/2013 | Gait et al. |
| 8,637,483 B2 | 1/2014 | Wilton et al. |
| 8,741,863 B2 | 6/2014 | Moulton et al. |
| 8,835,402 B2 | 9/2014 | Kole et al. |
| 9,018,368 B2 | 4/2015 | Wilton et al. |
| 9,079,934 B2 | 7/2015 | Watanabe et al. |
| 9,161,948 B2 | 10/2015 | Hanson |
| 9,238,052 B2 | 1/2016 | Kameyama et al. |
| 9,302,014 B2 | 4/2016 | Gait et al. |
| 9,447,417 B2 | 9/2016 | Sazani et al. |
| 9,528,109 B2 | 12/2016 | De Kimpe et al. |
| 9,582,637 B1 | 2/2017 | Fernandez et al. |
| 9,926,557 B2 | 3/2018 | De Kimpe et al. |
| 10,160,969 B2 | 12/2018 | Meena et al. |
| 10,385,092 B2 | 8/2019 | Watanabe et al. |
| 10,781,450 B2 | 9/2020 | Wilton et al. |
| 10,876,114 B2 | 12/2020 | Van Deutekom |
| 2008/0306001 A1 | 12/2008 | Liik et al. |
| 2009/0099066 A1 | 4/2009 | Moulton et al. |
| 2010/0016215 A1 | 1/2010 | Moulton et al. |
| 2011/0105403 A1 | 5/2011 | Gait et al. |
| 2011/0269665 A1 | 11/2011 | Kole |
| 2012/0289457 A1 | 11/2012 | Gunnar |
| 2014/0051646 A1 | 2/2014 | Gait et al. |
| 2014/0315977 A1 | 10/2014 | Bestwick et al. |

(Continued)

FOREIGN PATENT DOCUMENTS

| | | |
|---|---|---|
| CN | 103619356 A | 3/2014 |
| CN | 103998458 A | 8/2014 |

(Continued)

OTHER PUBLICATIONS

"Peptide Design," ThermoFisher Scientific, <https://www.thermofisher.com/us/en/home/life-science/protein-biology/protein-biology-learning-center/protein-biology-resource-library/pierce-protein-methods/peptide-design.html>, retrieved on Oct. 18, 2022 (9 pages).

Amantana et al., "Pharmacokinetics, biodistribution, stability and toxicity of a cell-penetrating peptide-morpholino oligomer conjugate," Bioconjug Chem. 18(4): 1325-31 (Jun. 2007).

Bahal et al., "In vivo correction of anaemia in beta-thalassemic mice by gammaPNA-mediated gene editinq with nanoparticle delivery," Nature Communications, 7:13304 (2016) (14 pages).

Borrelli et al., "Cell Penetrating Peptides as Molecular Carriers for Anti-Cancer Agents," Molecules. 23(2):295 (Jan. 2018) (28 pages).

(Continued)

*Primary Examiner* — Li N Komatsu
(74) *Attorney, Agent, or Firm* — Clark & Elbing LLP

(57) ABSTRACT

The present invention relates to peptides, in particular cell-penetrating peptides, and to conjugates of such cell-penetrating peptides with a therapeutic molecule. The present invention further relates to use of such peptides or conjugates in methods of treatment or as a medicament, especially in the treatment of genetic disorders and in particular muscular dystrophies such as Duchenne muscular dystrophy.

22 Claims, 19 Drawing Sheets
Specification includes a Sequence Listing.

(56) References Cited

U.S. PATENT DOCUMENTS

| | | |
|---|---|---|
| 2014/0342992 A1 | 11/2014 | Gait et al. |
| 2015/0183827 A1 | 7/2015 | Milletti |
| 2015/0238627 A1 | 8/2015 | Leger et al. |
| 2016/0237426 A1 | 8/2016 | Hanson |
| 2019/0177723 A1 | 6/2019 | Dickson |
| 2019/0241892 A1 | 8/2019 | Van Deutekom |
| 2020/0131231 A1 | 4/2020 | Wood et al. |
| 2021/0299264 A1 | 9/2021 | Wood et al. |
| 2021/0388353 A1 | 12/2021 | Popplewell et al. |
| 2022/0041662 A1 | 2/2022 | Wood et al. |
| 2022/0090066 A1 | 3/2022 | Wood et al. |
| 2022/0125934 A1 | 4/2022 | Raz et al. |
| 2022/0275372 A1 | 9/2022 | Wood et al. |
| 2022/0288218 A1 | 9/2022 | Yokota et al. |
| 2024/0189434 A1 | 6/2024 | Godfrey et al. |
| 2024/0200062 A1 | 6/2024 | Godfrey et al. |

FOREIGN PATENT DOCUMENTS

| | | |
|---|---|---|
| EP | 2394665 A1 | 12/2011 |
| EP | 3034074 A1 | 6/2016 |
| EP | 2344637 B2 | 2/2018 |
| EP | 3443976 A1 | 2/2019 |
| EP | 3031920 B1 | 8/2019 |
| GB | 2563964 A | 1/2019 |
| JP | 2006-514602 A | 5/2006 |
| JP | 2007-509978 A | 4/2007 |
| JP | 2009-544749 A | 12/2009 |
| JP | 2018-532695 A | 11/2018 |
| RU | 2556800 C2 | 7/2015 |
| WO | WO-1999/67284 A2 | 12/1999 |
| WO | WO-2000/39139 A1 | 7/2000 |
| WO | WO-2003/106491 A2 | 12/2003 |
| WO | WO-2004/097017 A2 | 11/2004 |
| WO | WO-2005/042539 A1 | 5/2005 |
| WO | WO-2006/000057 A1 | 1/2006 |
| WO | WO-2008/012365 A2 | 1/2008 |
| WO | WO-2008/109105 A2 | 9/2008 |
| WO | WO-2009/005793 A2 | 1/2009 |
| WO | 2009147368 A1 | 12/2009 |
| WO | WO-2009/144481 A2 | 12/2009 |
| WO | WO-2011/157713 A2 | 12/2011 |
| WO | WO-2012012443 A2 | 1/2012 |
| WO | WO-2012/072088 A1 | 6/2012 |
| WO | WO-2012/090150 A2 | 7/2012 |
| WO | WO-2012/150960 A1 | 11/2012 |
| WO | 2013030569 A2 | 3/2013 |
| WO | WO-2013/040429 A1 | 3/2013 |
| WO | WO-2014/001229 A2 | 1/2014 |
| WO | WO-2014/041505 A1 | 3/2014 |
| WO | WO-2014/043544 A1 | 3/2014 |
| WO | WO-2014/052276 A1 | 4/2014 |
| WO | 2015022504 A2 | 2/2015 |
| WO | WO-2015/113922 A1 | 8/2015 |
| WO | WO-2015/155753 A2 | 10/2015 |
| WO | WO-2015/161255 A1 | 10/2015 |
| WO | WO-2016/028187 A1 | 2/2016 |
| WO | WO-2016/154328 A2 | 9/2016 |
| WO | WO-2017/027848 A1 | 2/2017 |
| WO | WO-2018/017190 A2 | 1/2018 |
| WO | WO-2018/053316 A1 | 3/2018 |
| WO | WO-2019/067975 A1 | 4/2019 |
| WO | WO-2019/067979 A1 | 4/2019 |
| WO | WO-2019/067981 A1 | 4/2019 |
| WO | WO-2020/030927 A1 | 2/2020 |
| WO | WO-2020/030928 A1 | 2/2020 |
| WO | WO-2020/115494 A1 | 6/2020 |
| WO | WO-2020/214763 A1 | 10/2020 |
| WO | WO-2020/257489 A1 | 12/2020 |
| WO | WO-2021/003573 A1 | 1/2021 |
| WO | WO-2021/028666 A1 | 2/2021 |
| WO | WO-2022/172019 A1 | 8/2022 |
| WO | WO-2022/192749 A2 | 9/2022 |
| WO | WO-2022/192754 A2 | 9/2022 |

OTHER PUBLICATIONS

Chan et al., "The complexity of antisense transcription revealed by the study of developing male germ cells," Genomics. 87(6):681-92 (2006).

Dutot et al., "Glycosylated cell penetrating peptides and their conjugates to a proapoptotic peptide: Preparation by click chemistry and cell viability studies," Journal of Chemical Biology, 3(2):51-65 (2010).

Egleton et al., "Improved bioavailability to the brain of glycosylated Met-enkephalin analogs," Brain Research, 881 (1 ):37-46 (2000).

Futaki et al., "Translocation of branched chain arginine peptides through cell membranes: Flexibility in the spatial disposition of positive charges in membrane-permeable peptides," Biochemistry, 41(25):7926-7930 (2002).

González-Barriga et al., "Design and analysis of effects of triplet repeat oligonucleotides in cell models for myotonic dystrophy," Mol Ther Nucleic Acids. 2(3): 1-12 (Mar. 2013).

Hammond et al., "Systemic peptide-mediated oligonucleotide therapy improves long-term survival in spinal muscular atrophy," PNAS, 113(39):10962-10967 (2016).

Ibraheem et al., "Gene therapy and DNA delivery systems," Int J Pharm. 459(1-2): 70-83 (Jan. 2014).

Jahn et al., "How to systematically evaluate immunogenicity of therapeutic proteins—regulatory considerations," N Biotechnol. 25(5):280-6 (2009).

Kalafatovic et al., "Cell-Penetrating Peptides: Design Strategies beyond Primary Structure and Amphipathicity," Molecules. 22(11): 1929 (2017) (38 pages).

Kontermann et al., "Bispecific antibodies," Drug Discov Today. 20(7):838-47 (Jul. 2015) (12 pages).

Kuznetsova, "Brackets in text of a legal document as a linguistic and cognitive phenomenon," Vestnik MGOU. N3:37-43 (2015), Abstract only.

Lapidot et al., "Genome-wide natural antisense transcription: coupling its regulation to its different regulatory mechanisms," EMBO Rep. 7(12):1216-22 (2006).

Lehto et al., "Peptides for nucleic acid delivery," Adv Drug Deliv Rev. 106(Pt A):172-182 (2016).

Lécorché et al., "Cellular uptake and biophysical properties of galactose and/or tryptophan containing cell-penetrating peptides," Biochimica et Biophysica Acta, 1818(3):448-457 (2012).

McClorey et al., "Cell-Penetrating Peptides to Enhance Delivery of Oligonucleotide-Based Therapeutics," Biomedicines. 6(2):51. doi: 10.3390/biomedicines6020051 (May 2018) (15 pages).

Nan et al., "Antisense Phosphorodiamidate Morpholino Oligomers as Novel Antiviral Compounds," Front Microbiol. 9: 1-15 (Apr. 2018).

Osman et al., "Morpholino antisense oligonucleotides targeting intronic repressor Element1 improve phenotype in SMA mouse models," Human Molecular Genetics, 23(18):4832-4845 (2014).

Pinto et al., "Impeding Transcription of Expanded Microsatellite Repeats by Deactivated Cas9," Mol Cell. 68(3): 479-490 (Nov. 2017).

Rothbard et al., "Arginine-rich molecular transporters for drug delivery: Role of backbone spacina in cellular uptake," Journal of Medicinal Chemistry, 45(17):3612-8 (2002).

Rydberg et al., "Effects of tryptophan content and backbone spacing on the uptake efficiency of cell-penetrating peptides," Biophysical Journal, Board B253. 102(3):487a (2012).

Shabanpoor et al., "Bi-specific splice-switching PMO oligonucleotides conjugated via a single peptide active in a mouse model of Duchenne muscular dystrophy," Nucleic Acids Res. 43(1):29-39 (2015).

Shabanpoor et al., "Development of a general methodology for labelling peptide-morpholino oligonucleotide conjugates using alkyne-azide click chemistry," Chem Commun (Camb). 49(87):10260-2 (2013) (9 pages).

Shabanpoor et al., "Identification of a peptide for systemic brain delivery of a morpholino oligonucleotide in mouse models of spinal muscular atrophy," Nucleic Acid Therapeutics. 27(3):130-143 (2017) (15 pages).

(56) References Cited

OTHER PUBLICATIONS

Shen et al., "Single variable domain-IgG fusion. A novel recombinant approach to Fc domain-containing bispecific antibodies," J Biol Chem. 281(16):10706-14 (2006).

Swenson et al., "Chemical modifications of antisense morpholino oligomers enhance their efficacy against Ebola virus infection," Antimicrob Agents Chemother. 53(5): 2089-99 (May 2015).

Torres et al., "The immunoglobulin constant region contributes to affinity and specificity," Trends Immunol. 29(2):91-7 (2008).

Wermuth et al., "Glossary of terms used in medicinal chemistry," Pure & Appl. Chem. 70(5):1129-43 (1998).

Witt et al., "Peptide drug modifications to enhance bioavailability and blood-brain barrier permeability," Peptides. 22(12):2329-2343 (2001).

Wu et al., "Long-term rescue of dystrophin expression and improvement in muscle pathology and function in dystrophic mdx mice by peptide-conjugated morpholino," Am J Pathol. 181(2): 392-400. (Aug. 2012).

Yin et al., "Pip5 Transduction Peptides Direct High Efficiency Oligonucleotide-mediated Dystrophin Exon Skipping in Heart and Phenotypic Correction in mdx Mice," Molecular Therapy, 19(7):1295-1303 (2011).

Zhou et al., "A Novel Morpholino Oligomer Targeting ISS-N1 Improves Rescue of Severe Spinal Muscular Atrophy Transgenic Mice," Human Gene Therapy. 24(3):331-342 (2013).

Zorko et al., "Cell-penetrating peptides: mechanism and kinetics of cargo delivery," Adv Drug Deliv Rev. 57(4):529-45 (2005).

Riháček et al. [New Indings in Methotrexate Pharmacology—Diagnostic Possibilities and Impact on Clinical Care] Klin Onkol. 2015;28(3):163-70. doi: 10.14735/amko2015163. (abstract only).

Alaybeyoglu et al., "Insights into membrane translocation of the cell-penetrating peptide pVEC from molecular dynamics calculations." Journal of Biomolecular Structure and Dynamics. 34(11): 2387-2398 (2016) (14 pages).

Deuss et al., "Parallel synthesis and splicing redirection activity of cell-penetrating peptide conjugate libraries of a PNA cargo." Organic & Biomolecular Chemistry. 11:7621-7630 (2013) (10 pages).

Godfrey et al., "How much dystrophin is enough: the physiological consequences of different levels of dystrophin in the mdx mouse." Human Molecular Genetics. 24(15):4225-4237 (May 1, 2015) (13 pages).

Lehto et al., "Cellular trafficking determines the exon skipping activity of Pip6a-PMO in mdx skeletal and cardiac muscle cells." Nucleic Acids Res. 42(5):3207-3217 (Dec. 23, 2013) (11 pages).

Marks et al., "Spontaneous Membrane-Translocating Peptides by Orthogonal High-Throughput Screening." Journal of the American Chemical Society. 133: 8995-9004 (May 5, 2011) (10 pages).

Wu et al., "Cell-penetrating peptides as transporters for morpholino oligomers: effects of amino acid composition on intracellular delivery and cytotoxicity," Nucleic Acids Research, vol. 35, No. 15, Jan. 1, 2007, pp. 5182-5191.

Rydberg et al., "Effects of Tryptophan Content and Backbone Spacing on the Uptake Efficiency of Cell-Penetrating Peptides," Biochemistry, vol. 51, No. 27, Jun. 28, 2012, pp. 5531-5539.

Betts et al., "Pip6-PMO, A New Generation of Peptide-oligonucleotide Conjugates With Improved Cardiac Exon Skipping Activity for DMD Treatment," Molecular Therapy—Nucleic Acids, vol. 1, No. 8, Aug. 1, 2012, p. e38.

Ablan, et al., "Charge Distribution fine-Tunes the Translocation of [alpha]-Helical Amphipathic Peptides across Membranes," Biophysical Journal, vol. 111, No. 8, Oct. 18, 2016, pp. 1738-1749.

Milletti, "Cell-penetrating peptides: classes, origin, and current landscape," Drug Discovery Today, vol. 17, No. 15-16, Aug. 1, 2012, pp. 850-860.

International Search Report and Written Opinion issued in PCT/GB2019/052247, mailed Oct. 31, 2019, 19 pages.

Dimachkie et al., "Distal myopathies," available in PMC Aug. 1, 2015, published in final edited form as: Neurol Clin. 32(3):817-42 (Aug. 2014) (Epub May 2014) (32 pages).

Haurum et al., "Presentation of Cytosolic Glycosylated Peptides by Human Class I Major Histocompatibility Complex Molecules In Vivo". Journal of Experimental Medicine. 190(1): 145-150 (Jul. 5, 1999) (6 pages).

Nikolenko et al., "Rehabilitation of children with progressive muscular dystrophy Duchenne," Russian Bulletin of Perinatology and Pediatrics. 4:28-31 (2014), Abstract only.

Office Action dated Jul. 12, 2024, issued in Russian Patent Application No. 2021105152 (English Translation) (6 pages).

CELL-PENETRATING PEPTIDES

SEQUENCE LISTING

The instant application contains a Sequence Listing which has been submitted electronically in ASCII format and is hereby incorporated by reference in its entirety. Said ASCII copy, created on Oct. 15, 2024, is named 51558-004002 Sequence_Listing_10_15_24_ST25 and is 45,809 bytes in size.

TECHNICAL FIELD

The present invention relates to peptides, in particular cell-penetrating peptides, and to conjugates of such cell-penetrating peptides with a therapeutic molecule. The present invention further relates to use of such peptides or conjugates in methods of treatment or as a medicament, especially in the treatment of genetic disorders and in particular muscular dystrophies such as Duchenne muscular dystrophy.

BACKGROUND

Nucleic acid drugs are genomic medicines with the potential to transform human healthcare. Research has indicated that such therapeutics could have applications across a broad range of disease areas including neuromuscular disease. The application of antisense oligonucleotide-based methods to modulate pre-mRNA splicing in the neuromuscular disease Duchenne muscular dystrophy (DMD) has placed this monogenic disorder at the forefront of advances in precision medicine.

However, therapeutic development of these promising antisense therapeutics has been hampered by insufficient cell-penetrance and poor distribution characteristics—a challenge that is further emphasised by the large volume and dispersed nature of the muscle tissue substrate in DMD.

DMD affects one in 3500 new born boys. This severe, X-linked recessive disease results from mutations in the DMD gene that encodes dystrophin protein. The disorder is characterised by progressive muscle degeneration and wasting, along with the emergence of respiratory failure and cardiac complications, ultimately leading to premature death. The majority of mutations underlying DMD are genomic out-of-frame deletions that induce a premature truncation in the open reading frame that results in the absence of the dystrophin protein.

Exon skipping therapy utilises splice switching antisense oligonucleotides (SSOs) to target specific regions of the DMD transcript, inducing the exclusion of individual exons, leading to the restoration of aberrant reading frames and resulting in the production of an internally deleted, yet partially functional, dystrophin protein. Despite the undoubted potential of antisense oligonucleotide exon skipping therapy for DMD, the successful application of this approach is currently limited by the relatively inefficient targeting of skeletal muscle, as well as the inadequate targeting of single-stranded oligonucleotides to other affected tissues such as the heart.

In September 2016 the Food and Drug Administration (FDA) granted accelerated approval for 'eteplirsen', a single-stranded oligonucleotide for modulating the splicing of exon 51. Although this heralded the first approved oligonucleotide that modulates splicing in the US, the levels of dystrophin restoration were disappointing with only approximately 1% of normal dystrophin levels. Comparisons with the allelic disorder Becker muscular dystrophy and experiments in the mdx mouse have indicated that homogenous sarcolemmal dystrophin expression of at least ~15% of wild-type is needed to protect muscle against exercise induced damage.

Therefore there is a strong and urgent need to improve the delivery of antisense oligonucleotides in order to provide a more effective therapy for devastating genetic diseases such as DMD.

The use of viruses as delivery vehicles has been suggested, however their use is limited due to the immunotoxicity of the viral coat protein and potential oncogenic effects. Alternatively, a range of non-viral delivery vectors have been developed, amongst which peptides have shown the most promise due to their small size, targeting specificity and ability of trans-capillary delivery of large bio-cargoes. Several peptides have been reported for their ability to permeate cells either alone or carrying a bio-cargo.

For several years, cell-penetrating peptides (CPPs) have been conjugated to SSOs (in particular charge neutral phosphorodiamidate morpholino oligomers (PMO) and peptide nucleic acids (PNA)) in order to enhance the cell delivery of such oligonucleotide analogues by effectively carrying them across cell membranes to reach their pre-mRNA target sites in the cell nucleus. It has been shown that PMO therapeutics conjugated to certain arginine-rich CPPs (known as P-PMOs or peptide-PMOs) can enhance dystrophin production in skeletal muscles following systemic administration in a mdx mouse model of DMD.

In particular, PNA/PMO internalization peptides (Pips) have been developed which are arginine-rich CPPs that are comprised of two arginine-rich sequences separated by a central short hydrophobic sequence. These 'Pip' peptides were designed to improve serum stability whilst maintaining a high level of exon skipping, initially by attachment to a PNA cargo. Further derivatives of these peptides were designed as conjugates of PMOs, which were shown to lead to body-wide skeletal muscle dystrophin production, and importantly also including the heart, following systemic administration in mice. Despite these peptides being efficacious, their therapeutic application has been hampered by their associated toxicity.

Alternative cell-penetrating peptides having a single arginine rich domain such as $R_6Gly$ (SEQ ID NO: 115) have also been produced. These CPPs have been used to produce peptide conjugates with reduced toxicities, but these conjugates exhibited low efficacy in comparison to the Pip peptides.

Accordingly, the currently available CPPs have not yet been demonstrated as suitable for use in human treatments for diseases such as DMD.

The challenge in the field of cell-penetrating peptide technology has been to de-couple efficacy and toxicity. The present inventors have now identified, synthesized and tested a number of improved CPPs having a particular structure according to the present invention which address at least this problem.

These peptides maintain good levels of efficacy in skeletal muscles when tested in vitro and in vivo with a cargo therapeutic molecule. Furthermore, these peptides demonstrate an improvement in efficacy compared with previously available CPPs when used in the same conjugate. At the same time, these peptides act effectively in vivo with reduced clinical signs following systemic injection and lower toxicity as observed through measurement of biochemical markers. Crucially, the present peptides are demonstrated to show a surprisingly reduced toxicity following similar systemic injection into mice when compared with previous CPPs. Accordingly, the peptides of the invention offer improved suitability for use as a therapy for humans than previously available peptides and can be used in therapeutic conjugates for safe and effective treatment of human subjects.

SUMMARY OF THE INVENTION

According to a first aspect of the present invention, there is provided a peptide having a total length of 40 amino acid residues or less, the peptide comprising:
  two or more cationic domains each comprising at least 4 amino acid residues; and
  one or more hydrophobic domains each comprising at least 3 amino acid residues;
wherein the peptide does not contain artificial amino acid residues.

According to a second aspect of the present invention, there is provided a conjugate comprising the peptide of the first aspect covalently linked to a therapeutic molecule.

According to a third aspect of the present invention, there is provided a conjugate comprising the peptide of the first aspect covalently linked to an imaging molecule.

According to a fourth aspect of the present invention, there is provided a pharmaceutical composition comprising the conjugate of the second aspect.

According to a fifth aspect of the present invention, there is provided a conjugate according to the second aspect for use as a medicament.

In one embodiment of the fifth aspect, there is provided a pharmaceutical composition according to the fourth aspect for use as a medicament.

According to a sixth aspect of the present invention, there is provided a method of treating a disease in a subject comprising administering the conjugate of the second aspect to the subject in a therapeutically effective amount.

In one embodiment of the sixth aspect, there is provided a method of treating a disease in a subject comprising administering the pharmaceutical composition according to the fourth aspect to the subject in a therapeutically effective amount.

According to a seventh aspect of the present invention, there is provided an isolated nucleic acid encoding the peptide of the first aspect or the conjugate of the second aspect or the conjugate of the third aspect.

According to an eighth aspect of the present invention, there is provided an expression vector comprising the nucleic acid sequence of the seventh aspect.

According to a ninth aspect of the present invention, there is provided a host cell comprising the expression vector of the eighth aspect.

DETAILED DESCRIPTION

The inventors have produced a series of peptides that are suitable for use as cell-penetrating peptides to deliver therapeutic molecules into cells.

Surprisingly, the inventors have discovered a group of peptides having at least two cationic domains and at least one hydrophobic domain of defined lengths without any artificial amino acids which, provide enhanced cell penetration into muscles, compared with currently available cell-penetrating peptides. This effect is observed when delivered as a conjugate with an antisense oligonucleotide therapeutic into cells, or when administered in vivo.

In the context of the disease DMD, enhanced cell penetration by peptides of the invention linked to a suitable therapeutic molecule can be shown by specific exon exclusion within the transcript. The directing of an antisense oligonucleotide to an appropriate sequence results in the forced skipping of an exon, the correction of the open reading frame and the restoration of an internally deleted, yet partially functional isoform of dystrophin.

The peptides of the present invention, when used as a conjugate with an antisense oligonucleotide therapeutic designed to target the dystrophin gene are shown herein to have high levels of exon exclusion and dystrophin protein restoration.

In particular, the conjugates comprising peptides of the invention show significantly increased cell penetration when compared with currently available peptides conjugated to the same antisense oligonucleotide therapeutic. This is demonstrated in the present invention by increased exon skipping in the dystrophin gene in various different muscle groups.

In vivo, the results described herein show levels exon skipping and functional dystrophin expression when using peptide conjugates of the invention approaching double the levels resulting from the use of the same antisense oligonucleotide therapeutic conjugated to a previously available cell-penetrating peptides.

This is a significant improvement in the efficacy of such peptide carriers to penetrate muscle cells where neuromuscular diseases take effect.

Without wishing to be bound by theory, the inventors believe that the removal of artificial amino acids such as 6-aminohexanoic acid residues typically used in cell-penetrating peptides and replacement by for example naturally occurring beta-alanine residues has the beneficial effect of reducing the overall toxicity and increasing the cell penetration of the peptides.

However, it was completely unanticipated that such a peptide structure that does not contain any artificial amino acid residues would increase the delivery properties of previously reported cell-penetrating peptides to transport a therapeutic molecule cargo, such as an oligonucleotide, into muscle. A peptide's effectiveness largely depends on its ability to be serum-stable for the required length of time for it to get into cells. It was expected that peptides formed without artificial amino acids would be too unstable and vulnerable to protease degradation in vivo to allow a sufficient amount to penetrate muscle cells and tissue and result in enhanced therapeutic effect. Contrary to this expectation, the inventors found that peptides having a particular structure as claimed are stable enough to enter cells and maintain good, even improved efficacy, yet have the advantage of a reduced toxicity profile due to lacking artificial amino acids.

It was unexpected that such transport would be increased so as to result in a therapeutic molecule such as an antisense oligonucleotide successfully increasing exon skipping and functional dystrophin protein production in various different muscles as demonstrated herein.

In addition, it was unexpected that such a peptide structure would significantly reduce toxicity of the cell-penetrating peptide when transporting a therapeutic cargo in vivo to the extent that human treatment with such a conjugate is viable. In vivo, the results described herein show a decrease in nephrotoxicity as determined by biochemical markers.

For the avoidance of doubt, and in order to clarify the way in which the present disclosure is to be interpreted, certain terms used in accordance with the present invention will now be defined further.

The invention includes any combination of the aspects and features described except where such a combination is clearly impermissible or expressly avoided.

The section headings used herein are for organisational purposes only and are not to be construed as limiting the subject matter described.

References to 'X' throughout denote any form of the artificial, synthetically produced amino acid aminohexanoic acid.

References to 'B' throughout denote the natural but non-genetically encoded amino acid beta-alanine.

References to 'Ac' throughout denote acetylation of the relevant peptide.

References to 'Hyp' throughout denote the natural but non-genetically encoded amino acid hydroxyproline.

References to other capital letters throughout denote the relevant genetically encoded amino acid residue in accordance with the accepted alphabetic amino acid code.

Artificial Amino Acids

The present invention relates to short cell-penetrating peptides that have a particular structure in which there are no artificial amino acid residues.

References to an 'artificial' amino acid or residue herein denotes any amino acid that does not occur in nature and includes synthetic amino acids, modified amino acids (such as those modified with sugars), non-natural amino acids, man-made amino acids, spacers, and non-peptide bonded spacers.

Synthetic amino acids may be those that are chemically synthesised by man.

For the avoidance of doubt, aminohexanoic acid (X) is an artificial amino acid in the context of the present invention. For the avoidance of doubt, beta-alanine (B) and hydroxyproline (Hyp) occur in nature and therefore are not artificial amino acids in the context of the present invention but are natural amino acids.

Artificial amino acids may include, for example, 6-aminohexanoic acid (X), tetrahydroisoquinoline-3-carboxylic acid (TIC), 1-(amino)cyclohexanecarboxylic acid (Cy), and 3-azetidine-carboxylic acid (Az), 11-aminoundecanoic acid.

Suitably, the peptide does not contain aminohexanoic acid residues. Suitably, the peptide does not contain any form of aminohexanoic acid residues. Suitably, the peptide does not contain 6-aminohexanoic acid residues.

Suitably, the peptide contains only natural amino acid residues, and therefore consists of natural amino acid residues.

Suitably, artificial amino acids such as 6-aminohexanoic acid that are typically used in cell-penetrating peptides are replaced by natural amino acids. Suitably the artificial amino acids such as 6-aminohexanoic acid that are typically used in cell-penetrating peptides are replaced by amino acids selected from beta-alanine, serine, proline, arginine and histidine or hydroxyproline.

In one embodiment, aminohexanoic acid is replaced by beta-alanine. Suitably, 6-aminohexanoic acid is replaced by beta-alanine In one embodiment, aminohexanoic acid is replaced by histidine. Suitably, 6-aminohexanoic acid is replaced by histidine.

In one embodiment, aminohexanoic acid is replaced by hydroxyproline. Suitably, 6-aminohexanoic acid is replaced by hydroxyproline.

Suitably, the artificial amino acids such as 6-aminohexanoic acid that are typically used in cell-penetrating peptides may be replaced by a combination of any of beta-alanine, serine, proline, arginine and histidine or hydroxyproline, suitably a combination of any of beta-alanine, histidine, and hydroxyproline.

In one embodiment, there is provided a peptide having a total length of 40 amino acid residues or less, the peptide comprising:

two or more cationic domains each comprising at least 4 amino acid residues; and one or more hydrophobic domains each comprising at least 3 amino acid residues;

wherein at least one cationic domain comprises histidine residues.

Suitably, wherein at least one cationic domain is histidine rich.

Suitably, what is meant by histidine rich is defined herein in relation to the cationic domains.

Cationic Domain

The present invention relates to short cell-penetrating peptides having a particular structure in which there are at least two cationic domains having a certain length.

References to 'cationic' herein denote an amino acid or domain of amino acids having an overall positive charge at physiological pH.

Suitably, the peptide comprises up to 4 cationic domains, up to 3 cationic domains.

Suitably, the peptide comprises 2 cationic domains.

As defined above, the peptide comprises two or more cationic domains each having a length of at least 4 amino acid residues.

Suitably, each cationic domain has a length of between 4 to 12 amino acid residues, suitably a length of between 4 to 7 amino acid residues.

Suitably, each cationic domain has a length of 4, 5, 6, or 7 amino acid residues.

Suitably, each cationic domain is of similar length, suitably each cationic domain is the same length.

Suitably, each cationic domain comprises cationic amino acids and may also contain polar and or nonpolar amino acids.

Non-polar amino acids may be selected from: alanine, beta-alanine, proline, glycine, cysteine, valine, leucine, isoleucine, methionine, tryptophan, phenylalanine. Suitably non-polar amino acids do not have a charge.

Polar amino acids may be selected from: serine, asparagine, hydroxyproline, histidine, arginine, threonine, tyrosine, glutamine. Suitably, the selected polar amino acids do not have a negative charge.

Cationic amino acids may be selected from: arginine, histidine, lysine. Suitably, cationic amino acids have a positive charge at physiological pH.

Suitably each cationic domain does not comprise anionic or negatively charged amino acid residues.

Suitably each cationic domain comprises arginine, histidine, beta-alanine, hydroxyproline and/or serine residues.

Suitably each cationic domain consists of arginine, histidine, beta-alanine, hydroxyproline and/or serine residues.

Suitably, each cationic domain comprises at least 40%, at least 45%, at least 50% cationic amino acids.

Suitably, each cationic domain comprises a majority of cationic amino acids. Suitably, each cationic domain comprises at least 55%, at least 60%, at least 65% at least 70%, at least 75%, at least 80%, at least 85%, at least 90%, at least 95% cationic amino acids.

Suitably, each cationic domain comprises an isoelectric point (pI) of at least 7.5, at least 8.0, at least 8.5, at least 9.0, at least 9.5, at least 10.0, at least 10.5, at least 11.0, at least 11.5, at least 12.0.

Suitably, each cationic domain comprises an isoelectric point (pI) of at least 10.0.

Suitably, each cationic domain comprises an isoelectric point (pI) of between 10.0 and 13.0

In one embodiment, each cationic domain comprises an isoelectric point (pI) of between 10.4 and 12.5.

Suitably the isoelectric point of a cationic domain is calculated at physiological pH by any suitable means available in the art. Suitably, by using the IPC (<www.isoelectric.org>) a web-based algorithm developed by Lukasz Kozlowski, Biol Direct. 2016; 11:55. DOI: 10.1186/s13062-016-0159-9.

Suitably, each cationic domain comprises at least 1 cationic amino acid, suitably between 1-5 cationic amino acids. Suitably, each cationic domain comprises at least 2 cationic amino acids, suitably between 2-5 cationic amino acids.

Suitably, each cationic domain is arginine rich and/or histidine rich. Suitably a cationic domain may contain both histidine and arginine.

By 'arginine rich' or 'histidine rich' it is meant that at least 40% of the cationic domain is formed of said residue/s.

Suitably, each cationic domain comprises a majority of arginine and/or histidine residues.

Suitably, each cationic domain comprises at least 40%, at least 45%, at least 50%, at least 55%, at least 60%, at least 60%, at least 65%, least 70% arginine and/or histidine residues.

Suitably, a cationic domain may comprise at least 40%, at least 45%, at least 50%, at least 55%, at least 60%, at least 60%, at least 65%, least 70% arginine residues.

Suitably, a cationic domain may comprise at least 40%, at least 45%, at least 50%, at least 55%, at least 60%, at least 60%, at least 65%, least 70% histidine residues.

Suitably, a cationic domain may comprise a total of between 1-5 histidine and 1-5 arginine residues. Suitably, a cationic domain may comprise between 1-5 arginine residues. Suitably, a cationic domain may comprise between 1-5 histidine residues. Suitably, a cationic domain may comprise a total of between 2-5 histidine and 3-5 arginine residues. Suitably, a cationic domain may comprise between 3-5 arginine residues. Suitably, a cationic domain may comprise between 2-5 histidine residues.

Suitably, each cationic domain comprises one or more beta-alanine residues. Suitably, each cationic domain may comprise a total of between 2-5 beta-alanine residues, suitably a total of 2 or 3 beta-alanine residues.

Suitably, a cationic domain may comprise one or more hydroxyproline residues or serine residues.

Suitably, a cationic domain may comprise between 1-2 hydroxyproline residues. Suitably a cationic domain may comprise between 1-2 serine residues.

Suitably all of the cationic amino acids in a given cationic domain may be histidine, alternatively, suitably all of the cationic amino acids in a given cationic domain may be arginine.

Suitably, the peptide may comprise at least one histidine rich cationic domain. Suitably, the peptide may comprise at least one arginine rich cationic domain.

Suitably, the peptide may comprise at least one arginine rich cationic domain and at least one histidine rich cationic domain.

In one embodiment, the peptide comprises two arginine rich cationic domains.

In one embodiment, the peptide comprises two histidine rich cationic domains.

In one embodiment, the peptide comprises two arginine and histidine rich cationic domains.

In one embodiment, the peptide comprises one arginine rich cationic domain and one histidine rich cationic domain.

Suitably, each cationic domain comprises no more than 3 contiguous arginine residues, suitably no more than 2 contiguous arginine residues.

Suitably, each cationic domain comprises no contiguous histidine residues.

Suitably, each cationic domain comprises arginine, histidine and/or beta-alanine residues. Suitably, each cationic domain comprises a majority of arginine, histidine and/or beta-alanine residues. Suitably, at least 70%, at least 75%, at least 80%, at least 85%, at least 90%, at least 95%, 100% of the amino acid residues in each cationic domain are arginine, histidine and/or beta-alanine residues. Suitably, each cationic domain consists of arginine, histidine and/or beta-alanine residues.

In one embodiment, the peptide comprises a first cationic domain comprising arginine and beta-alanine residues and a second cationic domain comprising arginine and beta-alanine residues.

In one embodiment, the peptide comprises a first cationic domain comprising arginine and beta-alanine resides, and a second cationic domain comprising histidine, beta-alanine, and optionally arginine residues.

In one embodiment, the peptide comprises a first cationic domain comprising arginine and beta-alanine resides, and a second cationic domain comprising histidine and beta-alanine residues.

In one embodiment, the peptide comprises a first cationic domain consisting of arginine and beta-alanine residues and a second cationic domain consisting of arginine and beta-alanine residues.

In one embodiment, the peptide comprises a first cationic domain consisting of arginine and beta-alanine residues and a second cationic domain consisting of arginine, histidine and beta-alanine residues.

Suitably, the peptide comprises at least two cationic domains, suitably these cationic domains form the arms of the peptide. Suitably, the cationic domains are located at the N and C terminus of the peptide. Suitably therefore, the cationic domains may be known as the cationic arm domains.

In one embodiment, the peptide comprises two cationic domains, wherein one one is located at the N-terminus of the peptide and one is located at the C-terminus of the peptide. Suitably at either end of the peptide. Suitably no further amino acids or domains are present at the N-terminus and C-terminus of the peptide, with the exception of other groups such as a terminal modification, linker and/or therapeutic molecule. For the avoidance of doubt, such other groups may be present in addition to 'the peptide' described and claimed herein. Suitably therefore each cationic domain forms the terminus of the peptide. Suitably, this does not preclude the presence of a further linker group as described herein.

Suitably, the peptide may comprise up to 4 cationic domains. Suitably, the peptide comprises two cationic domains.

In one embodiment, the peptide comprises two cationic domains that are both arginine rich.

In one embodiment, the peptide comprises one cationic domain that is arginine rich.

In one embodiment, the peptide comprises two cationic domains that are both arginine and histidine rich.

In one embodiment, the peptide comprises one cationic domain that is arginine rich and one cationic domain that is histidine rich.

Suitably, the cationic domains comprise amino acid units selected from the following: R, H, B, RR, HH, BB, RH, HR, RB, BR, HB, BH, RBR, RBB, BRR, BBR, BRB, RBH, RHB, HRB, BRH, HRR, RRH, HRH, HBB, BBH, RHR, BHB, HBH, or any combination thereof.

Suitably a cationic domain may also include serine, proline and/or hydroxyproline residues. Suitably the cationic domains may further comprise amino acid units selected from the following: RP, PR, RPR, RRP, PRR, PRP, Hyp; R[Hyp]R, RR[Hyp], [Hyp]RR, [Hyp]R[Hyp], [Hyp][Hyp]R, R[Hyp][Hyp], SB, BS, or any combination thereof, or any combination with the above listed amino acid units.

Suitably, each cationic domain comprises any of the following sequences: RBRRBRR (SEQ ID NO:1), RBRBR (SEQ ID NO:2), RBRR (SEQ ID NO:3), RBRRBR (SEQ ID NO:4), RRBRBR (SEQ ID NO:5), RBRRB (SEQ ID NO:6), BRBR (SEQ ID NO:7), RBHBH (SEQ ID NO:8), HBHBR (SEQ ID NO:9), RBRHBHR (SEQ ID NO:10), RBRBBHR (SEQ ID NO:11), RBRRBH (SEQ ID NO:12), HBRRBR (SEQ ID NO:13), HBHBH (SEQ ID NO:14), BHBH (SEQ ID NO:15), BRBSB (SEQ ID NO:16), BRB[Hyp]B (SEQ ID NO:17), R[Hyp]H[Hyp]HB (SEQ ID NO:18), R[Hyp]RR[Hyp]R (SEQ ID NO:19) or any combination thereof.

Suitably, each cationic domain consists any of the following sequences: RBRRBRR (SEQ ID NO:1), RBRBR (SEQ ID NO:2), RBRR (SEQ ID NO:3), RBRRBR (SEQ ID NO:4), RRBRBR (SEQ ID NO:5), RBRRB (SEQ ID NO:6), BRBR (SEQ ID NO:7), RBHBH (SEQ ID NO:8), HBHBR (SEQ ID NO:9), RBRHBHR (SEQ ID NO:10), RBRBBHR (SEQ ID NO:11), RBRRBH (SEQ ID NO:12), HBRRBR (SEQ ID NO:13), HBHBH (SEQ ID NO:14), BHBH (SEQ ID NO:15), BRBSB (SEQ ID NO:16), BRB[Hyp]B, R[Hyp]H[Hyp]HB, R[Hyp]RR[Hyp]R (SEQ ID NO:19) or any combination thereof.

Suitably, each cationic domain consists of one of the following sequences: RBRRBRR (SEQ ID NO:1), RBRBR (SEQ ID NO:2), RBRRBR (SEQ ID NO:4), BRBR (SEQ ID NO:7), RBHBH (SEQ ID NO:8), HBHBR (SEQ ID NO:9).

Suitably each cationic domain in the peptide may be identical or different. Suitably each cationic domain in the peptide is different.

Hydrophobic Domain

The present invention relates to short cell-penetrating peptides having a particular structure in which there is at least one hydrophobic domain having a certain length.

References to 'hydrophobic' herein denote an amino acid or domain of amino acids having the ability to repel water or which do not mix with water.

Suitably the peptide comprises up to 3 hydrophobic domains, up to 2 hydrophobic domains. Suitably the peptide comprises 1 hydrophobic domain.

As defined above, the peptide comprises one or more hydrophobic domains each having a length of at least 3 amino acid residues.

Suitably, each hydrophobic domain has a length of between 3-6 amino acids. Suitably, each hydrophobic domain has a length of 5 amino acids.

Suitably, each hydrophobic domain may comprise non-polar, polar, and hydrophobic amino acid residues.

Hydrophobic amino acid residues may be selected from: alanine, valine, leucine, isoleucine, phenylalanine, tyrosine, methionine, and tryptophan.

Non-polar amino acid residues may be selected from: proline, glycine, cysteine, alanine, valine, leucine, isoleucine, tryptophan, phenylalanine, methionine.

Polar amino acid residues may be selected from: Serine, Asparagine, hydroxyproline, histidine, arginine, threonine, tyrosine, glutamine.

Suitably the hydrophobic domains do not comprise hydrophilic amino acid residues.

Suitably, each hydrophobic domain comprises a majority of hydrophobic amino acid residues. Suitably, each hydrophobic domain comprises at least 70%, at least 75%, at least 80%, at least 85%, at least 90%, at least 95%, 100% hydrophobic amino acids. Suitably, each hydrophobic domain consists of hydrophobic amino acid residues.

Suitably, each hydrophobic domain comprises a hydrophobicity of at least 0.3, at least 0.4, at least 0.5, at least 0.6, at least 0.7, at least 0.8, at least 0.8, at least 1.0, at least 1.1, at least 1.2, at least 1.3.

Suitably, each hydrophobic domain comprises a hydrophobicity of at least 0.3, at least 0.35, at least 0.4, at least 0.45.

Suitably, each hydrophobic domain comprises a hydrophobicity of at least 1.2, at least 1.25, at least 1.3, at least 1.35.

Suitably, each hydrophobic domain comprises a hydrophobicity of between 0.4 and 1.4

In one embodiment, each hydrophobic domain comprises of a hydrophobicity of between 0.45 and 0.48.

In one embodiment, each hydrophobic domain comprises a hydrophobicity of between 1.27 and 1.39

Suitably, hydrophobicity is as measured by White and Wimley: W. C. Wimley and S. H. White, "Experimentally determined hydrophobicity scale for proteins at membrane interfaces" Nature Struct Biol 3:842 (1996).

Suitably, each hydrophobic domain comprises at least 3, at least 4 hydrophobic amino acid residues.

Suitably, each hydrophobic domain comprises phenylalanine, leucine, Isoleucine, tyrosine, tryptophan, proline, and glutamine residues. Suitably, each hydrophobic domain consists of phenylalanine, leucine, isoleucine, tyrosine, tryptophan, proline, and/or glutamine residues.

In one embodiment, each hydrophobic domain consists of phenylalanine, leucine, isoleucine, tyrosine and/or glutamine residues.

In one embodiment, each hydrophobic domain consists of tryptophan and/or proline residues.

Suitably, the peptide comprises one hydrophobic domain. Suitably the or each hydrophobic domain is located in the centre of the peptide. Suitably, therefore, the hydrophobic domain may be known as a core hydrophobic domain. Suitably, the or each hydrophobic core domain is flanked on either side by an arm domain. Suitably the arm domains may comprise one or more cationic domains and one or more further hydrophobic domains. Suitably, each arm domain comprises a cationic domain.

In one embodiment, the peptide comprises two arm domains flanking a hydrophobic core domain, wherein each arm domain comprises a cationic domain.

In one embodiment, the peptide consists of two cationic arm domains flanking a hydrophobic core domain.

Suitably the or each hydrophobic domain comprises one of the following sequences:

YQFLI, (SEQ ID NO: 20)

FQILY, (SEQ ID NO: 21)

-continued

```
                              (SEQ ID NO: 22)
ILFQY, (SEQ ID NO: 23)
FQIY, (SEQ ID NO: 24)
WWW, WWPWW, (SEQ ID NO: 25)
WPWW, (SEQ ID NO: 26)
WWPW
``` or any combination thereof.

Suitably the or each hydrophobic domain consists of one of the following sequences:

```
                              (SEQ ID NO: 20)
YQFLI, (SEQ ID NO: 21)
FQILY, (SEQ ID NO: 22)
ILFQY, (SEQ ID NO: 23)
FQIY, (SEQ ID NO: 24)
WWW, WWPWW, (SEQ ID NO: 25)
WPWW, (SEQ ID NO: 26)
WWPW
``` or any combination thereof.

Suitably, the or each hydrophobic domain consists of one of the following sequences

```
                              (SEQ ID NO: 21)
FQILY, (SEQ ID NO: 20)
YQFLI, (SEQ ID NO: 22)
ILFQY.
```

Suitably, the or each hydrophobic domain consists of FQILY (SEQ ID NO:21).

Suitably each hydrophobic domain in the peptide may have the same sequence or a different sequence.

Peptide

The present invention relates to short cell-penetrating peptides for use in transporting therapeutic cargo molecules in the treatment of medical conditions.

The peptide has a sequence that is a contiguous single molecule, therefore the domains of the peptide are contiguous. Suitably, the peptide comprises several domains in a linear arrangement between the N-terminus and the C-terminus. Suitably, the domains are selected from cationic domains and hydrophobic domains described above. Suitably, the peptide consists of cationic domains and hydrophobic domains wherein the domains are as defined above.

Each domain has common sequence characteristics as described in the relevant sections above, but the exact sequence of each domain is capable of variation and modification. Thus a range of sequences is possible for each domain. The combination of each possible domain sequence yields a range of peptide structures, each of which form part of the present invention. Features of the peptide structures are described below.

Suitably, a hydrophobic domain separates any two cationic domains. Suitably, each hydrophobic domain is flanked by cationic domains on either side thereof.

Suitably no cationic domain is contiguous with another cationic domain.

In one embodiment, the peptide comprises one hydrophobic domain flanked by two cationic domains in the following arrangement:

[cationic domain]—[hydrophobic domain]—[cationic domain]

Therefore, suitably the hydrophobic domain may be known as the core domain and each of the cationic domains may be known as an arm domain. Suitably, the hydrophobic arm domains flank the cationic core domain on either side thereof.

In one embodiment, the peptide consists of two cationic domains and one hydrophobic domain.

In one embodiment, the peptide consists of one hydrophobic core domain flanked by two cationic arm domains.

In one embodiment, the peptide consists of one hydrophobic core domain comprising a sequence selected from: YQFLI (SEQ ID NO:20), FQILY (SEQ ID NO:21), ILFQY (SEQ ID NO:22), FQIY (SEQ ID NO:23), WWW, WWPWW (SEQ ID NO:24), WPWW (SEQ ID NO:25), and WWPW (SEQ ID NO:26), flanked by two cationic arm domains each comprising a sequence selected from: RBRRBRR (SEQ ID NO:1), RBRBR (SEQ ID NO:2), RBRR (SEQ ID NO:3), RBRRBR (SEQ ID NO:4), RRBRBR (SEQ ID NO:5), RBRRB (SEQ ID NO:6), BRBR (SEQ ID NO:7), RBHBH (SEQ ID NO:8), HBHBR (SEQ ID NO:9), RBRHBHR (SEQ ID NO:10), RBRBBHR (SEQ ID NO:11), RBRRBH (SEQ ID NO:12), HBRRBR (SEQ ID NO:13), HBHBH (SEQ ID NO:14), BHBH (SEQ ID NO:15), BRBSB (SEQ ID NO:16), BRB[Hyp]B (SEQ ID NO:17), R[Hyp]H[Hyp]HB (SEQ ID NO:18), and R[Hyp]RR[Hyp]R (SEQ ID NO:19).

In one embodiment, the peptide consists of one hydrophobic core domain comprising a sequence selected from: FQILY (SEQ ID NO:21), YQFLI (SEQ ID NO:20), and ILFQY (SEQ ID NO:22), flanked by two cationic arm domains comprising a sequence selected from: RBRRBRR (SEQ ID NO:1), RBRBR (SEQ ID NO:2), RBRRBR (SEQ ID NO:4), BRBR (SEQ ID NO:7), RBHBH (SEQ ID NO:8), HBHBR (SEQ ID NO:9).

In one embodiment, the peptide consists of one hydrophobic core domain comprising the sequence: FQILY (SEQ ID NO:21), flanked by two cationic arm domains comprising a sequence selected from: RBRRBRR (SEQ ID NO:1), RBRBR (SEQ ID NO:2), RBRRBR (SEQ ID NO:4), BRBR (SEQ ID NO:7), RBHBH (SEQ ID NO:8).

In any such embodiment, further groups may be present such as a linker, terminal modification and/or therapeutic molecule.

Suitably, the peptide is N-terminally modified.

Suitably the peptide is N-acetylated, N-methylated, N-trifluoroacetylated, N-trifluoromethylsulfonylated, or N-methylsulfonylated. Suitably, the peptide is N-acetylated.

Optionally, the N-terminus of the peptide may be unmodified.

In one embodiment, the peptide is N-acetylated.

Suitably, the peptide is C-terminal modified.

Suitably, the peptide comprises a C-terminal modification selected from: Carboxy-, Thioacid-, Aminooxy-, Hydrazino-, thioester-, azide, strained alkyne, strained alkene, aldehyde-, thiol or haloacetyl-group.

Advantageously, the C-terminal modification provides a means for linkage of the peptide to the therapeutic molecule.

Accordingly, the C-terminal modification may comprise the linker and vice versa. Suitably, the C-terminal modification may consist of the linker or vice versa. Suitable linkers are described herein elsewhere.

Suitably, the peptide comprises a C-terminal carboxyl group.

Suitably, the C-terminal carboxyl group is provided by a glycine or beta-alanine residue.

In one embodiment, the C terminal carboxyl group is provided by a beta-alanine residue.

Suitably, the C terminal beta-alanine residue is a linker.

Suitably, therefore each cationic domain may further comprise an N or C terminal modification. Suitably the cationic domain at the C terminus comprises a C-terminal modification. Suitably the cationic domain at the N terminus comprises a N-terminal modification. Suitably, the cationic domain at the C terminus comprises a linker group, suitably, the cationic domain at the C terminus comprises a C-terminal beta-alanine. Suitably, the cationic domain at the N terminus is N-acetylated.

The peptide of the present invention is defined as having a total length of 40 amino acid residues or less. The peptide may therefore be regarded as an oligopeptide.

Suitably, the peptide has a total length of between 3-30 amino acid residues, suitably of between 5-25 amino acid residues, of between 10-25 amino acid residues, of between 13-23 amino acid residues, of between 15-20 amino acid residues.

Suitably, the peptide has a total length of at least 12, at least 13, at least 14, at least 15, at least 16, at least 17 amino acid residues.

Suitably the peptide is capable of penetrating cells. The peptide may therefore be regarded as a cell-penetrating peptide.

Suitably, the peptide is for attachment to a therapeutic molecule. Suitably, the peptide is for transporting a therapeutic molecule into a target cell. Suitably, the peptide is for delivering a therapeutic molecule into a target cell. The peptide may therefore be regarded as a carrier peptide.

Suitably, the peptide is capable of penetrating into cells and tissues, suitably into the nucleus of cells. Suitably into muscle tissues.

Suitably, the peptide may be selected from any of the following sequences:

```
Suitably, the peptide may be selected from any of
the following sequences:
                                         (SEQ ID NO: 27)
RBRRBRRFQILYRBRBR (SEQ ID NO: 28)
RBRRBRRFQILYRBRR (SEQ ID NO: 29)
RBRRBRFQILYRRBRBR (SEQ ID NO: 30)
RBRBRFQILYRBRRBRR (SEQ ID NO: 31)
RBRRBRRYQFLIRBRBR (SEQ ID NO: 32)
RBRRBRRILFQYRBRBR
```

```
                                         (SEQ ID NO: 33)
RBRRBRFQILYRBRBR (SEQ ID NO: 34)
RBRRBFQILYRBRRBR (SEQ ID NO: 35)
RBRRBRFQILYBRBR (SEQ ID NO: 36)
RBRRBFQILYRBRBR (SEQ ID NO: 37)
RBRRBRRFQILYRBHBH (SEQ ID NO: 38)
RBRRBRRFQILYHBHBR (SEQ ID NO: 39)
RBRRBRRFQILYHBRBH (SEQ ID NO: 40)
RBRRBRRYQFLIRBHBH (SEQ ID NO: 41)
RBRRBRRILFQYRBHBH (SEQ ID NO: 42)
RBRHBHRFQILYRBRBR (SEQ ID NO: 43)
RBRBBHRFQILYRBHBH (SEQ ID NO: 44)
RBRRBRFQILYRBHBH (SEQ ID NO: 45)
RBRRBRFQILYHBHBH (SEQ ID NO: 46)
RBRRBHFQILYRBHBH (SEQ ID NO: 47)
HBRRBRFQILYRBHBH (SEQ ID NO: 48)
RBRRBFQILYRBHBH (SEQ ID NO: 49)
RBRRBRFQILYBHBH (SEQ ID NO: 50)
RBRRBRYQFLIHBHBH (SEQ ID NO: 51)
RBRRBRILFQYHBHBH (SEQ ID NO: 52)
RBRRBRRFQILYHBHBH
```

Suitably, the peptide may be selected from any of the following additional sequences:

```
                                         (SEQ ID NO: 53)
RBRRBRFQILYBRBS (SEQ ID NO: 54)
RBRRBRFQILYRB[Hyp]

(SEQ ID NO: 55)
RBRRBRFQILYBR[Hyp]R (SEQ ID NO: 56)
RBRRBRRFQILYBRBR (SEQ ID NO: 57)
BRRBRRFQILYBRBR (SEQ ID NO: 58)
RBRRBRWWWBRBR
```

-continued

RBRRBRWWPWWBRBR (SEQ ID NO: 59)

RBRRBRWPWWBRBR (SEQ ID NO: 60)

RBRRBRWWPWBRBR (SEQ ID NO: 61)

RBRRBRRWWWRBRBR (SEQ ID NO: 62)

RBRRBRRWWPWWRBRBR (SEQ ID NO: 63)

RBRRBRRWPWWRBRBR (SEQ ID NO: 64)

RBRRBRRWWPWRBRBR (SEQ ID NO: 65)

RBRRBRRFQILYBRBR (SEQ ID NO: 66)

RBRRBRRFQILYRBR (SEQ ID NO: 67)

BRBRBWWPWWRBRRBR (SEQ ID NO: 68)

RBRRBRRFQILYBHBH (SEQ ID NO: 69)

RBRRBRRFQIYRBHBH (SEQ ID NO: 70)

RBRRBRFQILYBRBH (SEQ ID NO: 71)

RBRRBRFQILYR[Hyp]H[Hyp]H (SEQ ID NO: 72)

R[Hyp]RR[Hyp]RFQILYRBHBH (SEQ ID NO: 73)

R[Hyp]RR[Hyp]RFQILYR[Hyp]H[Hyp]H (SEQ ID NO: 74)

RBRRBRWWWRBHBH (SEQ ID NO: 75)

RBRRBRWWPRBHBH (SEQ ID NO: 76)

RBRRBRPWWRBHBH (SEQ ID NO: 77)

RBRRBRWWPWWRBHBH (SEQ ID NO: 78)

RBRRBRWWPWRBHBH (SEQ ID NO: 79)

RBRRBRWPWWRBHBH (SEQ ID NO: 80)

RBRRBRRWWWRBHBH (SEQ ID NO: 81)

RBRRBRRWWPWWRBHBH (SEQ ID NO: 82)

RBRRBRRWPWWRBHBH (SEQ ID NO: 83)

RBRRBRRWWPWRBHBH (SEQ ID NO: 84)

RRBRRBRFQILYRBHBH (SEQ ID NO: 85)

BRRBRRFQILYRBHBH (SEQ ID NO: 86)

RRBRRBRFQILYBHBH (SEQ ID NO: 87)

BRRBRRFQILYBHBH (SEQ ID NO: 88)

RBRRBHRFQILYRBHBH (SEQ ID NO: 89)

RBRRBRFQILY[Hyp]R[Hyp]R (SEQ ID NO: 101)

R[Hyp]RR[Hyp]RFQILYBRBR (SEQ ID NO: 102)

R[Hyp]RR[Hyp]RFQILY[Hyp]R[Hyp]R (SEQ ID NO: 103)

RBRRBRWWWBRBR (SEQ ID NO: 104)

RBRRBRWWPWWBRBR (SEQ ID NO: 105)

Suitably the peptide consists of one of the following sequences:

RBRRBRRFQILYRBRBR (SEQ ID NO: 27)

RBRRBRRYQFLIRBRBR (SEQ ID NO: 31)

RBRRBRRILFQYRBRBR (SEQ ID NO: 32)

RBRRBRFQILYBRBR (SEQ ID NO: 35)

RBRRBRRFQILYRBHBH (SEQ ID NO: 37)

RBRRBRRFQILYHBHBR (SEQ ID NO: 38)

RBRRBRFQILYRBHBH (SEQ ID NO: 44)

In one embodiment, the peptide consists of the following sequence: RBRRBRFQILYBRBR (SEQ ID NO:35).

In one embodiment, the peptide consists of the following sequence: RBRRBRRFQILYRBHBH (SEQ ID NO:37).

In one embodiment, the peptide consists of the following sequence: RBRRBRFQILYRBHBH (SEQ ID NO:44).

Conjugate

The peptide of the invention may be covalently linked to a therapeutic molecule in order to provide a conjugate.

The therapeutic molecule may be any molecule for treatment of a disease. The therapeutic molecule may be selected from: a nucleic acid, peptide nucleic acid, antisense oligonucleotide (such as PNA, PMO), mRNA, gRNA (for example in the use of CRISPR/Cas9 technology), short interfering RNA, micro RNA, antagomiRNA, peptide, cyclic peptide, protein, pharmaceutical, drug, or nanoparticle.

In one embodiment, the therapeutic molecule is an antisense oligonucleotide.

Suitably the antisense oligonucleotide is comprised of a phosphorodiamidate morpholino oligonucleotide (PMO).

Alternatively the oligonucleotide may be a modified PMO or any other charge-neutral oligonucleotide such as a peptide nucleic acid (PNA), a chemically modified PNA such as a gamma-PNA (Bahal, Nat. Comm. 2016), oligonucleotide phosphoramidate (where the non-bridging oxygen of the phosphate is substituted by an amine or alkylamine such as those described in WO2016028187A1, or any other partially or fully charge-neutralized oligonucleotide.

The therapeutic antisense oligonucleotide sequence may be selected from any that are available, for example antisense oligonucleotides for exon skipping in DMD are described in <https://research-repository.uwa.edu.au/en/publications/antisense-oligonucleotide-induced-exon-skipping-across-the-human->, or a therapeutic antisense oligonucleotide complementary to the ISSN1 or IN7 sequence for the treatment of SMA are described in Zhou, H G T, 2013; and Hammond et al, 2016; and Osman et al, HMG, 2014.

Suitably, the antisense oligonucleotide sequence is for inducing exon skipping for use in the treatment of DMD.

Suitably, the antisense oligonucleotide sequence is for inducing exon skipping in the dystrophin gene for use in the treatment of DMD. Suitably the antisense oligonucleotide sequence may induce exon skipping of one or multiple exons.

In one embodiment, the antisense oligonucleotide sequence is for inducing exon skipping of a single exon of the dystrophin gene for use in the treatment of DMD. Suitably the single exon is selected from any exon implicated in DMD, which may be any exon in the dystrophin gene, such as for example, exon 45, 51 or 53. PMO oligonucleotides of any sequence may be purchased (for example from Gene Tools Inc, USA).

In one embodiment, the therapeutic molecule of the conjugate is an oligonucleotide complementary to the pre-mRNA of a gene target.

Suitably, the oligonucleotide complementary to the pre-mRNA of a gene target gives rise to a steric blocking event that alters the pre-mRNA leading to an altered mRNA and hence a protein of altered sequence. Suitably, the gene target is the dystrophin gene. Suitably the steric blocking event may be exon inclusion or exon skipping. In one embodiment, the steric blocking event is exon skipping, suitably exon skipping of a single exon of the dystrophin gene.

Optionally, lysine residues may be added to one or both ends of a therapeutic molecule (such as a PMO or PNA) before attachment to the peptide to improve water solubility.

Suitably the therapeutic molecule has a molecular weight of less than 5,000 Da, suitably less than 3,000 Da or suitably less than 1,000 Da.

Suitably, the peptide is covalently linked to the therapeutic molecule at the C-terminus.

Suitably, the peptide is covalently linked to the therapeutic molecule through a linker if required. The linker may act as a spacer to separate the peptide sequence from the therapeutic molecule.

The linker may be selected from any suitable sequence.

Suitably the linker is present between the peptide and the therapeutic molecule. Suitably the linker is a separate group to the peptide and the therapeutic molecule. Accordingly, the linker may comprise artificial amino acids.

In one embodiment, the conjugate comprises the peptide covalently linked via a linker to a therapeutic molecule. In one embodiment, the conjugate comprises the following structure:

[peptide]—[linker]—[therapeutic molecule]

In one embodiment, the conjugate consists of the following structure:

[peptide]—[linker]—[therapeutic molecule]

Suitably any of the peptides listed herein may be used in a conjugate according to the invention. In one embodiment, the conjugate comprises a peptide selected from one of the following sequences: RBRRBRFQILYBRBR (SEQ ID NO:35), RBRRBRRFQILYRBHBH (SEQ ID NO:37) and RBRRBRFQILYRBHBH (SEQ ID NO:44).

Suitably, in any case, the peptide may further comprise N-terminal modifications as described above.

Suitable linkers include, for example, a C-terminal cysteine residue that permits formation of a disulphide, thioether or thiol-maleimide linkage, a C-terminal aldehyde to form an oxime, a click reaction or formation of a morpholino linkage with a basic amino acid on the peptide or a carboxylic acid moiety on the peptide covalently conjugated to an amino group to form a carboxamide linkage.

Suitably, the linker is between 1-5 amino acids in length. Suitably the linker may comprise any linker that is known in the art.

Suitably the linker is selected from any of the following sequences: G, BC, XC, C, GGC, BBC, BXC, XBC, X, XX, B, BB, BX and XB. Suitably, wherein X is 6-aminohexanoic acid.

Suitably the linker may be a polymer, such as for example PEG.

In one embodiment, the linker is beta-alanine.

In one embodiment, the peptide is conjugated to the therapeutic molecule through a carboxamide linkage.

The linker of the conjugate may form part of the therapeutic molecule to which the peptide is attached. Alternatively, the attachment of the therapeutic molecule may be directly linked to the C-terminus of the peptide. Suitably, in such embodiments, no linker is required.

Alternatively, the peptide may be chemically conjugated to the therapeutic molecule. Chemical linkage may be via a disulphide, alkenyl, alkynyl, aryl, ether, thioether, triazole, amide, carboxamide, urea, thiourea, semicarbazide, carbazide, hydrazine, oxime, phosphate, phosphoramidate, thiophosphate, boranophosphate, iminophosphates, or thiol-maleimide linkage, for example.

Optionally, cysteine may be added at the N-terminus of a therapeutic molecule to allow for disulphide bond formation to the peptide, or the N-terminus may undergo bromoacetylation for thioether conjugation to the peptide.

The peptide of the invention may equally be covalently linked to an imaging molecule in order to provide a conjugate.

Suitably, the imaging molecule may be any molecule that enables visualisation of the conjugate. Suitably, the imaging molecule may indicate the location of the conjugate. Suitably the location of the conjugate in vitro or in vivo. Suitably, there is provided a method of monitoring the location of a conjugate comprising an imaging molecule comprising: administering the conjugate to a subject and imaging the subject to locate the conjugate.

Examples of imaging molecules include detection molecules, contrast molecules, or enhancing molecules. Suitable imaging molecules may be selected from radionuclides; fluorophores; nanoparticles (such as a nanoshell); nanocages; chromogenic agents (for example an enzyme), radioisotopes, dyes, radiopaque materials, fluorescent compounds, and combinations thereof.

Suitably imaging molecules are visualised using imaging techniques, these may be cellular imaging techniques or medical imaging techniques. Suitable cellular imaging techniques include image cytometry, fluorescent microscopy, phase contrast microscopy, SEM, TEM, for example. Suitable medical imaging techniques include X-ray, fluoroscopy, MRI, scintigraphy, SPECT, PET, CT, CAT, FNRI, for example.

In some cases, the imaging molecule may be regarded as a diagnostic molecule. Suitably, a diagnostic molecule enables the diagnosis of a disease using the conjugate. Suitably, diagnosis of a disease may be achieved through determining the location of the conjugate using an imaging molecule. Suitably, there is provided a method of diagnosis of a disease comprising administering an effective amount of a conjugate comprising an imaging molecule to a subject and monitoring the location of the conjugate.

Suitably, further details such as the linkage of a conjugate comprising an imaging molecule are the same as those described above in relation to a conjugate comprising a therapeutic molecule.

Suitably, the peptide of the invention may be covalently linked to a therapeutic molecule and an imaging molecule in order to provide a conjugate.

Suitably the conjugate is capable of penetrating into cells and tissues, suitably into the nucleus of cells. Suitably into muscle tissues.

Pharmaceutical Composition

The conjugate of the invention may formulated into a pharmaceutical composition.

Suitably the pharmaceutical composition comprises a conjugate of the invention.

Suitably, the pharmaceutical composition may further comprise a pharmaceutically acceptable diluent, adjuvant or carrier.

Suitable pharmaceutically acceptable diluents, adjuvants and carriers are well known in the art.

As used herein, the phrase "pharmaceutically acceptable" refers to those ligands, materials, formulations, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier", as used herein, refers to a pharmaceutically acceptable material, formulation or vehicle, such as a liquid or solid filler, diluent, excipient, solvent or encapsulating material, involved in carrying or transporting the conjugate from one organ or portion of the body, to another organ or portion of the body. Each cell-penetrating peptide must be "acceptable" in the sense of being compatible with the other components of the composition e.g. the peptide and therapeutic molecule, and not injurious to the individual. Lyophilized compositions, which may be reconstituted and administered, are also within the scope of the present composition.

Pharmaceutically acceptable carriers may be, for example, excipients, vehicles, diluents, and combinations thereof. For example, where the compositions are to be administered orally, they may be formulated as tablets, capsules, granules, powders, or syrups; or for parenteral administration, they may be formulated as injections, drop infusion preparations, or suppositories. These compositions can be prepared by conventional means, and, if desired, the active compound (i.e. conjugate) may be mixed with any conventional additive, such as an excipient, a binder, a disintegrating agent, a lubricant, a corrigent, a solubilizing agent, a suspension aid, an emulsifying agent, a coating agent, or combinations thereof.

It should be understood that the pharmaceutical compositions of the present disclosure can further include additional known therapeutic agents, drugs, modifications of compounds into prodrugs, and the like for alleviating, mediating, preventing, and treating the diseases, disorders, and conditions described herein under medical use.

Suitably, the pharmaceutical composition is for use as a medicament. Suitably for use as a medicament in the same manner as described herein for the conjugate. All features described herein in relation to medical treatment using the conjugate apply to the pharmaceutical composition.

Accordingly, in a further aspect of the invention there is provided a pharmaceutical composition according to the fourth aspect for use as a medicament. In a further aspect, there is provided a method of treating a subject for a disease condition comprising administering an effective amount of a pharmaceutical composition according to the fourth aspect to the subject.

Medical Use

The conjugate comprising the peptide of the invention may be used as a medicament for the treatment of a disease.

The medicament may be in the form of a pharmaceutical composition as defined above.

A method of treatment of a patient or subject in need of treatment for a disease condition is also provided, the method comprising the step of administering a therapeutically effective amount of the conjugate to the patient or subject.

Suitably, the medical treatment requires delivery of the therapeutic molecule into a cell, suitably into the nucleus of the cell.

Diseases to be treated may include any disease where improved penetration of the cell and/or nuclear membrane by a therapeutic molecule may lead to an improved therapeutic effect.

Suitably, the conjugate is for use in the treatment of diseases of the neuromuscular system.

Conjugates comprising peptides of the invention are suitable for the treatment of genetic diseases of the neuromuscular system. Conjugates comprising peptides of the invention are suitable for the treatment of genetic neuromuscular diseases. In a suitable embodiment, there is provided a conjugate according to the second aspect for use in the treatment of genetic diseases of the neuromuscular system. Suitably, the conjugate is for use in the treatment of hereditary genetic diseases. Suitably, the conjugate is for use in the treatment of hereditary genetic diseases of the neuromuscular system. Suitably, the conjugate is for use in the treatment of hereditary genetic neuromuscular diseases. Suitably, the conjugate is for use in the treatment of hereditary X-linked genetic diseases of the neuromuscular system. Suitably, the conjugate is for use in the treatment of hereditary X-linked neuromuscular diseases.

Suitably, the conjugate is for use in the treatment of diseases caused by splicing deficiencies. In such embodiments, the therapeutic molecule may comprise an oligonucleotide capable of preventing or correcting the splicing defect and/or increasing the production of correctly spliced mRNA molecules.

Suitably the conjugate is for use in the treatment of any of the following diseases: Duchenne Muscular Dystrophy (DMD), Bucher Muscular Dystrophy (BMD), Menkes disease, Beta-thalassemia, dementia, Parkinson's Disease, Spinal Muscular Atrophy (SMA), myotonic dystrophy (DM), Huntington's Disease, Hutchinson-Gilford Progeria Syndrome, Ataxia-telangiectasia, or cancer.

In one embodiment, the conjugate is for use in the treatment of DMD.

In one embodiment, there is provided a conjugate according to the second aspect for use in the treatment of DMD. Suitably, in such an embodiment, the therapeutic molecule of the conjugate is operable to increase expression of the dystrophin protein. Suitably, in such an embodiment, the therapeutic molecule of the conjugate is operable to increase the expression of functional dystrophin protein.

Suitably the conjugate increases dystrophin expression by 10%, 15%, 20%, 25%, 30%, 35%, 40%, 45%, 50%, 55%, 60%, 65%, 70%. Suitably the conjugate increases dystrophin expression by up to 50%.

Suitably the conjugate restores dystrophin protein expression by 10%, 15%, 20%, 25%, 30%, 35%, 40%, 45%, 50%, 55%, 60%, 65%, 70%. Suitably the conjugate restores dystrophin protein expression by up to 50%.

Suitably the conjugate restores dystrophin protein function by 10%, 15%, 20%, 25%, 30%, 35%, 40%, 45%, 50%, 55%, 60%, 65%, 70%. Suitably the conjugate restores dystrophin protein function by up to 50%.

Suitably, the therapeutic molecule of the conjugate is operable to do so by causing skipping of one or more exons during dystrophin transcription.

Suitably, the therapeutic molecule of the conjugate causes 10%, 15%, 20%, 25%, 30%, 35%, 40%, 45%, 50%, 55%, 60%, 65%, 70%, 75%, 80%, 85% skipping of one or more exons of the dystrophin gene. Suitably, the therapeutic molecule of the conjugate causes up to 50% skipping of one or more exons of the dystrophin gene.

Suitably, the patient or subject to be treated may be any animal or human. Suitably, the patient or subject may be a non-human mammal. Suitably the patient or subject may be male or female. In one embodiment, the subject is male.

Suitably, the patient or subject to be treated may be any age. Suitably the patient or subject to be treated is aged between 0-40 years, suitably 0-30, suitably 0-25, suitably 0-20 years of age.

Suitably, the conjugate is for administration to a subject systemically for example by intramedullary, intrathecal, intraventricular, intravitreal, enteral, parenteral, intravenous, intra-arterial, intramuscular, intratumoral, subcutaneous oral or nasal routes.

In one embodiment, the conjugate is for administration to a subject intravenously.

In one embodiment, the conjugate is for administration to a subject intravenously by injection.

Suitably, the conjugate is for administration to a subject in a "therapeutically effective amount", by which it is meant that the amount is sufficient to show benefit to the individual. The actual amount administered, and rate and time-course of administration, will depend on the nature and severity of the disease being treated. Decisions on dosage are within the responsibility of general practitioners and other medical doctors. Examples of the techniques and protocols can be found in Remington's Pharmaceutical Sciences, 20th Edition, 2000, pub. Lippincott, Williams & Wilkins.

Exemplary doses may be between 0.01 mg/kg and 50 mg/kg, 0.05 mg/kg and 40 mg/kg, 0.1 mg/kg and 30 mg/kg, 0.5 mg/kg and 18 mg/kg, 1 mg/kg and 16 mg/kg, 2 mg/kg and 15 mg/kg, 5 mg/kg and 10 mg/kg, 10 mg/kg and 20 mg/kg, 12 mg/kg and 18 mg/kg, 13 mg/kg and 17 mg/kg.

Advantageously, the dosage of the conjugates of the present invention is an order or magnitude lower than the dosage required to see any effect from the therapeutic molecule alone.

Suitably, after administration of the conjugates of the present invention, one or more markers of toxicity are significantly reduced compared to prior conjugates using currently available peptide carriers Suitable markers of toxicity may be markers of nephrotoxicity.

Suitable markers of toxicity include KIM-1, NGAL, BUN, creatinine, alkaline phosphatase, alanine transferase, and aspartate aminotransferase.

Suitably the level of at least one of KIM-1, NGAL, and BUN is reduced after administration of the conjugates of the present invention when compared to prior conjugates using currently available peptide carriers.

Suitably the levels of each of KIM-1, NGAL, and BUN are reduced after administration of the conjugates of the present invention when compared to prior conjugates using currently available peptide carriers.

Suitably, the levels of the or each marker/s is significantly reduced when compared to prior conjugates using currently available peptide carriers.

Suitably the levels of the or each marker/s is reduced by up to 5%, 10%, 15%, 20%, 25%, 30%, 35%, 40%, 45%, 50% after administration of the conjugates of the present invention when compared to prior conjugates using currently available peptide carriers.

Advantageously, the toxicity of the peptides and therefore the resulting conjugates is significantly reduced compared to prior cell-penetrating peptides and conjugates. In particular, KIM-1 and NGAL-1 are markers of toxicity and these are significantly reduced by up to 120 times compared to prior conjugates using currently available peptide carriers.

Nucleic Acids and Hosts

Peptides of the invention may be produced by any standard protein synthesis method, for example chemical synthesis, semi-chemical synthesis or through the use of expression systems.

Accordingly, the present invention also relates to the nucleotide sequences comprising or consisting of the DNA coding for the peptides, expression systems e.g. vectors comprising said sequences accompanied by the necessary sequences for expression and control of expression, and host cells and host organisms transformed by said expression systems.

Accordingly, a nucleic acid encoding a peptide according to the present invention is also provided.

Suitably, the nucleic acids may be provided in isolated or purified form.

An expression vector comprising a nucleic acid encoding a peptide according to the present invention is also provided.

Suitably, the vector is a plasmid.

Suitably the vector comprises a regulatory sequence, e.g. promoter, operably linked to a nucleic acid encoding a peptide according to the present invention. Suitably, the expression vector is capable of expressing the peptide when transfected into a suitable cell, e.g. mammalian, bacterial or fungal cell.

A host cell comprising the expression vector of the invention is also provided.

Expression vectors may be selected depending on the host cell into which the nucleic acids of the invention may be inserted. Such transformation of the host cell involves conventional techniques such as those taught in Sambrook et al [Sambrook, J., Russell, D. (2001) Molecular Cloning: A Laboratory Manual, Cold Spring Harbor Laboratory Press, NY, USA]. Selection of suitable vectors is within the skills of the person knowledgeable in the field. Suitable vectors include plasmids, bacteriophages, cosmids, and viruses.

The peptides produced may be isolated and purified from the host cell by any suitable method e.g. precipitation or chromatographic separation e.g. affinity chromatography.

Suitable vectors, hosts and recombinant techniques are well known in the art.

In this specification the term "operably linked" may include the situation where a selected nucleotide sequence and regulatory nucleotide sequence are covalently linked in such a way as to place the expression of a nucleotide coding sequence under the control of the regulatory sequence, as such, the regulatory sequence is capable of effecting transcription of a nucleotide coding sequence which forms part or all of the selected nucleotide sequence. Where appropriate, the resulting transcript may then be translated into a desired peptide.

BRIEF DESCRIPTION OF THE DRAWINGS

Certain embodiments of the present invention will now be described with reference to the following figures and tables in which.

Figure 1:
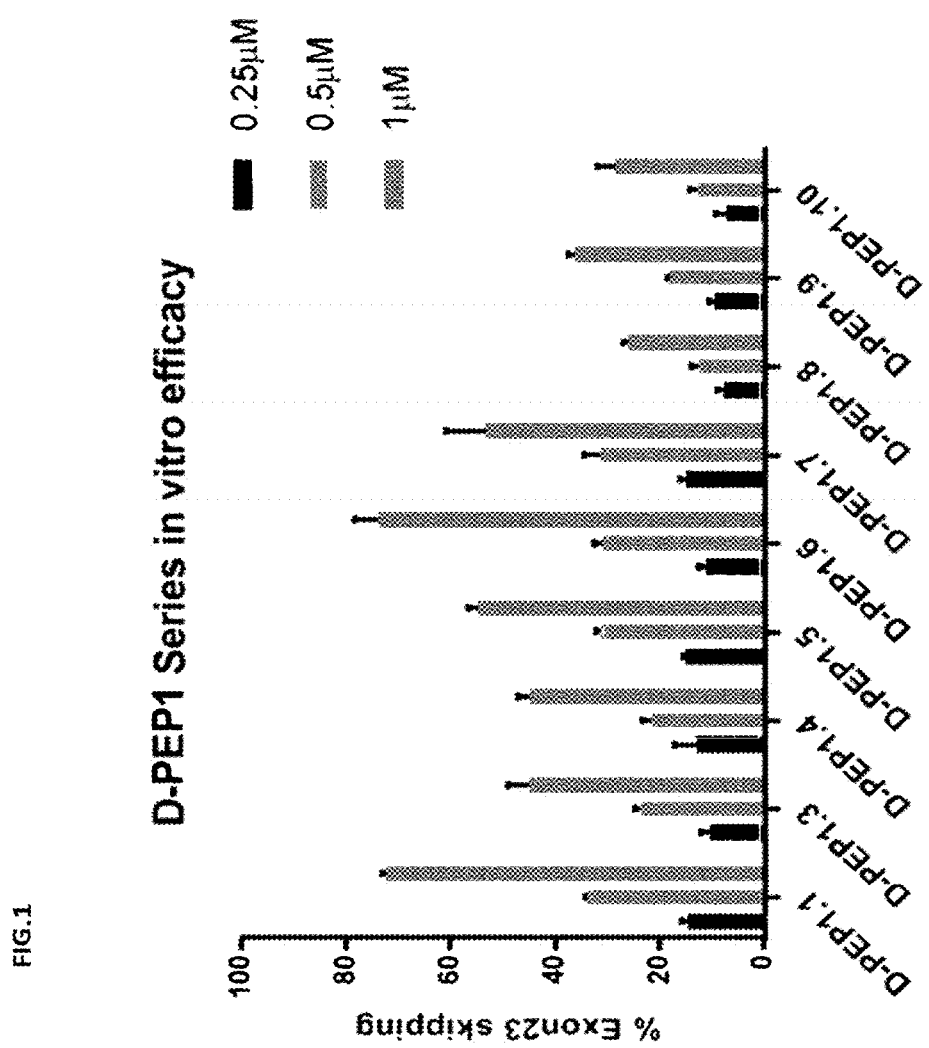
FIG. 1: shows the in vitro exon 23 skipping efficacy of some of the DPEP1 series of peptides conjugated to an antisense therapeutic PMO at 0.25 µM, 0.5 µM and 1 µM in H2K-mdx cells as measured by densitometry analysis of nested RT-PCR (Error bars: standard deviation, n≥3)

Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive.

The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed. The reader's attention is directed to all papers and documents which are filed concurrently with or previous to this specification in connection with this application and which are open to public inspection with this specification, and the contents of all such papers and documents are incorporated herein by reference.

EXAMPLES

1. Materials and Methods 1.1 P-PMO Synthesis and Preparation

9-Fluroenylmethoxycarbonyl (Fmoc) protected L-amino acids, benzotriazole-1-yl-oxy-tris-pyrrolidino-phosphonium (PyBOP), 2-(1H-benzotriazole-1-yl)-1,1,3,3-tetramethyl-uronium hexafluorophosphate (HBTU), and the Fmoc-β-Ala-OH preloaded Wang resin (0.19 or 0.46 mmol g$^{-1}$) were obtained from Merck (Hohenbrunn, Germany). HPLC grade acetonitrile, methanol and synthesis grade N-methyl-2-pyrrolidone (NMP) were purchased from Fisher Scientific (Loughborough, UK). Peptide synthesis grade N,N-dimethylformamide (DMF) and diethyl ether were obtained from VWR (Leicestershire, UK). Piperidine and trifluoroacetic acid (TFA) were obtained from Alfa Aesar (Heysham, England). PMO was purchased from Gene Tools Inc. (Philomath, USA). Chicken Embryo Extract and horse serum were obtained from Sera Laboratories International Ltd (West Sussex, UK). Interferon was obtained from Roche Applied Science (Penzberg, Germany). All other reagents were obtained from Sigma-Aldrich (St. Louis, Mo., USA) unless otherwise stated. MALDI-TOF mass spectrometry was carried out using a Voyager DE Pro BioSpectrometry workstation. A stock solution of 10 mg mL$^{-1}$ of α-cyano-4-hydroxycinnamic acid or sinapinic acid in 50% acetonitrile in water was used as matrix. Error bars are ±0.1%.

1.2 Synthesis of P-PMO Peptides for Screening in H2k mdx Cells a) Preparation of a Library of Peptide Variants Peptides were either prepared on a 10 μmol scale using an Intavis Parallel Peptide Synthesizer or on a 100 μmol scale using a CEM Liberty Blue™ Peptide Synthesizer (Buckingham, UK) using Fmoc-β-Ala-OH preloaded Wang resin (0.19 or 0.46 mmol g$^{-1}$, Merck Millipore) by applying standard Fmoc chemistry and following manufacturer's recommendations. In the case of synthesis using the Intavis Parallel Peptide Synthesizer, double coupling steps were used with a PyBOP/NMM coupling mixture followed by acetic anhydride capping after each step. For synthesis using the CEM Liberty Blue Peptide Synthesizer, single standard couplings were implemented for all amino acids except arginine, which was performed by double couplings. The coupling was carried out once at 75° C. for 5 min at 60-watt microwave power except for arginine residues, which were coupled twice each. Each deprotection reaction was carried out at 75° C. twice, once for 30 sec and then for 3 min at 35-watt microwave power. Once synthesis was complete, the resin was washed with DMF (3×50 mL) and the N-terminus of the solid phase bound peptide was acetylated with acetic anhydride in the presence of DIPEA, at room temperature. After acetylation of the N-terminus, the peptide resin was washed with DMF (3×20 mL) and DCM (3×20 mL). The peptides were cleaved from the solid support by treatment with a cleavage cocktail consisting of trifluoroacetic acid (TFA):H$_2$O:triisopropylsilane (TIPS) (95%: 2.5%: 2.5%: 3-10 mL) for 3 h at room temperature. After peptide release, excess TFA was removed by sparging with nitrogen. The crude peptide was precipitated by the addition of cold diethyl ether (15-40 mL depending on scale of the synthesis) and centrifuged at 3200 rpm for 5 min. The crude peptide pellet was washed thrice with cold diethyl ether (3×15 mL) and purified by RP-HPLC using a Varian 940-LC HPLC System fitted with a 445-LC Scale-up module and 440-LC fraction collector. Peptides were purified by semi-preparative HPLC on an RP-C18 column (10×250 mm, Phenomenex Jupiter) using a linear gradient of CH$_3$CN in 0.1% TFA/H$_2$O with a flow rate of 15 mL min$^{-1}$. Detection was performed at 220 nm and 260 nm. The fractions containing the desired peptide were combined and lyophilized to yield the peptide as a white solid.

TABLE 1 peptides as synthesised for testing in the examples with N-terminal acetylation and C-terminal beta-alanine linker. Pip9b2 and R6Gly are comparative peptides. R6Gly uses a C-terminal glycine as a linker.

| Peptide Number | Sequence ID NO. incorporated | Sequence Tested (with additional C and N terminal modifications) |
| --- | --- | --- |
| D-PEP 1.1 | 27 | Ac-RBRRBRRFQILYRBRBR-B |
| D-PEP 1.2 | 28 | Ac-RBRRBRRFQILYRBRR-B |
| D-PEP 1.3 | 29 | Ac-RBRRBRFQILYRRBRBR-B |
| D-PEP 1.4 | 30 | Ac-RBRBRFQILYRBRRBRR-B |
| D-PEP 1.5 | 31 | Ac-RBRRBRRYQFLIRBRBR-B |
| D-PEP 1.6 | 32 | Ac-RBRRBRRILFQYRBRBR-B |
| D-PEP 1.7 | 33 | Ac-RBRRBRFQILYRBRBR-B |
| D-PEP 1.8 | 34 | Ac-RBRRBFQILYRBRRBR-B |
| D-PEP 1.9 | 35 | Ac-RBRRBRFQILYBRBR-B |
| D-PEP 1.10 | 36 | Ac-RBRRBFQILYRBRBR-B |
| D-PEP 3.1 | 37 | Ac-RBRRBRRFQILYRBHBH-B |
| D-PEP 3.2 | 38 | Ac-RBRRBRRFQILYHBHBR-B |
| D-PEP 3.3 | 39 | Ac-RBRRBRRFQILYHBRBH-B |
| D-PEP 3.4 | 40 | Ac-RBRRBRRYQFLIRBHBH-B |
| D-PEP 3.5 | 41 | Ac-RBRRBRRILFQYRBHBH-B |
| D-PEP 3.6 | 42 | Ac-RBRHBHRFQILYRBRBR-B |
| D-PEP 3.7 | 43 | Ac-RBRBBHRFQILYRBHBH-B |
| D-PEP 3.8 | 44 | Ac-RBRRBRFQILYRBHBH-B |
| D-PEP 3.9 | 45 | Ac-RBRRBRFQILYHBHBH-B |
| D-PEP 3.10 | 46 | Ac-RBRRBHFQILYRBHBH-B |
| D-PEP 3.11 | 47 | Ac-HBRRBRFQILYRBHBH-B |
| D-PEP 3.12 | 48 | Ac-RBRRBFQILYRBHBH-B |
| D-PEP 3.13 | 49 | Ac-RBRRBRFQILYBHBH-B |
| D-PEP 3.14 | 50 | Ac-RBRRBRYQFLIHBHBH-B |
| D-PEP 3.15 | 51 | Ac-RBRRBRILFQYHBHBH-B |
| D-PEP 3.16 | 52 | Ac-RBRRBRRFQILYHBHBH -B |
| Pip9b2 | 113 | Ac-RXRRBRR-FQILY-RBRXR-B |
| R6Gly | 114 | RRRRRR-G | b) Synthesis of a Library of PMO-Peptide Conjugates

A 25-mer PMO antisense sequence for mouse dystrophin exon-23 (GGCCAAACCTCGGCTTACCTGAAAT (SEQ ID NO:90)) was used. The peptide was conjugated to the 3′-end of the PMO through its C-terminal carboxyl group. This was achieved using 2.3 and 2 equivalents of PyBOP and HOAt in NMP respectively in the presence of 2.3 equivalents of DIPEA over peptide and 2.5 fold excess of peptide over PMO dissolved in DMSO. In a few examples, 2.3 equivalents of HBTU were used in place of PyBOP for activation of the C-terminal carboxyl group of the peptide. In general, to a solution of peptide (2500 nmol) in N-methylpyrrolidone (NMP, 80 μL) were added PyBOP (19.2 μL of 0.3 M in NMP), HOAt in (16.7 μL of 0.3 M NMP), DIPEA (1.0 μL) and PMO (100 μL of 10 mM in DMSO). The mixture was left for 2.5 h at 40° C. and the reaction was quenched by the addition of 0.1% TFA in $H_2O$ (300 μL). This solution was purified by Ion exchange chromatography using a converted Gilson HPLC system. The PMO-peptide conjugates were purified on an ion exchange column (Resource S 4 mL, GE Healthcare) using a linear gradient of sodium chloride (0 to 1 M) in sodium phosphate buffer (25 mM, pH 7.0) containing 20% CH3CN at a flow rate of 4 mL min-1. The fractions containing the desired compound were combined and lyophilized to yield the peptide-PMO derivative as a white solid. The removal of excess salts from the peptide-PMO conjugate was afforded through the filtration of the fractions collected after ion exchange using an Amicon® ultra-15 3K centrifugal filter device. The conjugate was lyophilized and analyzed by MALDI-TOF. The conjugates were dissolved in sterile water and filtered through a 0.22 μm cellulose acetate membrane before use. The concentration of peptide-PMO was determined by the molar absorption of the conjugates at 265 nm in 0.1 N HCl solution. (see Table 2 for yields).

TABLE 2

Yields of P-PMO conjugates for cell culture analysis
(The yields are based on dried weight of the lyophilised purified ppmo. The purity for the P-PMOs is greater than 95% as ascertained by normal phase HPLC at 220 nm and 260 nm.)

| Peptide-PMO | Yield |
| --- | --- |
| D-Pep 1.1-PMO | 36% |
| D-Pep 1.2-PMO | — |
| D-Pep 1.3-PMO | 25%[a] |
| D-Pep 1.4-PMO | 24%[a] |
| D-Pep 1.5-PMO | 24%[a] |
| D-Pep 1.6-PMO | 25%[a] |
| D-Pep 1.7-PMO | 33% |
| D-pep 1.8-PMO | 41% |
| D-Pep 1.9-PMO | 35% |
| D-Pep 1.10-PMO | 33% |
| D-Pep 3.1-PMO | 28% |
| D-Pep 3.2-PMO | 33% |
| D-Pep 3.3-PMO | 33% |
| D-Pep 3.4-PMO | 35% |
| D-Pep 3.5-PMO | 37% |
| D-Pep 3.6-PMO | 34% |
| D-Pep 3.7-PMO | 26% |
| D-pep 3.8-PMO | 34% |
| D-Pep 3.9-PMO | 28% |
| D-Pep 3.10-PMO | 28% |
| D-Pep 3.11-PMO | 29% |
| D-Pep 3.12-PMO | 29% |
| D-Pep 3.13-PMO | 31% |
| D-Pep 3.14-PMO | 34% |
| D-Pep 3.15-PMO | 32% |
| D-Pep 3.16-PMO | — |

[a]The P-PMO was synthesised using HBTU activation instead of PyBOP.

1.3 Cell Culture

Murine H2k mdx myoblasts were cultured in gelatin (0.01%) coated flasks at 33° C., under 10% $CO_2$ in Dulbecco's modified Eagles medium (DMEM PAA laboratories) supplemented with 20% heat-inactivated fetal bovine serum (FBS Gold, PAA laboratories), 2% chicken embryo extract (Seralab), 1% penicillin-streptomycin-neomycin antibiotic mixture (PSN, Gibco) and 3 μg/μL γ-interferon (Roche). Cells were seeded in gelatin (0.01%) coated 24-well plates at a density of 2×10⁵ cell/mL and left for 2 days at 33° C., 10% $CO_2$. To differentiate into myotubes, cells were further grown in DMEM supplemented with 5% horse serum (Sigma) and 1% PSN at 37° C., under 5% $CO_2$ for 2 days.

1.4 Cell Transfection

Cells were incubated with peptide-PMO conjugates prepared as described above which were made up in serum-free Opti-MEM and 350 µL was added to each well as duplicates and incubated at 37° C. for 4 hr. The transfection medium was then replaced with DMEM supplemented with 5% horse serum and 1% PSN and the cells incubated for a further 20 hr at 37° C. Cells were washed with PBS and 0.5 mL of TRI RNA (Sigma) isolation reagent was added to each well. Cells were frozen at −80° C. for 1 hr.

1.5 RNA Extraction and Nested RT-PCR Analysis

Total cellular RNA was extracted using TRI reagent with an extra further precipitation with ethanol. The purified RNA was quantified using a Nanodrop® ND-1000 (Thermo Scientific). The RNA (400 ng) was used as a template for RT-PCR using a OneStep RT-PCR Kit (Roche, Indianapolis, USA). For primer sequences refer to Table 4. The cycle conditions for the initial reverse transcription were 50° C. for 30 min and 94° C. for 7 min for 1 cycle followed by 30 cycles of 94° C. for 20 sec, 55° C. for 40 sec and 68° C. for 80 sec. One microlitre of the RT-PCR product was used as template for the second PCR step. The amplification was carried out using 0.5 U of SuperTAQ in 25 cycles at 94° C. for 30 sec, 55° C. for 1 min and 72° C. for 1 min. the products were separated by electrophoresis using 1.5% agarose gel. The images of agarose gels were taken on a Molecular Imager ChemiDoc™ XRS+ imaging system (Bio-Rad, UK) and the images were analysed using Image Lab (V4.1). Microsoft Excel was used to analyse and plot the exon-skipping assay data, which were expressed as the percentage of exon-23 skipping from at least three independent experiments.

1.6 Synthesis of PMO-Peptide Conjugates for Testing in H2k Mdx Mice a) Synthesis of Peptide Variants Peptides were synthesized on a 100 µmol scale using a CEM Liberty Blue™ microwave Peptide Synthesizer (Buckingham, UK) and Fmoc chemistry following manufacturer's recommendations. The side chain protecting groups used were labile to trifluoroacetic acid treatment and the peptide was synthesized using a 5-fold excess of Fmoc-protected amino acids (0.25 mmol) that were activated using PyBOP (5-fold excess) in the presence of DIPEA. Piperidine (20% v/v in DMF) was used to remove N-Fmoc protecting groups. The coupling was carried out once at 75° C. for 5 min at 60-watt microwave power except for arginine residues, which were coupled twice each. Each deprotection reaction was carried out at 75° C. twice, once for 30 sec and then once for 3 min at 35-watt microwave power. Once synthesis was complete, the resin was washed with DMF (3×50 mL) and the N-terminus of the solid phase bound peptide was acetylated with acetic anhydride in the presence of DI PEA at room temperature. After acetylation of the N-terminus, the peptide resin was washed with DMF (3×20 mL) and DCM (3×20 mL). The peptide was cleaved from the solid support by treatment with a cleavage cocktail consisting of trifluoroacetic acid (TFA):$H_2O$:triisopropylsilane (TIPS) (95%: 2.5%: 2.5%, 10 mL) for 3 h at room temperature. Excess TFA was removed by sparging with nitrogen. The cleaved peptide was precipitated via the addition of ice-cold diethyl ether and centrifuged at 3000 rpm for 5 min. The crude peptide pellet was washed thrice with cold diethyl ether (3×40 mL) and purified by RP-HPLC using a Varian 940-LC HPLC System fitted with a 445-LC Scale-up module and 440-LC fraction collector. Peptides were purified by semi-preparative HPLC on an RP-C18 column (10×250 mm, Phenomenex Jupiter) using a linear gradient of $CH_3CN$ in 0.1% TFA/$H_2O$ with a flow rate of 15 mL $min^{-1}$. Detection was performed at 220 nm and 260 nm.

b) Synthesis of PMO-Peptide Conjugates

A 25-mer PMO antisense sequence for mouse dystrophin exon-23 (GGCCAAACCTCGGCTTACCTGAAAT (SEQ ID NO:90)) was used. The peptide was conjugated to the 3'-end of the PMO through its C-terminal carboxyl group. This was achieved using 2.3 and 2-fold equivalents of PyBOP and HOAt in NMP respectively in the presence of 2.3 eq of DIPEA over peptide and a 2.5-fold excess of peptide over PMO dissolved in DMSO. In a few examples, HBTU (2.3 equivalents) were used in place of PyBOP for activation of the C-terminal carboxyl group of the peptide. In general, to a solution of peptide (10 µmop in N-methylpyrrolidone (NMP, 100 µL) were added PyBOP (76.6 µL of 0.3 M in NMP), HOAt in (66.7 µL of 0.3 M NMP), DIPEA (4.0 µL) and PMO (400 µL of 10 mM in DMSO). The mixture was left for 2 h at 40° C. and the reaction was quenched by the addition of 0.1% TFA (1 mL). The reaction was purified on a cation exchange chromatography column (Resource S 6 mL column, GE Healthcare) using a linear gradient of sodium chloride (0 to 1 M) in sodium phosphate buffer (25 mM, pH 7.0) containing 20% CH3CN at a flow rate of 6 mL min-1. The removal of excess salts from the peptide-PMO conjugate was afforded through the filtration of the fractions collected after ion exchange using an Amicon® ultra-15 3K centrifugal filter device. The conjugate was lyophilized and analyzed by MALDI-TOF. The conjugates were dissolved in sterile water and filtered through a 0.22 µm cellulose acetate membrane before use. The concentration of peptide-PMO was determined by the molar absorption of the conjugates at 265 nm in 0.1 N HCl solution. Overall yields (Table 3) were 25-36% based on PMO.

TABLE 3

Yields of P-PMO conjugates synthesized on larger scale for in vivo analysis (The yields are based on dried weight of the lyophilised purified ppmo. The purity for the PPMOs is greater than 95% as ascertained by normal phase HPLC at 220 nm and 260 nm.)

| Peptide-PMO | Yield |
| --- | --- |
| D-Pep 1.1-PMO | 36% |
| D-Pep 1.3-PMO | 25%[a] |
| D-Pep 1.4-PMO | 24%[a] |
| D-Pep 1.5-PMO | 25%[a] |
| D-Pep 1.6-PMO | 25%[a] |
| D-Pep 3.1-PMO | 28% |
| D-Pep 3.2-PMO | 33% |
| D-Pep 3.7-PMO | 26% |
| D-pep 3.8-PMO | 34% |
| D-Pep 3.9-PMO | 28% |
| D-Pep 3.10-PMO | 28% |

[a]The PPMO was synthesised using HBTU activation instead of PyBOP 1.7 In Vivo Assessment of Dystrophin Restoration by P-PMO Experiments were conducted in the Biomedical Sciences Unit, University of Oxford, under Home Office Project Licence authorisation following institutional ethical review. Mice were housed in a minimal disease facility; the environment was temperature controlled with a 12 hour light-dark cycle. All animals received commercial rodent chow and water ad libitum.

Experiments were performed in 10-12 week old female mdx mice. Mdx mice were restrained prior to a single tail vein injection of 10 mg/kg of P-PMO. One week post injection mice were sacrificed and TA, heart and diaphragm muscles removed and snap frozen in dry-ice cooled isopentane and stored at −80° C.

1.8 Western Blot Analysis

To assess the duration of dystrophin restoration following a single administration, one-third of the muscle (for TA and diaphragm) or ninety 7 μm thick transverse cryosections (for heart) were lysed in 300 μl buffer (50 mM Tris pH 8, 150 mM NaCl, 1% NP40, 0.5% sodium deoxycholate, 10% SDS and protease/phosphatase inhibitors) prior to centrifuging at 13000 rpm (Heraeus, #3325B) for 10 min. Supernatant was collected and heated at 100° C. for 3 min. Protein was quantified by BCA method and 40 μg protein/sample were resolved in a NuPage a 3-8% Tris-Acetate gel as previously described (19). Proteins were transferred to a 0.45 μm pore size PVDF membrane for 1 h at 30V followed by 1 h at 100V, and probed with monoclonal anti-dystrophin (1:200, NCL-DYS1, Novocastra) and anti-vinculin (loading control, 1:100 000, hVIN-1, Sigma) antibodies as previously described (37). Secondary antibody IRDye 800CW goat anti-mouse was used at a dilution of 1:20000 (LiCOR).

The levels of dystrophin restoration in P-PMO treated mdx mice were expressed as relative to the levels of C57BL/10 wildtype control mice, considered as 100%. For this, a standard curve was generated by including 5 serial C57BL/10 protein dilutions in parallel to the P-PMO treated mdx samples. Dilution series were as follows: 75%, 40%, 15%, 5% or 0% respectively of the 40 μg total protein loaded per lane were from C57BL/10 protein lysates and the remaining from un-treated mdx protein lysates. These standards were aliquoted and used in each western blot in parallel to the treated mdx samples. For all standards and treated samples, Dystrophin intensity quantification was performed by Fluorescence Odyssey imaging system and normalized by calculating the ratio to the Vinculin fluorescence intensity in all samples. Standard normalized values were plotted against their known concentration of dystrophin to obtain the mathematical expression of best fit and this expression used to interpolate the normalized values of each sample of P-PMO treated mdx mice.

1.9 RT-qPCR Analysis of In Vivo Dmd Exon 23 Skipping

Quantification of exclusion of exon 23 from the mouse Dmd transcript was performed on skeletal muscle and heart tissue treated with peptide-PMO. Briefly, RNA was extracted from homogenised tissue using Trizol-based extraction method and cDNA synthesised using random primers. Primer/probes were synthesised by Integrated DNA Technologies and designed to amplify a region spanning exon 23-24 representing unskipped product (mDMD23-24, see Table 4), or to amplify specifically transcripts lacking exon 23 using a probe spanning the boundary of exon 22 and 24 (mDMD22-24). Levels of respective transcripts were determined by calibration to standard curves prepared using known transcript quantities, and skipping percentages derived by [skip]/[skip+unskip].

TABLE 4

Primer and probe sequences for quantification of exon 23 skipping by nested RT-PCR or quantitative RT-PCR methods.

| Assay ID | Primer Sequence (5'-3') | Sequence ID NO. |
|---|---|---|
| Nested RT-PCR | | |
| Exon20Fo | CAGAATTCTGCCAATTGCTGAG | 91 |
| Exon26Ro | TTCTTCAGCTTGTGTCATCC | 92 |
| Exon20Fi | CCCAGTCTACCACCCTATCAGAGC | 93 |
| Exon26Ri | CCTGCCTTTAAGGCTTCCTT | 94 |
| qRT-PCR | | |
| mDMD23-24 | Primer 1 CAGGCCATTCCTCTTTCAGG | 95 |
| | Primer 2 GAAACTTTCCTCCCAGTTGGT | 96 |
| | Probe /5FAM/TCAACTTCA/ZEN/GCCATCCATT TCTGTAAGGT/3IABKFQ/ | 97 |
| mDMD22-24 | Primer 1 CTGAATATGAAATAATGGAGG AGAGACTCG | 98 |
| | Primer 2 CTTCAGCCATCCATTTCTGTA AGGT | 99 |
| | Probe /5FAM/ATGTGATTC/ZEN/TGTA ATTTCC/3IABKFQ/ | 100 |

1.10 Toxicological Assessment of Peptide-PMO

Female C57BL/6 mice aged 8-10 weeks were administered a single 30 mg/kg dose of peptide-PMO in 0.9% saline by bolus intravenous tail vein injection. Urine was non-invasively collected under chilled conditions at Day 2 and Day 7 post-administration following 20 hours housing in metabolic cages (Tecniplast, UK). Serum was collected from jugular vein at Day 7 at necropsy, as was tibialis anterior, diaphragm and heart tissue.

The same procedure was followed at different single dosage amounts ranging from 2.5 mg/kg up to 50 mg/kg of peptide-PMO in 0.9% saline by intravenous tail vein injection.

Urinary levels of KIM-1 (Kidney injury molecule-1) and NGAL (Neutrophil Gelatinase-Associated Lipocalin) were quantified by ELISA (KIM-1 R&D cat #MKM100, NGAL R&D cat #MLCN20) following appropriate dilution of urine to fit standard curves. Values were normalised to urinary creatinine levels that were quantified at MRC Harwell Institute, Mary Lyon Centre, Oxfordshire, UK. Serum blood urea nitrogen levels were quantified at MRC Harwell Institute, Mary Lyon Centre, Oxfordshire, UK.

All levels were quanitifed on an AU680 Clinical Chemistry Analyser, Beckman Coulter.

Quantification of exon skipping efficacy was determined by quantitative RT-PCR of exon 23 skipped and unskipped transcripts and expressed as percentage of skipped versus total (skipped and unskipped) transcripts (see Table 4 for sequences).

2. Results

Figure 2:
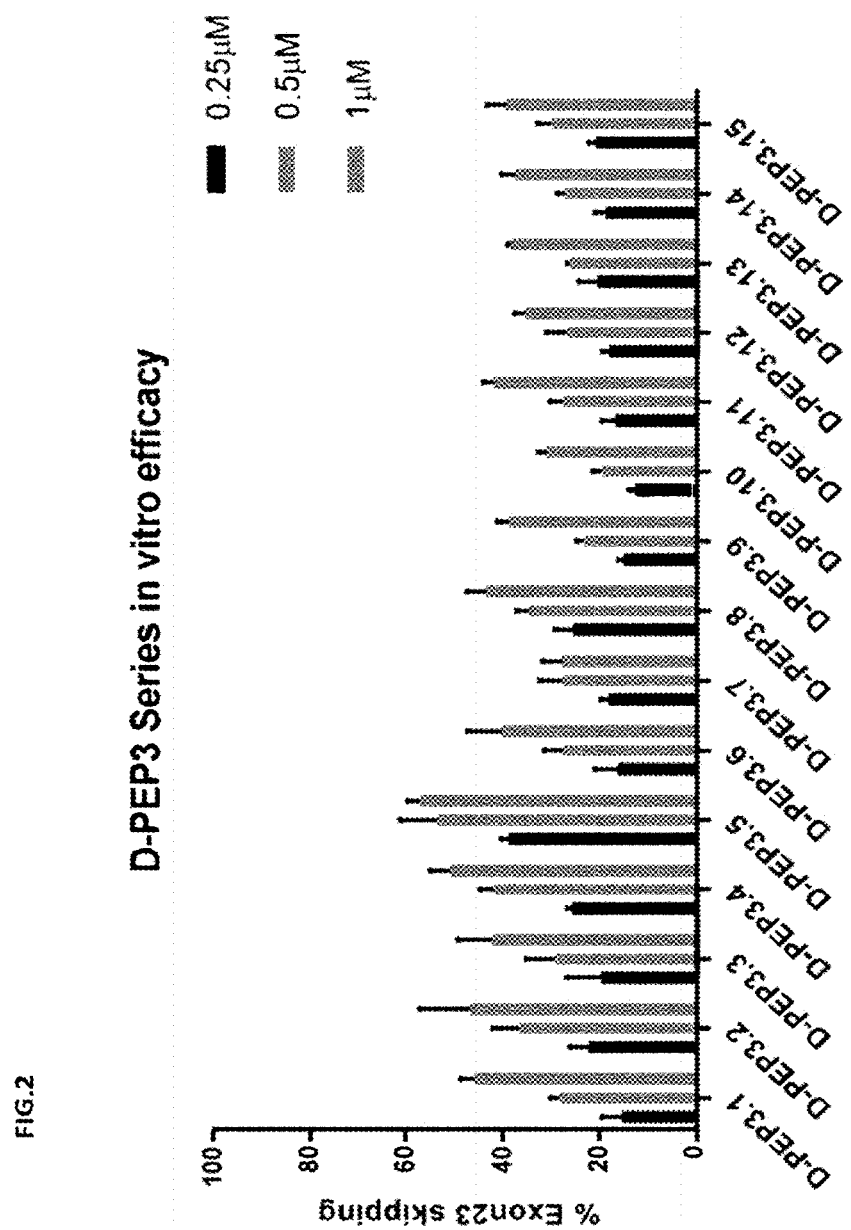
FIG. 2: shows the in vitro exon 23 skipping efficacy of some of the DPEP3 series of peptides conjugated to an antisense therapeutic PMO at 0.25 µM, 0.5 µM and 1 µM in H2K-mdx cells as measured by densitometry analysis of nested RT-PCR (Error bars: standard deviation, n≥3)
Figure 12:
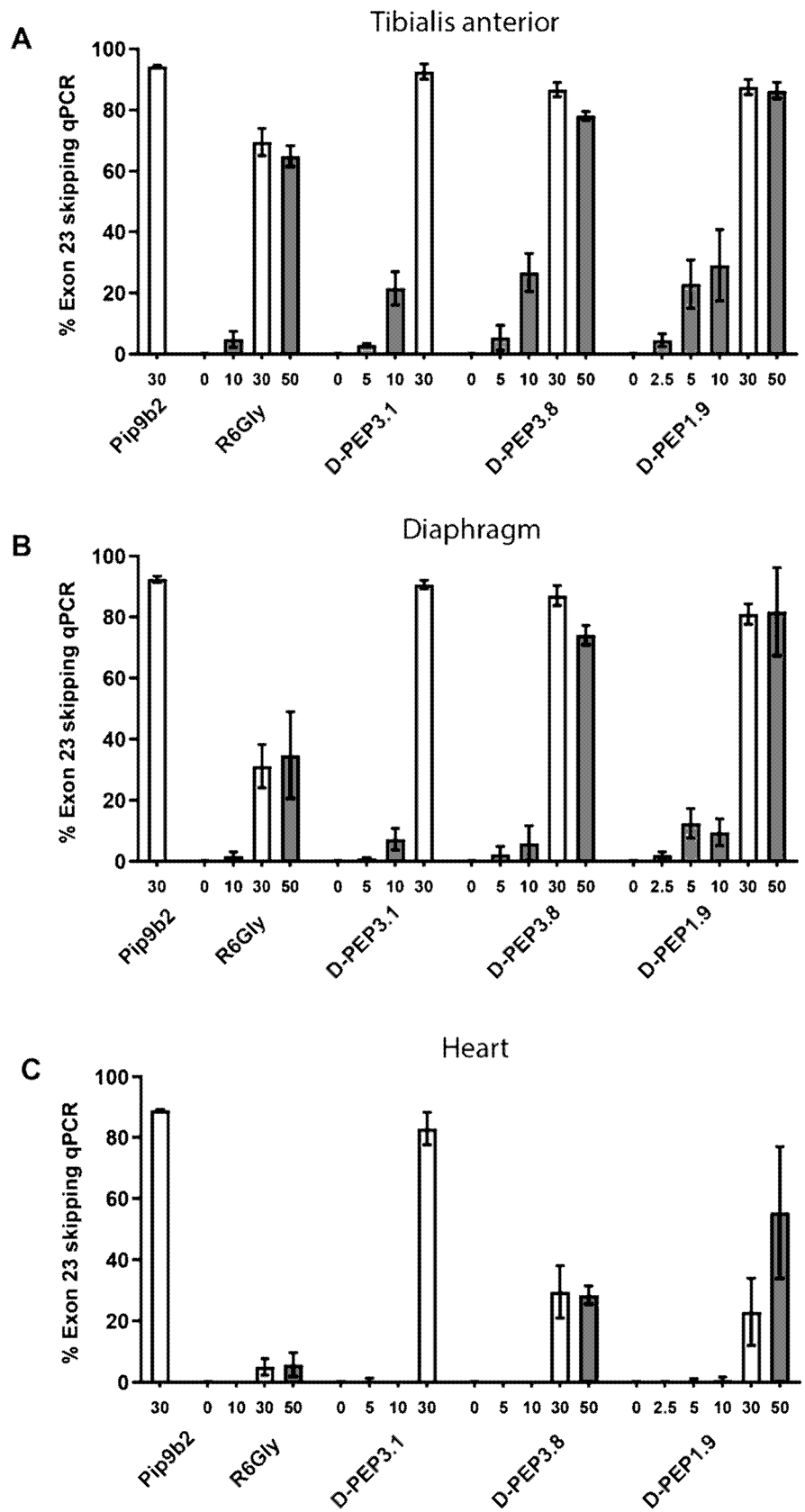
FIG. 12: Dose-response comparative study of in vivo exon skipping efficacy of peptide-PMOs following single dose administration of increasing amounts from 2.5-50 mg/kg to 8-10 week old C57BL6 mice (n=3-6) in comparison with currently available peptide carriers conjugated to the same antisense therapeutic PMO. qPCR analysis of exon 23 exclusion was assessed in (A) tibialis anterior, (B) diaphragm and (C) heart at 7 days post-administration.

The results provided herein demonstrate a clear dose response effect of the peptide-PMO conjugates generated herein in exon skipping activity within cells (FIGS. 1, 2, and 12). These figures also highlight that all of the DPEP1 and DPEP3 series, i.e. the peptides of the invention, have sufficient cell penetrating efficacy in cells to be considered for therapeutic use.

Figure 3:
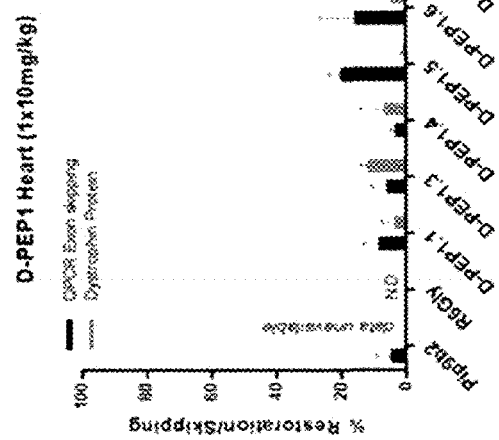
FIG. 3: shows the in vivo efficacy of some of the DPEP1 series of peptides conjugated to an antisense therapeutic PMO in (A) Tibalis anterior muscle, (B) diaphragm, and (C) heart muscle following a single 10 mg/kg intravenous dose into mdx mice measured by western blot and qRT-PCR (Error bars: standard deviation, n=3)
Figure 3:
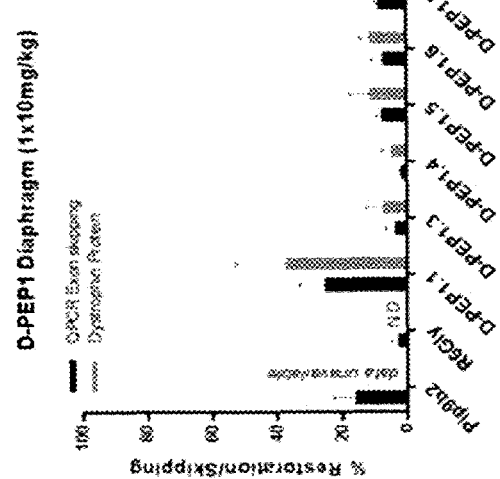
Figure 3:
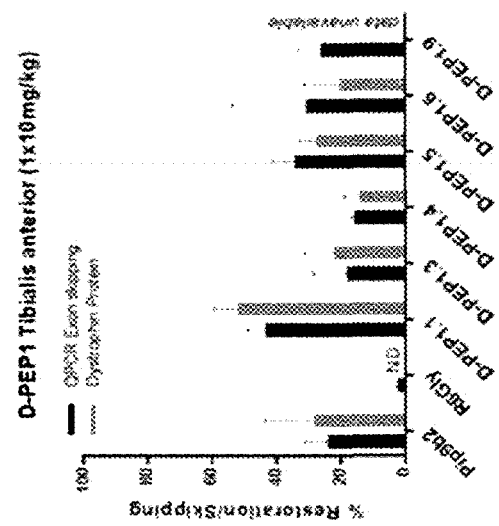
Figure 4:
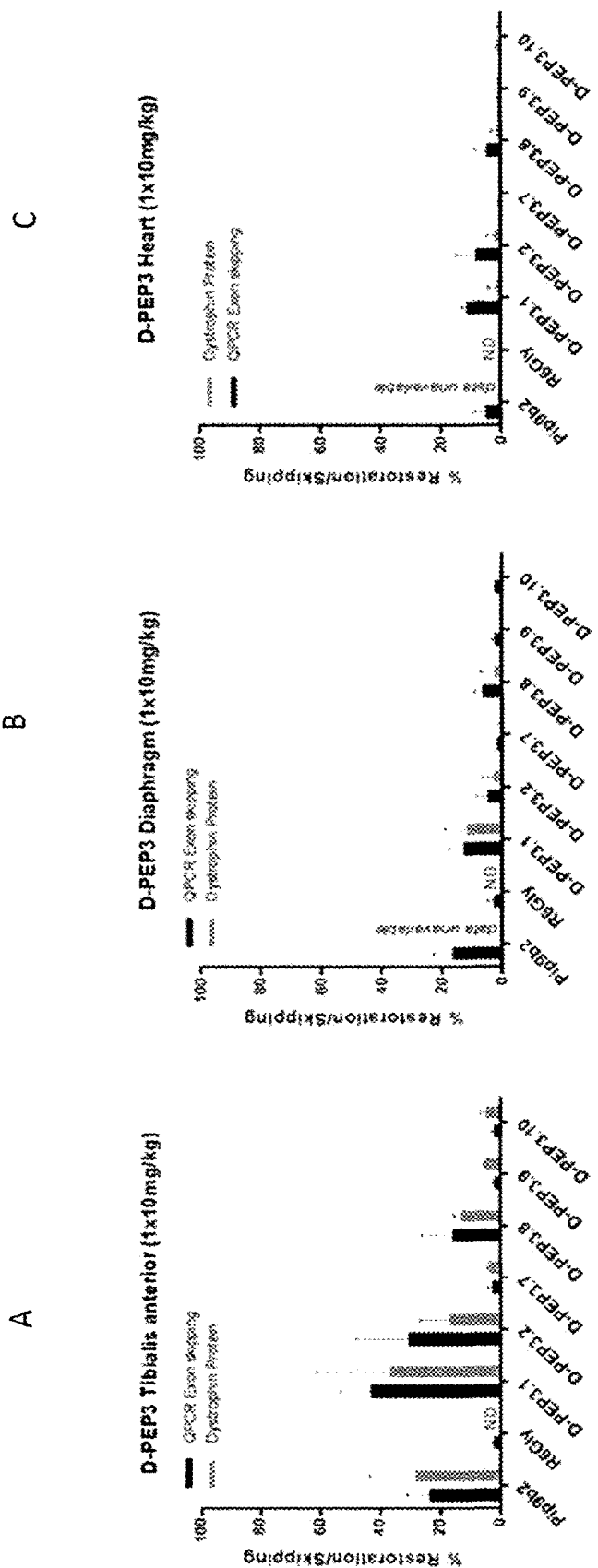
FIG. 4: shows the in vivo efficacy of some of the DPEP3 series of peptides conjugated to an antisense therapeutic PMO in (A) Tibalis anterior muscle, (B) diaphragm, and (C) heart muscle following a single 10 mg/kg intravenous dose into mdx mice measured by western blot and qRT-PCR (Error bars: standard deviation, n=3)

The results provided herein further highlight the activity of the peptide-PMO conjugates in vivo in a relevant mouse model of disease (FIGS. 3-4). Overall the results suggest that activity of such conjugates is greatest in tibialis anterior>diaphragm>heart. These figures demonstrate that the DPEP peptide conjugates of the invention have good exon skipping activity in vivo and provide an increase in dystrophin protein expression in vivo. Furthermore, the DPEP conjugates of the invention compare favourably in both respects with previous cell-penetrating peptides, such as 'PIP' peptides and R6Gly, when used in the same conjugate.

Figure 5:
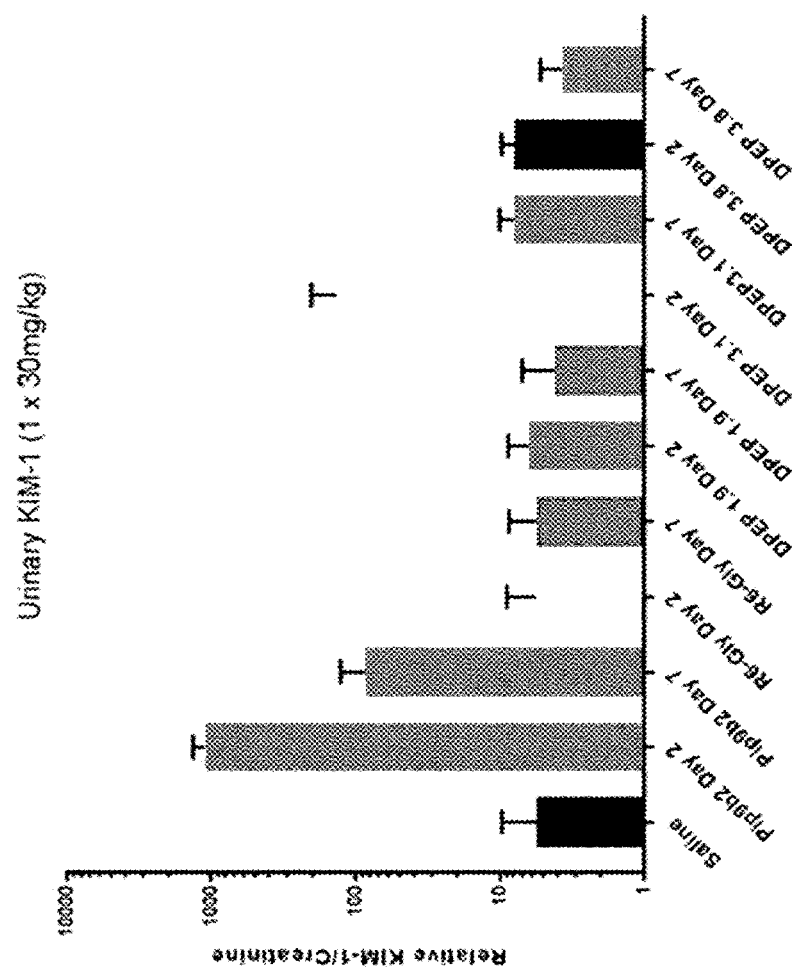
FIG. 5: shows the relative KIM-1 levels measured in the urine of C57BL/6 mice 2 days and 7 days after administration of a single dose of 30 mg/kg of various DPEP peptides conjugated to an antisense therapeutic PMO, in comparison with currently available peptide carriers conjugated to the same antisense therapeutic PMO and saline (Error bars: standard deviation, n=6)
Figure 6:
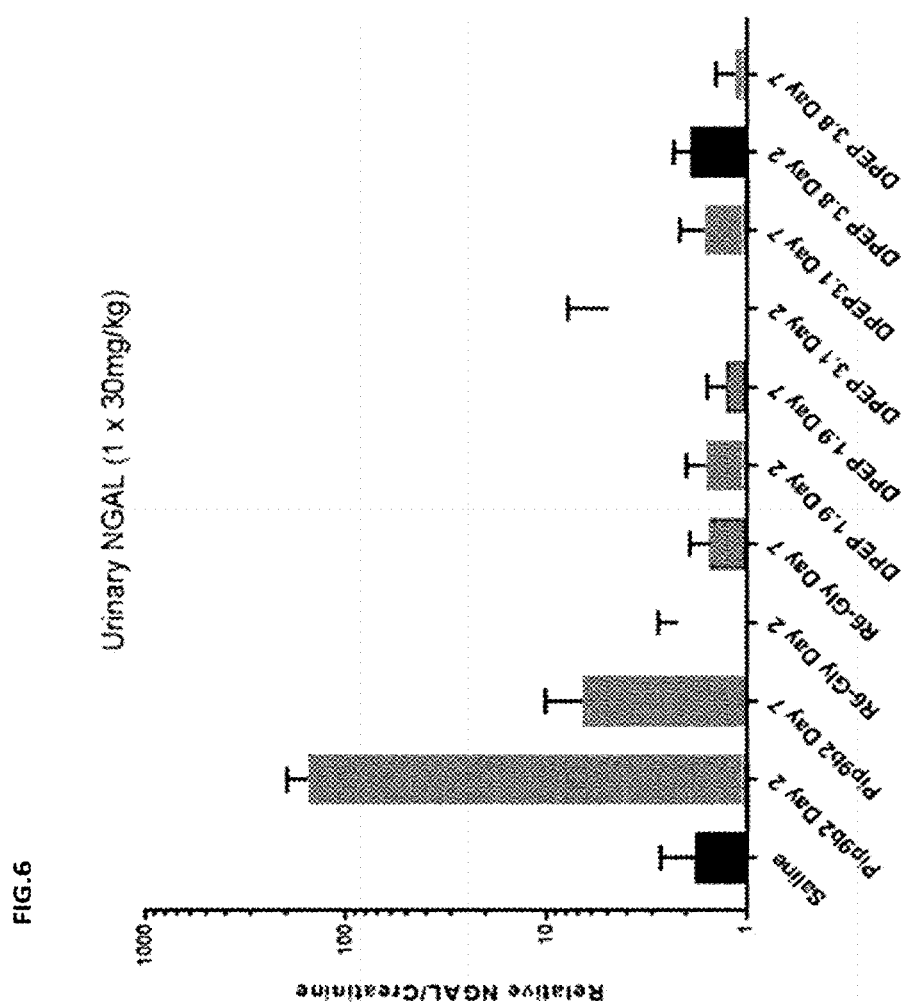
FIG. 6: shows the relative NGAL levels measured in the urine of C57BL/6 mice 2 days and 7 days after administration of a single dose of 30 mg/kg of various DPEP peptides conjugated to an antisense therapeutic PMO, in comparison with currently available peptide carriers conjugated to the same antisense therapeutic PMO and saline (Error bars: standard deviation, n=6)
Figure 7:
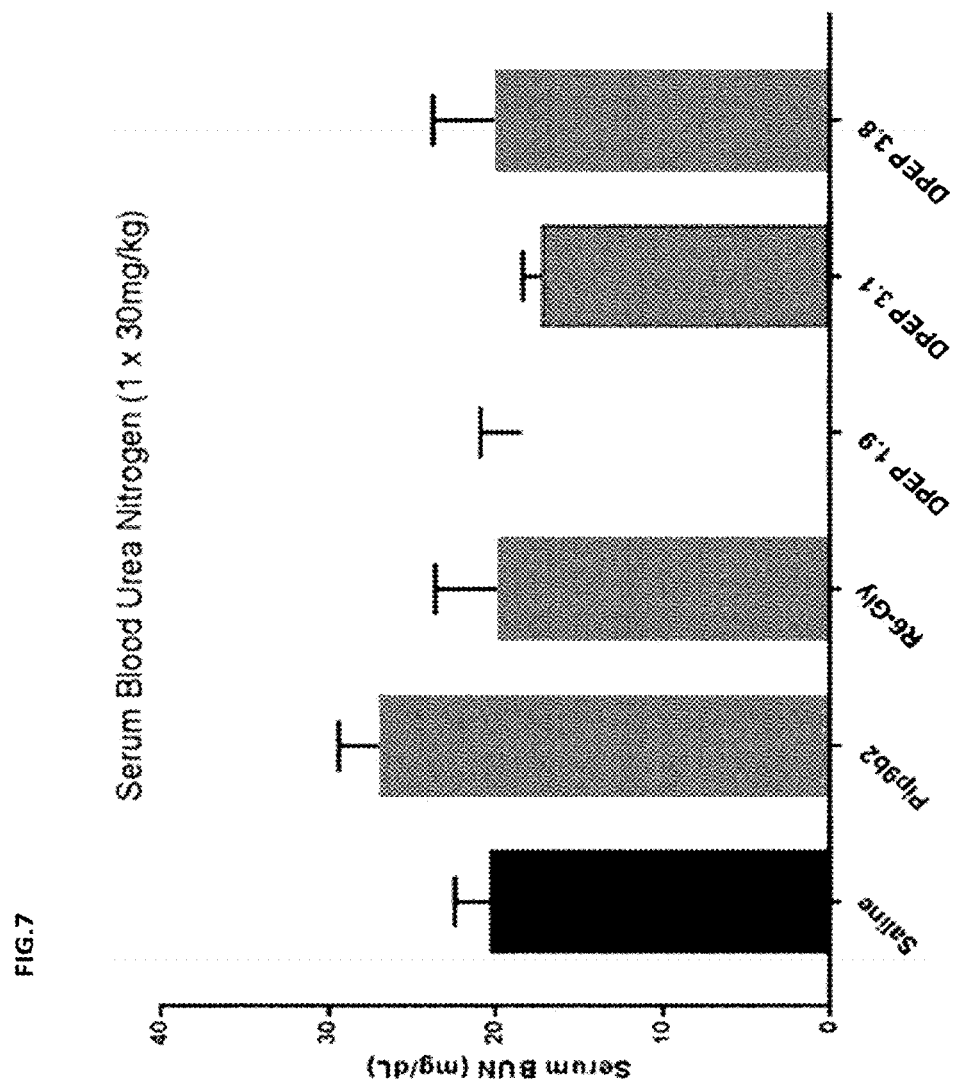
FIG. 7: shows the BUN serum levels measured in C57BL/6 mice 7 days after administration of a single dose of 30 mg/kg of various DPEP peptides conjugated to an antisense therapeutic PMO, in comparison with currently available peptide carriers conjugated to the same antisense therapeutic PMO and saline (Error bars: standard deviation, n=6)
Figure 8:
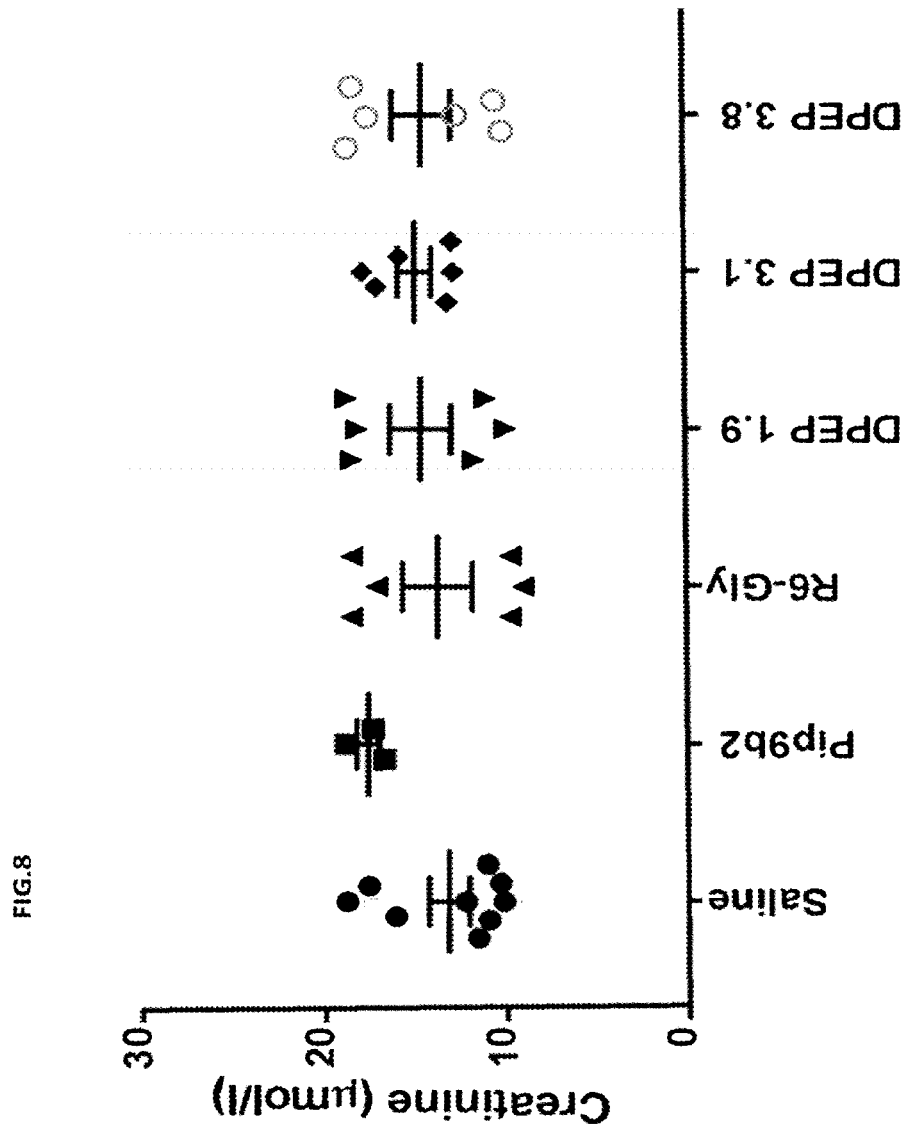
FIG. 8: shows the Creatinine serum levels measured in C57BL/6 mice 7 days after administration of a single dose of 30 mg/kg of various DPEP peptides conjugated to an antisense therapeutic PMO, in comparison with currently available peptide carriers conjugated to the same antisense therapeutic PMO and saline (Error bars: standard deviation, n=6)
Figure 9:
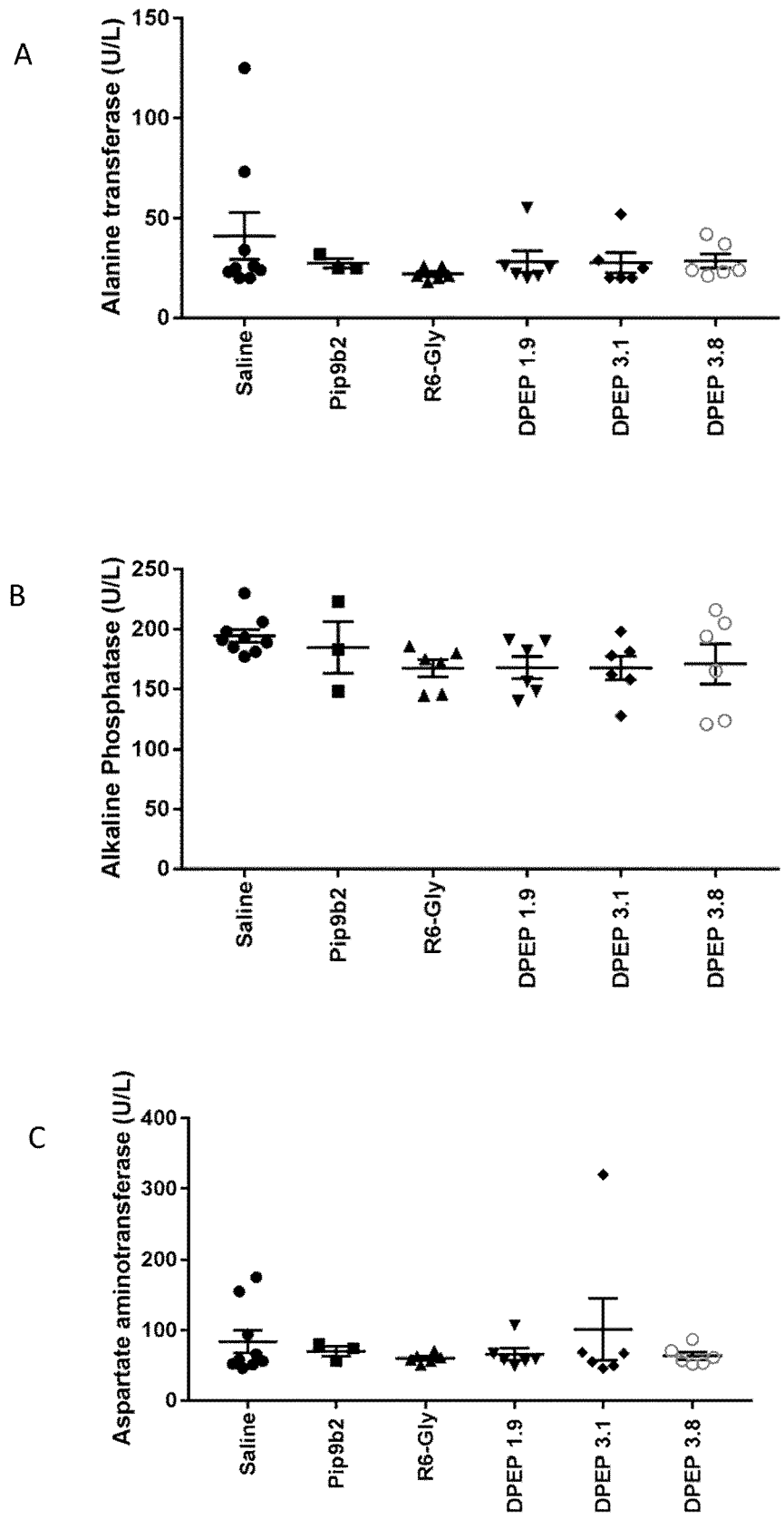
FIG. 9: shows the (A) Alanine Transferase, (B) Alkaline Phosphatase and (C) aspartate aminotransferase serum levels measured in C57BL/6 mice 7 days after administration of a single dose of 30 mg/kg of various DPEP peptides conjugated to an antisense therapeutic PMO, in comparison with currently available peptide carriers conjugated to the same antisense therapeutic PMO and saline (Error bars: standard deviation, n=6)
Figure 11:
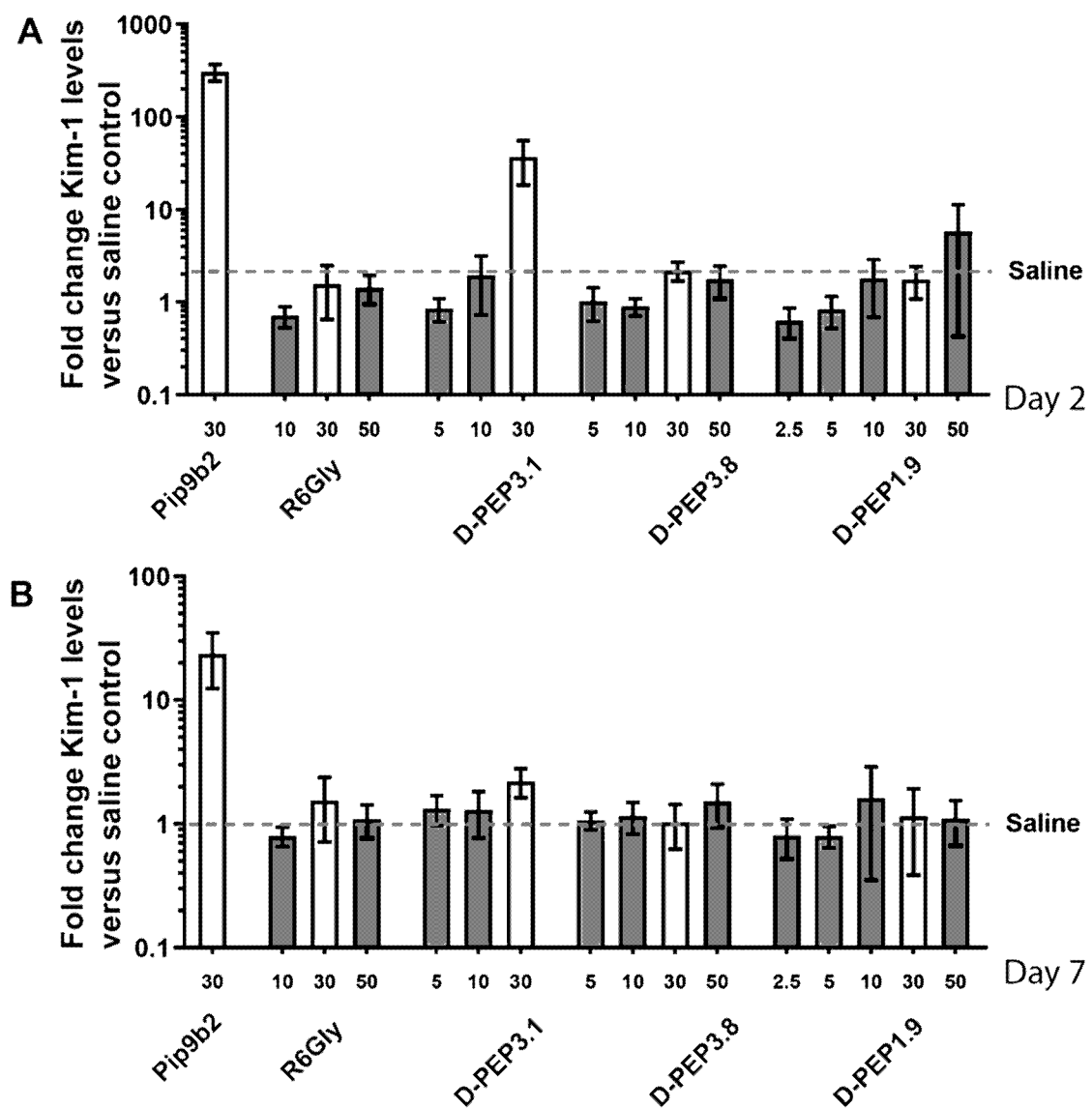
FIGS. 11 A and B: Assessment of urinary KIM-1 levels at Day 2 or Day 7 following single dose administration of different amounts of peptide-PMOs between 2.5-50 mg/kg to 8-10 week old C57BL6 mice (n=4-6) in comparison with a currently available peptide carriers conjugated to the same antisense therapeutic PMO. KIM-1 levels were determined by ELISA and normalised to urinary creatinine levels. Data is presented as fold-change over saline injected mice control KIM-1 levels (n=10).

Also demonstrated herein is that the levels of KIM-1 and NGAL (which are indicators of nephrotoxicity) after administration of the DPEP peptide conjugate compounds are all significantly lower than conjugates with previous cell-penetrating peptides. DPEP 1.9 and 3.8 conjugates demonstrated the lowest levels of such markers (FIGS. 5, 6 and 11). Serum blood urea nitrogen levels (another marker of kidney dysfunction) are also only elevated for conjugates with Pip9b2 and not for conjugates with the DPEP peptides of the invention (FIG. 7). The second main finding is that seven days following administration, KIM-1 and NGAL levels are reduced to near saline levels for all DPEP peptide conjugates which suggests that there is also some reversal and improvement of kidney-related toxicity. No such effect was seen with conjugates using previous cell-penetrating peptides. This effect of reversal of toxicity is still seen with the DPEP peptides of the invention when given at high doses of 50 mg/kg (FIG. 11). Prior cell penetrating peptides showed no decrease in toxicity after 7 days, and remained much higher in toxic markers throughout.

Figure 10:
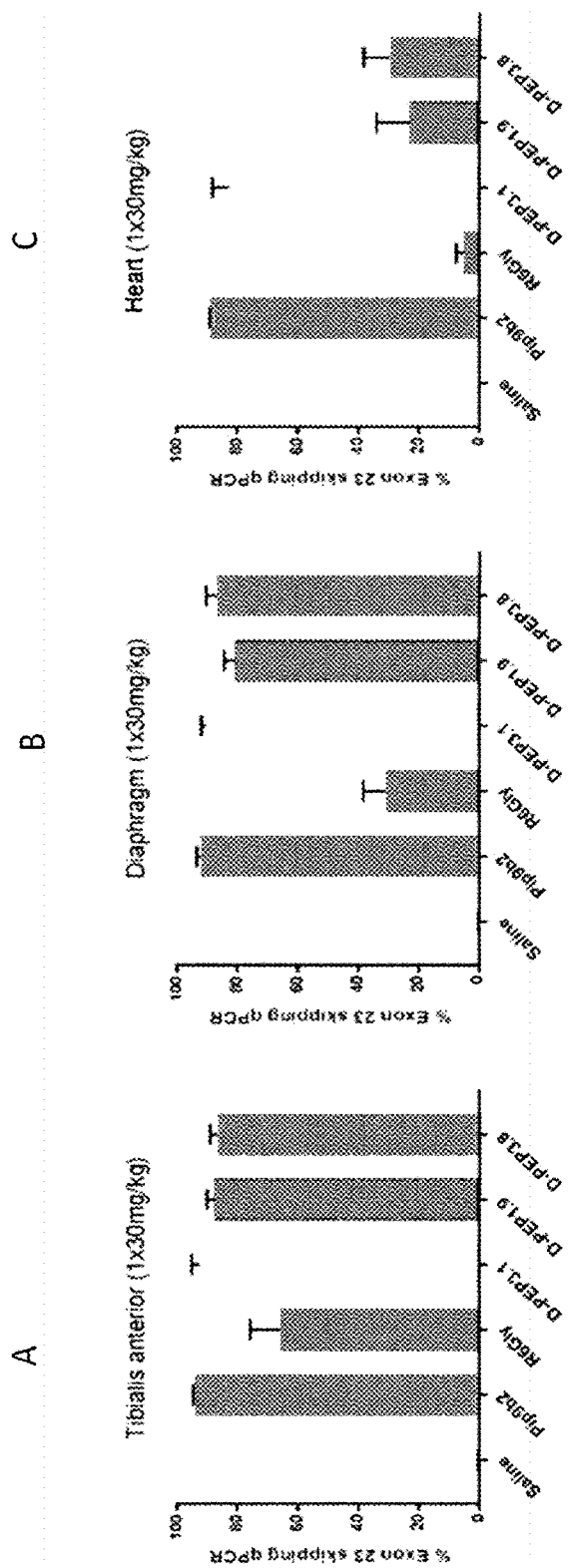
FIG. 10: shows the in vivo efficacy of exon 23 skipping assessed by qRT-PCR in (A) tibalis anterior, (B) diaphragm and (C) heart of C57BL/6 mice following a single 30 mg/kg intravenous administration of various DPEP peptides conjugated to an antisense therapeutic PMO, in comparison with currently available peptide carriers conjugated to the same antisense therapeutic PMO and saline.

Further demonstrated is that exon skipping activity remains high for all of the DPEP peptide conjugates in TA and diaphragm (FIGS. 10 and 12) at higher doses of 30 and 50 mg/kg, which when corroborated with the reduced levels of kidney damage markers, suggests a wider therapeutic index for these compounds because toxicity markers are many-fold lower. It is also notable that all of the DPEP peptide conjugates have higher activity than the known R6Gly comparator in a conjugate, whilst at least maintaining similar levels of toxicity markers, and similar activity to the known PIP peptide comparator in a conjugate whilst having much lower levels of toxicity markers. In some cases, the DPEP peptide conjugates of the invention display not only increased activity compared to the known R6Gly conjugate but also reduced toxicity markers.

Therefore, the DPEP1 and 3 peptides of the invention provide promising cell-penetrating peptides for improving the efficacy and reducing the toxicity of therapeutic conjugates for the treatment of neuromuscular disorders in humans.

3. Further Examples

P-PMO Synthesis and Preparation

9-Fluroenylmethoxycarbonyl (Fmoc) protected L-amino acids, benzotriazole-1-yl-oxy-tris-pyrrolidino-phosphonium (PyBOP), 2-(1H-benzotriazole-1-yl)-1,1,3,3-tetramethyl-uronium hexafluorophosphate (HBTU), and the Fmoc-β-Ala-OH preloaded Wang resin (0.19 or 0.46 mmol g−1) were obtained from Merck (Hohenbrunn, Germany). 1-Hydroxy-7-azabenzotriazole (HOAt) was obtained from Sigma-Aldrich. HPLC grade acetonitrile, methanol and synthesis grade N-methyl-2-pyrrolidone (NMP) were purchased from Fisher Scientific (Loughborough, UK).

Peptide synthesis grade N,N-dimethylformamide (DMF) and diethyl ether were obtained from VWR (Leicestershire, UK). Piperidine and trifluoroacetic acid (TFA) were obtained from Alfa Aesar (Heysham, England). PMO was purchased from Gene Tools Inc. (Philomath, USA). All other reagents were obtained from Sigma-Aldrich (St. Louis, Mo., USA) unless otherwise stated. MALDI-TOF mass spectrometry was carried out using a Voyager DE Pro BioSpectrometry workstation. A stock solution of 10 mg mL-1 of α-cyano-4-hydroxycinnamic acid or sinapinic acid in 50% acetonitrile in water was used as matrix. Error bars are ±0.1%.

Synthesis of P-PMO Peptides for Screening in Cells a) Preparation of a Library of Peptide Variants Peptides were either prepared on a 10 μmol scale using an Intavis Parallel Peptide Synthesizer or on a 100 μmol scale using a CEM Liberty Blue™ Peptide Synthesizer (Buckingham, UK) using Fmoc-β-Ala-OH preloaded Wang resin (0.19 or 0.46 mmol g−1, Merck Millipore) by applying standard Fmoc chemistry and following manufacturer's recommendations. In the case of synthesis using the Intavis Parallel Peptide Synthesizer, double coupling steps were used with a PyBOP/NMM coupling mixture followed by acetic anhydride capping after each step. For synthesis using the CEM Liberty Blue Peptide Synthesizer, single standard couplings were implemented for all amino acids except arginine, which was performed by double couplings. The coupling was carried out once at 75° C. for 5 min at 60-watt microwave power except for arginine residues, which were coupled twice each. Each deprotection reaction was carried out at 75° C. twice, once for 30 sec and then for 3 min at 35-watt microwave power. Once synthesis was complete, the resin was washed with DMF (3×50 mL) and the N-terminus of the solid phase bound peptide was acetylated with acetic anhydride in the presence of DIPEA, at room temperature. After acetylation of the N-terminus, the peptide resin was washed with DMF (3×20 mL) and DCM (3×20 mL). The peptides were cleaved from the solid support by treatment with a cleavage cocktail consisting of trifluoroacetic acid (TFA):H2O:triisopropylsilane (TIPS) (95%: 2.5%: 2.5%: 3-10 mL) for 3 h at room temperature. After peptide release, excess TFA was removed by sparging with nitrogen. The crude peptide was precipitated by the addition of cold diethyl ether (15-40 mL depending on scale of the synthesis) and centrifuged at 3200 rpm for 5 min. The crude peptide pellet was washed thrice with cold diethyl ether (3×15 mL) and purified by RP-HPLC using a Varian 940-LC HPLC System fitted with a 445-LC Scale-up module and 440-LC fraction collector. Peptides were purified by semi-preparative HPLC on an RP-C18 column (10×250 mm, Phenomenex Jupiter) using a linear gradient of CH3CN in 0.1% TFA/H2O with a flow rate of 15 mL min-1. Detection was performed at 220 nm and 260 nm. The fractions containing the desired peptide were combined and lyophilized to yield the peptide as a white solid (see Table 5 for yields).

TABLE 5 peptides as synthesised for testing in the examples with N-terminal acetylation (Ac), C-terminal β-alanine linker (B), S* is a glucosylated serine residue. DPEP5.7, Pip9b2, and Pip6a are comparative peptides.

| Peptide Number | Sequence ID NO. incorporated | Sequence Tested (with additional C and N terminal modifications) |
|---|---|---|
| D-PEP 1.1 | 27 | Ac-RBRRBRRFQILYRBRBR-B |
| D-PEP 1.7 | 33 | Ac-RBRRBRFQILYRBRBR-B |
| D-PEP 1.8 | 34 | Ac-RBRRBFQILYRBRRBR-B |
| D-PEP 1.9 | 35 | Ac-RBRRBRFQILYBRBR-B |
| D-PEP 1.9W3 | 104 | Ac-RBRRBRWWWBRBR-B |
| DPEP 1.9W4P | 105 | Ac-RBRRBRWWPWWBRBR-B |
| D-PEP 3.1 | 37 | Ac-RBRRBRRFQILYRBHBH-B |
| D-PEP 3.8 | 44 | Ac-RBRRBRFQILYRBHBH-B |
| D-PEP 5.70 | 106 | Ac-RBRBRS*RBRBR-B |
| Pip6a | 112 | Ac-RXRRBRRXR-YQFLI-RXRBRXR-B |
| Pip9b2 | 113 | Ac-RXRRBRR-FQILY-RBRXR-B | b) Synthesis of a Library of Peptide-PMO Conjugates

A 21-mer PMO antisense sequence for triplet repeat sequences (CAGCAGCAGCAGCAGCAGCAG (SEQ ID NO.107) otherwise known as [CAG]7 was used. The peptide was conjugated to the 3'-end of the PMO through its C-terminal carboxyl group. This was achieved using 2.5 and 2 equivalents of PyBOP and HOAt in NMP respectively in the presence of 2.5 equivalents of DIPEA and 2.5 fold excess of peptide over PMO dissolved in DMSO was used. In general, to a solution of peptide (2500 nmol) in N-methylpyrrolidone (NMP, 80 µL) were added PyBOP (19.2 µL of 0.3 M in NMP), HOAt in (16.7 µl of 0.3 M NMP), DIPEA (1.0 mL) and PMO (180 µL of 10 mM in DMSO). The mixture was left for 2.5 h at 40° C. and the reaction was quenched by the addition of 0.1% TFA in H₂O (300 µL). This solution was purified by Ion exchange chromatography using a converted Gilson HPLC system. The PMO-peptide conjugates were purified on an ion exchange column (Resource S 4 mL, GE Healthcare) using a linear gradient of sodium phosphate buffer (25 mM, pH 7.0) containing 20% CH3CN. A sodium chloride solution (1 M) was used to elute the conjugate from the column at a flow rate of either 4 mL min-1 or 6 mL min-1. The fractions containing the desired compound were combined desalted immediately. The removal of excess salts from the peptide-PMO conjugate was afforded through the filtration of the fractions collected after ion exchange using an Amicon® ultra-15 3K centrifugal filter device. The conjugate was lyophilized and analyzed by MALDI-TOF. The conjugates were dissolved in sterile water and filtered through a 0.22 µm cellulose acetate membrane before use. The concentration of peptide-PMO was determined by the molar absorption of the conjugates at 265 nm in 0.1 N HCl solution. (see Table 6 for yields).

TABLE 6

Yields of P-PMO conjugates for cell culture analysis and in vivo experiments (The yields are based on dried weight of the lyophilised purified P-PMO. The purity for the P-PMOs is greater than 95% as ascertained by normal phase HPLC at 220 nm and 260 nm.

| Peptide | Yield |
|---|---|
| D-Pep 1.1 | 36% |
| D-Pep 1.7 | 41% |
| D-pep 1.8 | 38% |
| D-Pep 1.9 | 40% |
| D-Pep 1.9W3 | 43% |
| D-Pep 1.9W4P | 23% |
| D-Pep 3.1 | 31% |
| D-Pep 3.8 | 36% |
| D-Pep 5.70 | 31% |

Synthesis of Peptide-PMO Conjugates.

Peptides were synthesized and conjugated to PMO as described previously. The PMO sequence targeting CUG/CTG expanded repeats (5'-CAGCAGCAGCAGCAG CAGCAG-3' (SEQ ID NO: 107)) was purchased from Gene Tools LLC. This is a [CAG]7 PMO as referenced elsewhere herein.

Cell Culture and Peptide-PMO Treatment.

Immortalized myoblasts from healthy individual or DM1 patient with 2600 CTG repeats were cultivated in a growth medium consisting of a mix of M199:DMEM (1:4 ratio; Life technologies) supplemented with 20% FBS (Life technologies), 50 µg/ml gentamycin (Life technologies), 25 µg/ml fetuin, 0.5 ng/ml bFGF, 5 ng/ml EGF and 0.2 µg/ml dexamethasone (Sigma-Aldrich). Myogenic differentiation was induced by switching confluent cell cultures to DMEM medium supplemented with 5 µg/ml insulin (Sigma-Aldrich) for myoblasts. For treatment, WT or DM1 cells are differentiated for 4 days. Then, medium was changed with fresh differentiation medium with peptide-PMO conjugates at a 1, 2, 5 10, 20 or 40 µM concentration. Cells were harvested for analysis 48 h after treatment. Cell viability was quantified in after 2 days of transfection of peptide-PMOs at 40 uM in human hepatocytes or at a 1, 2, 5 10, 20 or 40 µM concentration in human myoblasts using a fluorescent-based assay (Promega).

RNA Isolation, RT-PCR and qPCR Analysis.

For mice tissues: prior to RNA extraction, muscles were disrupted in TriReagent (Sigma-Aldrich) using Fastprep system and Lysing Matrix D tubes (MP biomedicals). For human cells: prior to RNA extraction, cells were lysed in a proteinase K buffer (500 mM NaCl, 10 mM Tris-HCl, pH 7.2, 1.5 mM MgCl2, 10 mM EDTA, 2% SDS and 0.5 mg/ml of proteinase K) for 45 min at 55° C. Total RNAs were isolated using TriReagent according to the manufacturer's protocol. One microgram of RNA was reverse transcribed using M-MLV first-strand synthesis system (Life Technologies) according to the manufacturer's instructions in a total of 20 µL. One microliter of cDNA preparation was subsequently used in a semi-quantitative PCR analysis according to standard protocol (ReddyMix, Thermo Scientific). PCR amplification was carried out for 25-35 cycles within the linear range of amplification for each gene. PCR products were resolved on 1.5-2% agarose gels, ethidium bromide-stained and quantified with ImageJ software. The ratios of exon inclusion were quantified as a percentage of inclusion relative to total intensity of isoform signals. Primers are shown in the following table 7:

TABLE 7 primers for PCR

| Primer Name | SEQ ID NO. | Species/ Gene/Exon | Sequence (5'-3') |
|---|---|---|---|
| Mbnl1.F | 108 | Mouse-Human/ mbnl1/exon5 | GCTGCCCAATACCAGGTCAAC |
| Mbnl1.R | 109 | Mouse-Human/ mbnl1/exon5 | TGGTGG-GAGAAATGCTGTATGC |
| DMD.F | 110 | Human/DMD/ exon78 | TTAGAGGAGGTGATGGAGCA |
| DMD.R | 111 | Human/DMD/ exon78 | GATACTAAGGACTCCATCGC |

Toxicology

Toxicology Assessments were Performed as Described Above in Section 1.10.

Results

Figure 13:
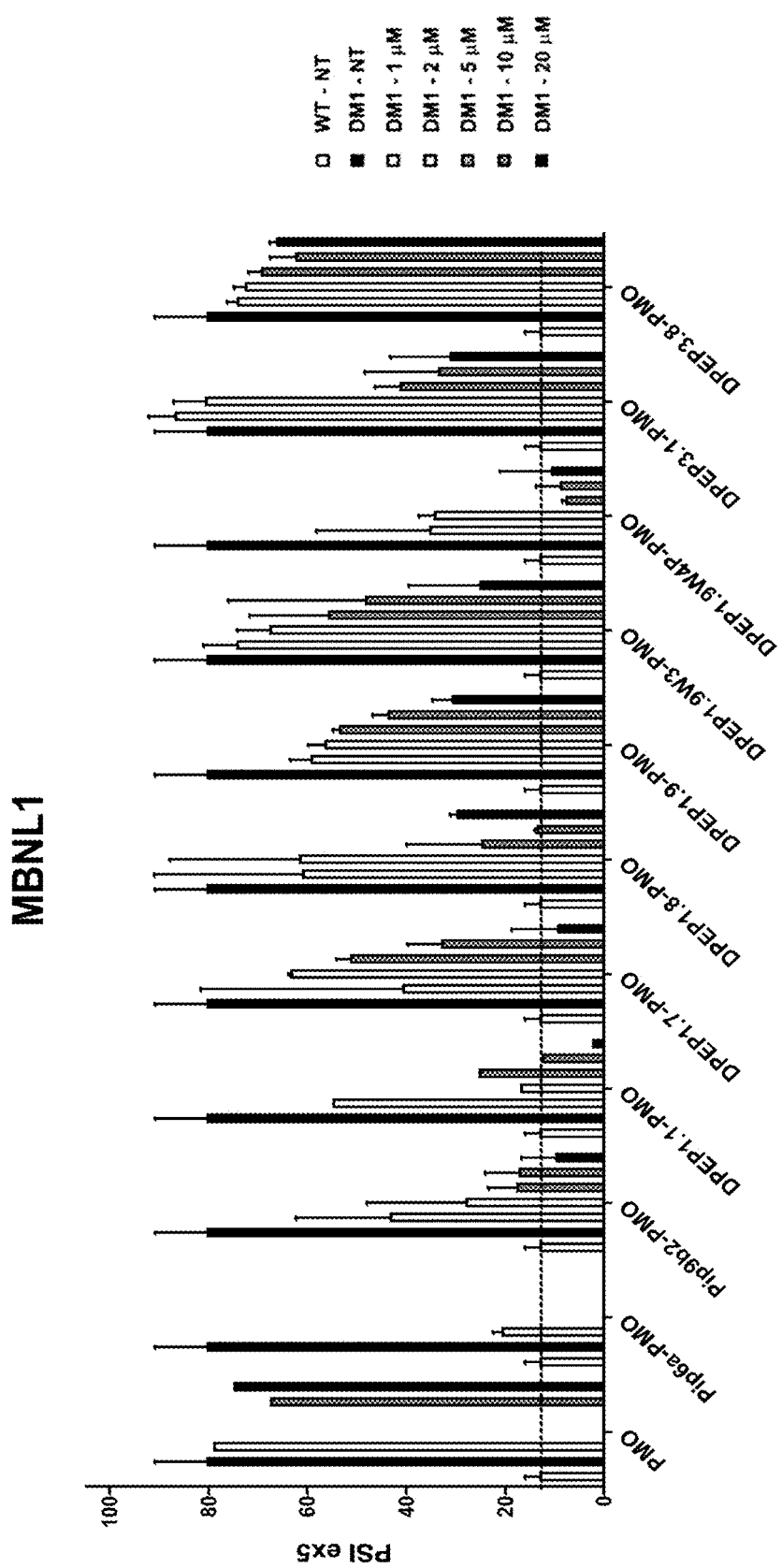
FIG. 13: shows different DPEP1/3-[CAG]$_7$PMO conjugates correct splicing defects of Mbnl1 transcripts in vitro in DM1 patient myoblasts derived from DM1 patients with 2600 repeats in the DMPK gene at various concentrations (n=1-3)
Figure 14:
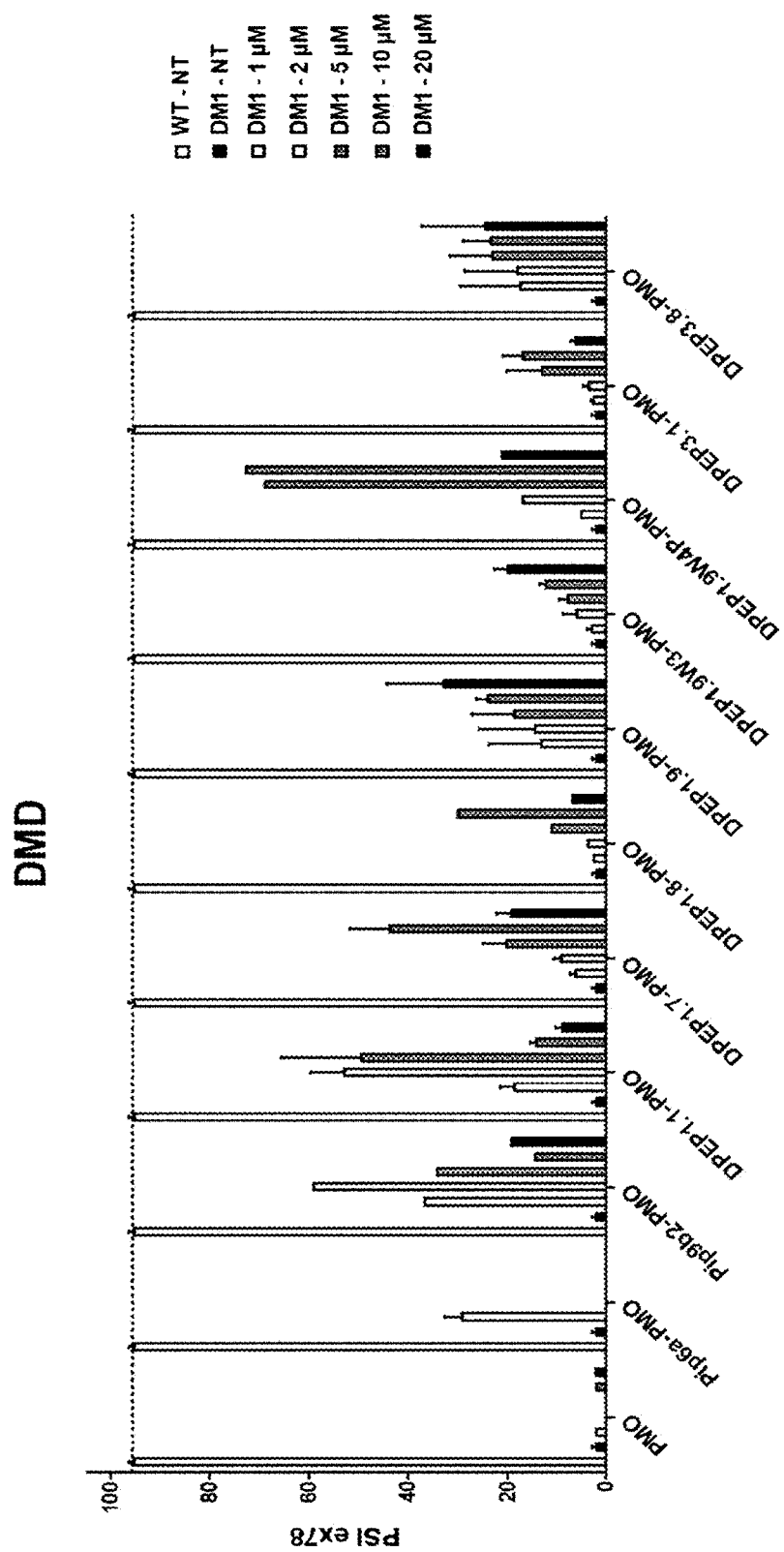
FIG. 14: shows different DPEP1/3-[CAG]$_7$PMO conjugates correct splicing defects of DMD transcripts in vitro in DM1 patient myoblasts derived from DM1 patients with 2600 repeats in the DMPK gene at various concentrations (Error bars: mean±SEM, n=1-3)
Figure 15:
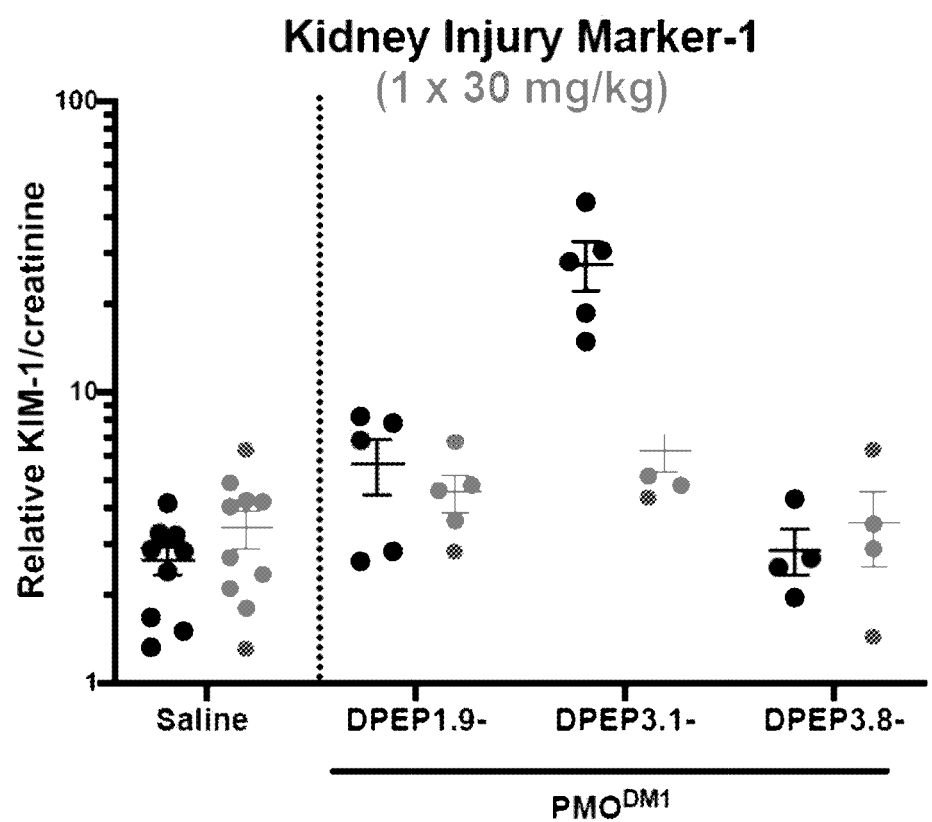
FIG. 15: shows the relative KIM-1 levels assessed in urine from Day 2 and Day 7 post-injection of different DPEP1/3-[CAG]$_7$ PMO conjugates in C57BL6 female mice measured by ELISA with samples diluted to fit within standard curve. Values were normalised to urinary creatinine levels to account for urine protein concentration. KIM-1 levels were similar to saline control injections in comparison to the fold increases induced by the prior Pip series of peptide carriers (Error bars: mean±SEM, n=4-10)
Figure 16:
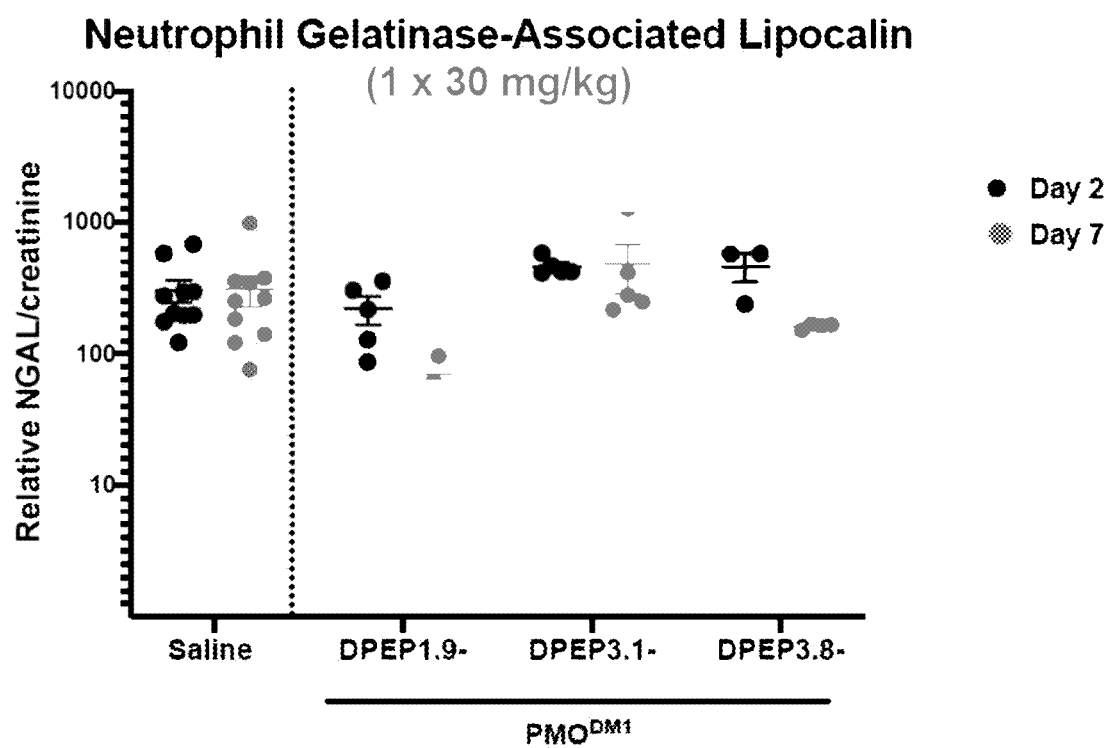
FIG. 16: shows the relative NGAL levels measured in the urine from Day 2 and Day 7 post-injection of different DPEP1/3-[CAG]$_7$ PMO conjugates in C57BL6 female mice measured by ELISA with samples diluted to fit within standard curve. Values were normalised to urinary creatinine levels to account for urine protein concentration. NGAL levels were similar to saline control injections in comparison to the fold increases induced by the prior Pip series of peptide carriers (Error bars: mean±SEM, n=4-10)
Figure 17:
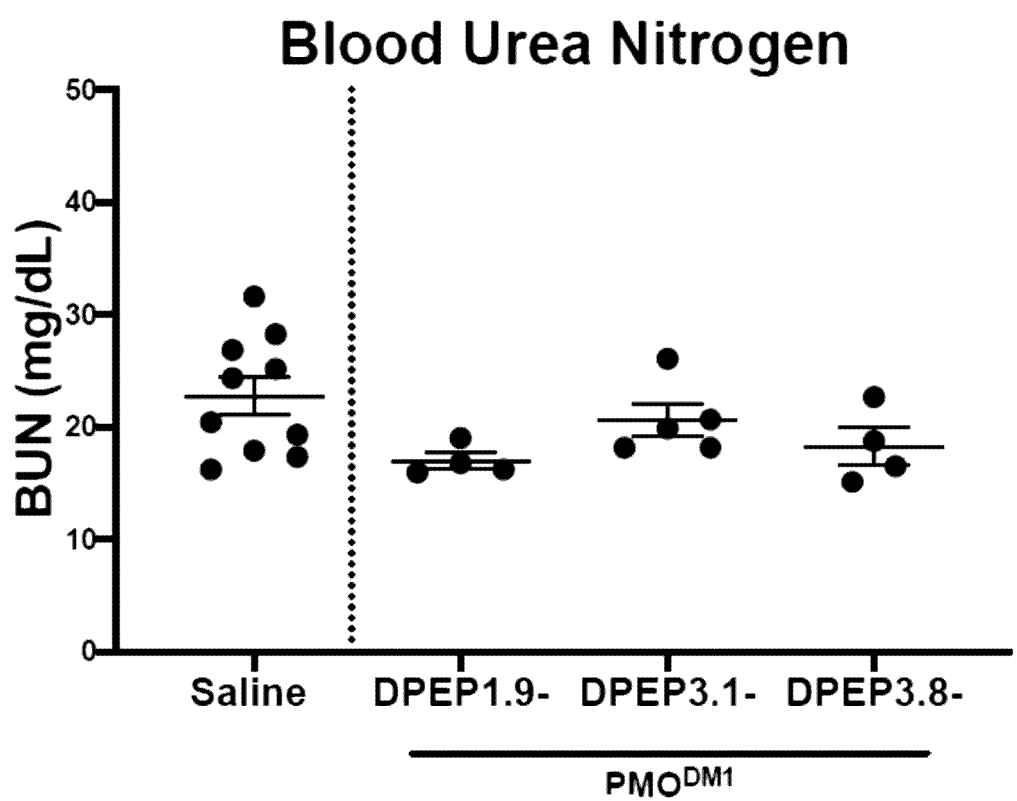
FIG. 17: shows the BUN levels assessed in serum from Day 7 post-injection of different DPEP1/3-[CAG]$_7$ PMO conjugates in C57BL6 female mice compared to saline. BUN levels were similar to saline control injections in comparison to the fold increases induced by prior Pip series of peptide carriers (Error bars: mean±SEM, n=4-10)
Figure 18:
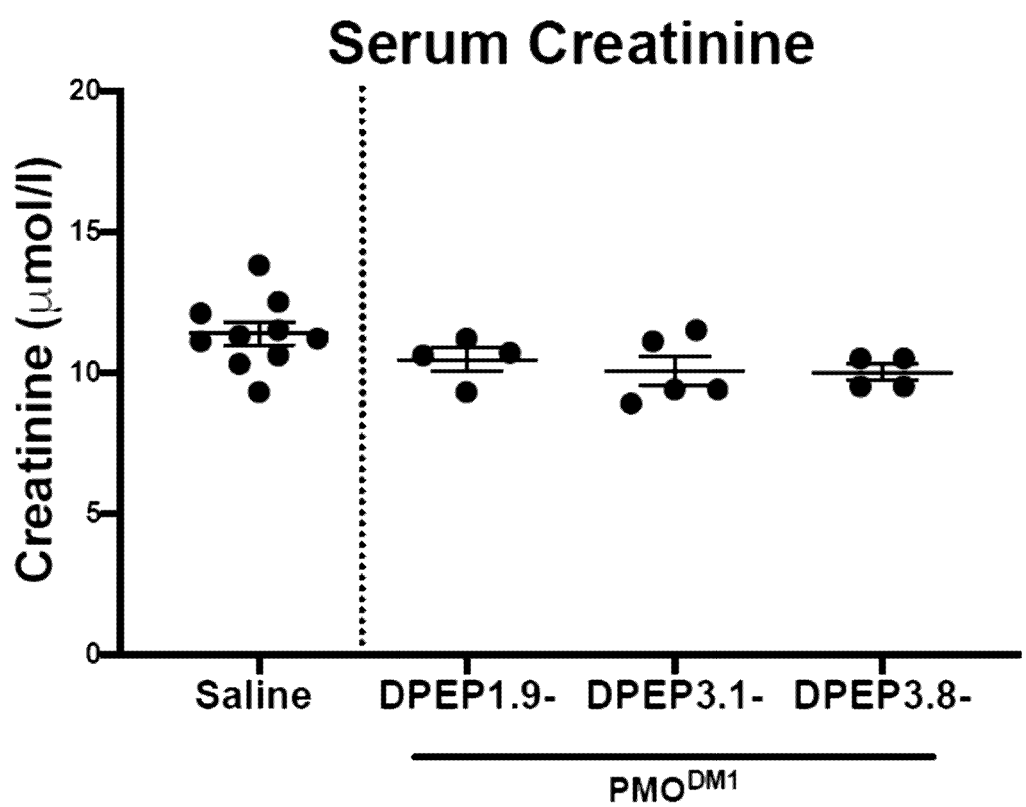
FIG. 18: shows the creatinine levels assessed in serum from Day 7 post-injection of different DPEP1/3-[CAG]$_7$ PMO conjugates in C57BL6 female mice compared to saline. Creatinine levels were similar to saline control injections in comparison to the fold increases induced by prior Pip series of peptide carriers (Error bars: mean±SEM, n=4-10)
Figure 19:
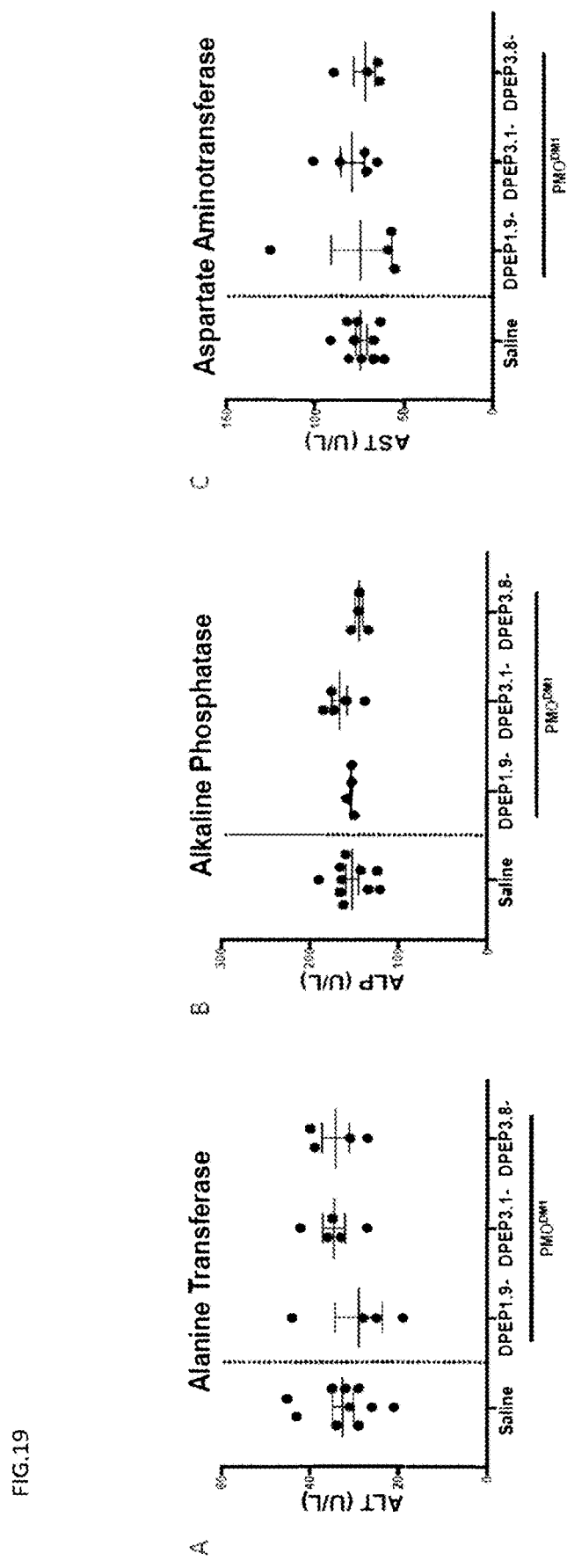
FIG. 19: shows the (A) alanine transferase (ALT), (B) alkaline phosphatase (ALP) and (C) aspartate aminotransferase (AST) levels assessed in serum from C57BL6 female mice, who were administered by bolus IV (tail vein) injection of different DPEP1/3-[CAG]$_7$ PMO conjugates, at day 7 post-injection collection compared to saline. ALP, ALT, AST levels were similar to saline control injections in comparison to the fold increases induced by the prior Pip series of peptide carriers.

The treated DM1 patient derived muscle cells (myoblasts) showed that the DPEP 1 or 3 peptide-[CAG]$_7$ PMO conjugates specifically target mutant CUGexp-DMPK transcripts to abrogate the detrimental sequestration of MBNL1 splicing factor by nuclear RNA foci and consequently MBNL1 functional loss, responsible for splicing defects and muscle dysfunction. The DPEP1/3 peptide-[CAG]$_7$ PMO conjugates penetrate cells and induce splicing normalisation with high efficacy (FIG. 13). These new generation of so called DPEP1 and DPEP3' peptides have shown high efficacy in correcting splicing defects in vitro when conjugated to a CAG7 repeat antisense oligonucleotide PMO, indicating potential therapeutic use for treatment of DM1.

Furthermore, the preliminary toxicology evaluation of conjugates formed with DPEP1/3 indicate that ALP, ALT, AST, KIM-1, BUN, NGAL, and creatinine levels were similar to saline control injections, in contrast to the fold increases typically induced by currently available peptide carriers from the Pip series. With this preliminary data we showed that conjugates formed from DPEP peptides with a [CAG]$_7$ PMO are as active as conjugates formed with prior peptides such as Pip6a yet have wider therapeutic window because they are less toxic (FIGS. 15-19).

The invention claimed is:

1. A cell-penetrating peptide consisting of the amino acid sequence

RBRRBRRFQILYRBRBR, (SEQ ID NO: 27)

RBRRBRRYQFLIRBRBR, (SEQ ID NO: 31)

RBRRBRRILFQYRBRBR, (SEQ ID NO: 32)

RBRRBRFQILYBRBR, (SEQ ID NO: 35)

RBRRBRRFQILYRBHBH, (SEQ ID NO: 37)

RBRRBRRFQILYHBHBR, (SEQ ID NO: 38)

RBRRBRFQILYRBHBH, (SEQ ID NO: 44)

RBRRBRFQILYRRBRBR, (SEQ ID NO: 29)

RBRBRFQILYRBRRBRR, (SEQ ID NO: 30)

RBRRBRFQILYRBRBR, (SEQ ID NO: 33)

RBRRBFQILYRBRBR, (SEQ ID NO: 36)

RBRRBRRFQILYHBRBH, (SEQ ID NO: 39)

RBRRBRRYQFLIRBHBH, (SEQ ID NO: 40)

RBRRBRRILFQYRBHBH, (SEQ ID NO: 41)

```
                                            (SEQ ID NO: 42)
    RBRHBHRFQILYRBRBR, (SEQ ID NO: 52)
    RBRRBRRFQILYHBHBH, (SEQ ID NO: 104)
    RBRRBRWWWBRBR, or (SEQ ID NO: 105)
    RBRRBRWWPWWBRBR,
``` wherein B in the amino acid sequences is beta-alanine, and wherein the N-terminus of the cell-penetrating peptide is optionally acetylated, methylated, trifluoroacetylated, trifluoromethylsullfonylated, or methylsulfonylated.

2. The cell-penetrating peptide of claim 1, wherein the N-terminus of the cell-penetrating peptide is acetylated.

3. The cell-penetrating peptide of claim 1, wherein cell-penetrating peptide consists of the amino acid sequence RBRRBRRFQILYRBRBR (SEQ ID NO: 27), wherein the N-terminus of the cell-penetrating peptide is optionally acetylated, methylated, trifluoroacetylated, trifluoromethylsulfonylated, or methylsulfonylated.

4. The cell-penetrating peptide of claim 1, wherein cell-penetrating peptide consists of the amino acid sequence RBRRBRRYQFLIRBRBR (SEQ ID NO: 31), wherein the N-terminus of the cell-penetrating peptide is optionally acetylated, methylated, trifluoroacetylated, trifluoromethylsulfonylated, or methylsulfonylated.

5. The cell-penetrating peptide of claim 1, wherein the cell-penetrating peptide consists of the amino acid sequence RBRRBRRILFQYRBRBR (SEQ ID NO: 32), wherein the N-terminus of the cell-penetrating peptide is optionally acetylated, methylated, trifluoroacetylated, trifluoromethylsulfonylated, or methylsulfonylated.

6. The cell-penetrating peptide of claim 1, wherein the cell-penetrating peptide consists of the amino acid sequence RBRRBRFQILYBRBR (SEQ ID NO:35), wherein the N-terminus of the cell-penetrating peptide is optionally acetylated, methylated, trifluoroacetylated, trifluoromethylsulfonylated, or methylsulfonylated.

7. The cell-penetrating peptide of claim 6, wherein the N-terminus of the cell-penetrating peptide is acetylated.

8. The cell-penetrating peptide of claim 1, wherein the cell-penetrating peptide consists of the amino acid sequence RBRRBRRFQILYRBHBH (SEQ ID NO: 37), wherein the N-terminus of the cell-penetrating peptide is optionally acetylated, methylated, trifluoroacetylated, trifluoromethylsulfonylated, or methylsulfonylated.

9. The cell-penetrating peptide of claim 1, wherein the cell-penetrating peptide consists of the amino acid sequence RBRRBRRFQILYHBHBR (SEQ ID NO: 38), wherein the N-terminus of the cell-penetrating peptide is optionally acetylated, methylated, trifluoroacetylated, trifluoromethylsulfonylated, or methylsulfonylated.

10. The cell-penetrating peptide of claim 1, wherein of the cell-penetrating peptide consists of the amino acid sequence RBRRBRFQILYRBHBH (SEQ ID NO: 44), wherein the N-terminus of the cell-penetrating peptide is optionally acetylated, methylated, trifluoroacetylated, trifluoromethylsulfonylated, or methylsulfonylated.

11. The cell-penetrating peptide of claim 10, wherein the N-terminus of the cell-penetrating peptide is acetylated.

12. The cell-penetrating peptide of claim 1, wherein of the cell-penetrating peptide consists of the amino acid sequence RBRRBRFQILYRRBRBR (SEQ ID NO: 29, wherein the N-terminus of the cell-penetrating peptide is optionally acetylated, methylated, trifluoroacetylated, trifluoromethylsulfonylated, or methylsulfonylated.

13. The cell-penetrating peptide of claim 1, wherein the cell-penetrating peptide consists of the amino acid sequence RBRBRFQILYRBRRBRR (SEQ ID NO: 30, wherein the N-terminus of the cell-penetrating peptide is optionally acetylated, methylated, trifluoroacetylated, trifluoromethylsulfonylated, or methylsulfonylated.

14. The cell-penetrating peptide of claim 1, wherein the cell-penetrating peptide consists of the amino acid sequence RBRRBRFQILYRBRBR (SEQ ID NO: 33, wherein the N-terminus of the cell-penetrating peptide is optionally acetylated, methylated, trifluoroacetylated, trifluoromethylsulfonylated, or methylsulfonylated.

15. The cell-penetrating peptide of claim 1, wherein the cell-penetrating peptide consists of the amino acid sequence RBRRBFQILYRBRBR (SEQ ID NO: 36), wherein the N-terminus of the cell-penetrating peptide is optionally acetylated, methylated, trifluoroacetylated, trifluoromethylsulfonylated, or methylsulfonylated.

16. The cell-penetrating peptide of claim 1, wherein the cell-penetrating peptide consists of the amino acid sequence RBRRBRRFQILYHBRBH (SEQ ID NO: 39, wherein the N-terminus of the cell-penetrating peptide is optionally acetylated, methylated, trifluoroacetylated, trifluoromethylsulfonylated, or methylsulfonylated.

17. The cell-penetrating peptide of claim 1, wherein the cell-penetrating peptide consists of the amino acid sequence RBRRBRRYQFLIRBHBH (SEQ ID NO: 40, wherein the N-terminus of the cell-penetrating peptide is optionally acetylated, methylated, trifluoroacetylated, trifluoromethylsulfonylated, or methylsulfonylated.

18. The cell-penetrating peptide of claim 1, wherein the cell-penetrating peptide consists of the amino acid sequence RBRRBRRILFQYRBHBH (SEQ ID NO: 41, wherein the N-terminus of the cell-penetrating peptide is optionally acetylated, methylated, trifluoroacetylated, trifluoromethylsulfonylated, or methylsulfonylated.

19. The cell-penetrating peptide of claim 1, wherein the cell-penetrating peptide consists of the amino acid sequence RBRHBHRFQILYRBRBR (SEQ ID NO: 42, wherein the N-terminus of the cell-penetrating peptide is optionally acetylated, methylated, trifluoroacetylated, trifluoromethylsulfonylated, or methylsulfonylated.

20. The cell-penetrating peptide of claim 1, wherein the cell-penetrating peptide consists of the amino acid sequence RBRRBRRFQILYHBHBH (SEQ ID NO: 52, wherein the N-terminus of the cell-penetrating peptide is optionally acetylated, methylated, trifluoroacetylated, trifluoromethylsulfonylated, or methylsulfonylated.

21. The cell-penetrating peptide of claim 1, wherein the cell-penetrating peptide consists of the amino acid sequence RBRRBRWWWBRBR (SEQ ID NO: 104, wherein the N-terminus of the cell-penetrating peptide is optionally acetylated, methylated, trifluoroacetylated, trifluoromethylsulfonylated, or methylsulfonylated.

22. The cell-penetrating peptide of claim 1, wherein the cell-penetrating peptide consists of the amino acid sequence RBRRBRWWPWWBRBR (SEQ ID NO: 105, wherein the N-terminus of the cell-penetrating peptide is optionally acetylated, methylated, trifluoroacetylated, trifluoromethylsulfonylated, or methylsulfonylated.

* * * * *

UNITED STATES PATENT AND TRADEMARK OFFICE
CERTIFICATE OF CORRECTION

PATENT NO. : 12,268,749 B2  
APPLICATION NO. : 17/266939  
DATED : April 8, 2025  
INVENTOR(S) : Matthew Wood et al.

Page 1 of 1

It is certified that error appears in the above-identified patent and that said Letters Patent is hereby corrected as shown below:

In the Claims

Column 111, Claim 1, Lines 14-15, replace "trifluoromethylsullfonylated" with --trifluoromethylsulfonylated--.

Signed and Sealed this  
Twenty-ninth Day of July, 2025

Coke Morgan Stewart  
*Acting Director of the United States Patent and Trademark Office*

SEQUENCE LISTING

```
<160> NUMBER OF SEQ ID NOS: 115

<210> SEQ ID NO 1
<211> LENGTH: 7
<212> TYPE: PRT
<213> ORGANISM: Artificial Sequence
<220> FEATURE:
<223> OTHER INFORMATION: peptide
<220> FEATURE:
<221> NAME/KEY: MOD_RES
<222> LOCATION: (2)..(2)
<223> OTHER INFORMATION: X is bAla
<220> FEATURE:
<221> NAME/KEY: MOD_RES
<222> LOCATION: (5)..(5)
<223> OTHER INFORMATION: X is bAla

<400> SEQUENCE: 1

Arg Xaa Arg Arg Xaa Arg Arg
1               5

<210> SEQ ID NO 2
<211> LENGTH: 5
<212> TYPE: PRT
<213> ORGANISM: Artificial Sequence
<220> FEATURE:
<223> OTHER INFORMATION: peptide
<220> FEATURE:
<221> NAME/KEY: MOD_RES
<222> LOCATION: (2)..(2)
<223> OTHER INFORMATION: X is bAla
<220> FEATURE:
<221> NAME/KEY: MOD_RES
<222> LOCATION: (4)..(4)
<223> OTHER INFORMATION: X is bAla

<400> SEQUENCE: 2

Arg Xaa Arg Xaa Arg
1               5

<210> SEQ ID NO 3
```

```
<211> LENGTH: 4
<212> TYPE: PRT
<213> ORGANISM: Artificial Sequence
<220> FEATURE:
<223> OTHER INFORMATION: peptide
<220> FEATURE:
<221> NAME/KEY: MOD_RES
<222> LOCATION: (2)..(2)
<223> OTHER INFORMATION: X is bAla

<400> SEQUENCE: 3

Arg Xaa Arg Arg
1

<210> SEQ ID NO 4
<211> LENGTH: 6
<212> TYPE: PRT
<213> ORGANISM: Artificial Sequence
<220> FEATURE:
<223> OTHER INFORMATION: peptide
<220> FEATURE:
<221> NAME/KEY: MOD_RES
<222> LOCATION: (2)..(2)
<223> OTHER INFORMATION: X is bAla
<220> FEATURE:
<221> NAME/KEY: MOD_RES
<222> LOCATION: (5)..(5)
<223> OTHER INFORMATION: X is bAla

<400> SEQUENCE: 4

Arg Xaa Arg Arg Xaa Arg
1               5

<210> SEQ ID NO 5
<211> LENGTH: 6
<212> TYPE: PRT
<213> ORGANISM: Artificial Sequence
<220> FEATURE:
<223> OTHER INFORMATION: peptide
<220> FEATURE:
<221> NAME/KEY: MOD_RES
<222> LOCATION: (3)..(3)
<223> OTHER INFORMATION: x is bAla
<220> FEATURE:
<221> NAME/KEY: MOD_RES
<222> LOCATION: (5)..(5)
<223> OTHER INFORMATION: x is bAla

<400> SEQUENCE: 5

Arg Arg Xaa Arg Xaa Arg
1               5

<210> SEQ ID NO 6
<211> LENGTH: 5
<212> TYPE: PRT
<213> ORGANISM: Artificial Sequence
<220> FEATURE:
<223> OTHER INFORMATION: peptide
<220> FEATURE:
<221> NAME/KEY: MOD_RES
<222> LOCATION: (2)..(2)
<223> OTHER INFORMATION: x is bAla
<220> FEATURE:
<221> NAME/KEY: MOD_RES
<222> LOCATION: (5)..(5)
<223> OTHER INFORMATION: x is bAla

<400> SEQUENCE: 6

Arg Xaa Arg Arg Xaa
1               5
```

```
<210> SEQ ID NO 7
<211> LENGTH: 4
<212> TYPE: PRT
<213> ORGANISM: Artificial Sequence
<220> FEATURE:
<223> OTHER INFORMATION: peptide
<220> FEATURE:
<221> NAME/KEY: MOD_RES
<222> LOCATION: (1)..(1)
<223> OTHER INFORMATION: x is bAla
<220> FEATURE:
<221> NAME/KEY: MOD_RES
<222> LOCATION: (3)..(3)
<223> OTHER INFORMATION: x is bAla

<400> SEQUENCE: 7

Xaa Arg Xaa Arg
1

<210> SEQ ID NO 8
<211> LENGTH: 5
<212> TYPE: PRT
<213> ORGANISM: Artificial Sequence
<220> FEATURE:
<223> OTHER INFORMATION: peptide
<220> FEATURE:
<221> NAME/KEY: MOD_RES
<222> LOCATION: (2)..(2)
<223> OTHER INFORMATION: x is bAla
<220> FEATURE:
<221> NAME/KEY: MOD_RES
<222> LOCATION: (4)..(4)
<223> OTHER INFORMATION: x is bAla

<400> SEQUENCE: 8

Arg Xaa His Xaa His
1               5

<210> SEQ ID NO 9
<211> LENGTH: 5
<212> TYPE: PRT
<213> ORGANISM: Artificial Sequence
<220> FEATURE:
<223> OTHER INFORMATION: peptide
<220> FEATURE:
<221> NAME/KEY: MOD_RES
<222> LOCATION: (2)..(2)
<223> OTHER INFORMATION: x is bAla
<220> FEATURE:
<221> NAME/KEY: MOD_RES
<222> LOCATION: (4)..(4)
<223> OTHER INFORMATION: x is bAla

<400> SEQUENCE: 9

His Xaa His Xaa Arg
1               5

<210> SEQ ID NO 10
<211> LENGTH: 7
<212> TYPE: PRT
<213> ORGANISM: Artificial Sequence
<220> FEATURE:
<223> OTHER INFORMATION: peptide
<220> FEATURE:
<221> NAME/KEY: MOD_RES
<222> LOCATION: (2)..(2)
<223> OTHER INFORMATION: x is bAla
<220> FEATURE:
<221> NAME/KEY: MOD_RES
<222> LOCATION: (5)..(5)
<223> OTHER INFORMATION: x is bAla

<400> SEQUENCE: 10
```

```
Arg Xaa Arg His Xaa His Arg
1               5

<210> SEQ ID NO 11
<211> LENGTH: 7
<212> TYPE: PRT
<213> ORGANISM: Artificial Sequence
<220> FEATURE:
<223> OTHER INFORMATION: peptide
<220> FEATURE:
<221> NAME/KEY: MOD_RES
<222> LOCATION: (2)..(2)
<223> OTHER INFORMATION: x is bAla
<220> FEATURE:
<221> NAME/KEY: MOD_RES
<222> LOCATION: (4)..(5)
<223> OTHER INFORMATION: x is bAla

<400> SEQUENCE: 11

Arg Xaa Arg Xaa Xaa His Arg
1               5

<210> SEQ ID NO 12
<211> LENGTH: 6
<212> TYPE: PRT
<213> ORGANISM: Artificial Sequence
<220> FEATURE:
<223> OTHER INFORMATION: peptide
<220> FEATURE:
<221> NAME/KEY: MOD_RES
<222> LOCATION: (2)..(2)
<223> OTHER INFORMATION: x is bAla
<220> FEATURE:
<221> NAME/KEY: MOD_RES
<222> LOCATION: (5)..(5)
<223> OTHER INFORMATION: x is bAla

<400> SEQUENCE: 12

Arg Xaa Arg Arg Xaa His
1               5

<210> SEQ ID NO 13
<211> LENGTH: 6
<212> TYPE: PRT
<213> ORGANISM: Artificial Sequence
<220> FEATURE:
<223> OTHER INFORMATION: peptide
<220> FEATURE:
<221> NAME/KEY: MOD_RES
<222> LOCATION: (2)..(2)
<223> OTHER INFORMATION: x is bAla
<220> FEATURE:
<221> NAME/KEY: MOD_RES
<222> LOCATION: (5)..(5)
<223> OTHER INFORMATION: x is bAla

<400> SEQUENCE: 13

His Xaa Arg Arg Xaa Arg
1               5

<210> SEQ ID NO 14
<211> LENGTH: 5
<212> TYPE: PRT
<213> ORGANISM: Artificial Sequence
<220> FEATURE:
<223> OTHER INFORMATION: peptide
<220> FEATURE:
<221> NAME/KEY: MOD_RES
<222> LOCATION: (2)..(2)
<223> OTHER INFORMATION: x is bAla
<220> FEATURE:
```

```
<221> NAME/KEY: MOD_RES
<222> LOCATION: (4)..(4)
<223> OTHER INFORMATION: x is bAla

<400> SEQUENCE: 14

His Xaa His Xaa His
1               5

<210> SEQ ID NO 15
<211> LENGTH: 4
<212> TYPE: PRT
<213> ORGANISM: Artificial Sequence
<220> FEATURE:
<223> OTHER INFORMATION: peptide
<220> FEATURE:
<221> NAME/KEY: MOD_RES
<222> LOCATION: (1)..(1)
<223> OTHER INFORMATION: x is bAla
<220> FEATURE:
<221> NAME/KEY: MOD_RES
<222> LOCATION: (3)..(3)
<223> OTHER INFORMATION: x is bAla

<400> SEQUENCE: 15

Xaa His Xaa His
1

<210> SEQ ID NO 16
<211> LENGTH: 5
<212> TYPE: PRT
<213> ORGANISM: Artificial Sequence
<220> FEATURE:
<223> OTHER INFORMATION: peptide
<220> FEATURE:
<221> NAME/KEY: MOD_RES
<222> LOCATION: (1)..(1)
<223> OTHER INFORMATION: x is bAla
<220> FEATURE:
<221> NAME/KEY: MOD_RES
<222> LOCATION: (3)..(3)
<223> OTHER INFORMATION: x is bAla
<220> FEATURE:
<221> NAME/KEY: MOD_RES
<222> LOCATION: (5)..(5)
<223> OTHER INFORMATION: x is bAla

<400> SEQUENCE: 16

Xaa Arg Xaa Ser Xaa
1               5

<210> SEQ ID NO 17
<211> LENGTH: 5
<212> TYPE: PRT
<213> ORGANISM: Artificial Sequence
<220> FEATURE:
<223> OTHER INFORMATION: peptide
<220> FEATURE:
<221> NAME/KEY: MOD_RES
<222> LOCATION: (1)..(1)
<223> OTHER INFORMATION: x is bAla
<220> FEATURE:
<221> NAME/KEY: MOD_RES
<222> LOCATION: (3)..(3)
<223> OTHER INFORMATION: x is bAla
<220> FEATURE:
<221> NAME/KEY: MOD_RES
<222> LOCATION: (4)..(4)
<223> OTHER INFORMATION: x is hydroxyproline
<220> FEATURE:
<221> NAME/KEY: MOD_RES
<222> LOCATION: (5)..(5)
<223> OTHER INFORMATION: x is bAla
```

```
<400> SEQUENCE: 17

Xaa Arg Xaa Xaa Xaa
1               5

<210> SEQ ID NO 18
<211> LENGTH: 6
<212> TYPE: PRT
<213> ORGANISM: Artificial Sequence
<220> FEATURE:
<223> OTHER INFORMATION: peptide
<220> FEATURE:
<221> NAME/KEY: MOD_RES
<222> LOCATION: (2)..(2)
<223> OTHER INFORMATION: x is hydroxyproline
<220> FEATURE:
<221> NAME/KEY: MOD_RES
<222> LOCATION: (4)..(4)
<223> OTHER INFORMATION: x is hydroxyproline
<220> FEATURE:
<221> NAME/KEY: MOD_RES
<222> LOCATION: (6)..(6)
<223> OTHER INFORMATION: x is bAla

<400> SEQUENCE: 18

Arg Xaa His Xaa His Xaa
1               5

<210> SEQ ID NO 19
<211> LENGTH: 6
<212> TYPE: PRT
<213> ORGANISM: Artificial Sequence
<220> FEATURE:
<223> OTHER INFORMATION: peptide
<220> FEATURE:
<221> NAME/KEY: MOD_RES
<222> LOCATION: (2)..(2)
<223> OTHER INFORMATION: x is hydroxyproline
<220> FEATURE:
<221> NAME/KEY: MOD_RES
<222> LOCATION: (5)..(5)
<223> OTHER INFORMATION: x is hydroxyproline

<400> SEQUENCE: 19

Arg Xaa Arg Arg Xaa Arg
1               5

<210> SEQ ID NO 20
<211> LENGTH: 5
<212> TYPE: PRT
<213> ORGANISM: Artificial Sequence
<220> FEATURE:
<223> OTHER INFORMATION: peptide

<400> SEQUENCE: 20

Tyr Gln Phe Leu Ile
1               5

<210> SEQ ID NO 21
<211> LENGTH: 5
<212> TYPE: PRT
<213> ORGANISM: Artificial Sequence
<220> FEATURE:
<223> OTHER INFORMATION: peptide

<400> SEQUENCE: 21

Phe Gln Ile Leu Tyr
1               5

<210> SEQ ID NO 22
```

```
<211> LENGTH: 5
<212> TYPE: PRT
<213> ORGANISM: Artificial Sequence
<220> FEATURE:
<223> OTHER INFORMATION: peptide

<400> SEQUENCE: 22

Ile Leu Phe Gln Tyr
1               5

<210> SEQ ID NO 23
<211> LENGTH: 4
<212> TYPE: PRT
<213> ORGANISM: Artificial Sequence
<220> FEATURE:
<223> OTHER INFORMATION: peptide

<400> SEQUENCE: 23

Phe Gln Ile Tyr
1

<210> SEQ ID NO 24
<211> LENGTH: 5
<212> TYPE: PRT
<213> ORGANISM: Artificial Sequence
<220> FEATURE:
<223> OTHER INFORMATION: peptide

<400> SEQUENCE: 24

Trp Trp Pro Trp Trp
1               5

<210> SEQ ID NO 25
<211> LENGTH: 4
<212> TYPE: PRT
<213> ORGANISM: Artificial Sequence
<220> FEATURE:
<223> OTHER INFORMATION: peptide

<400> SEQUENCE: 25

Trp Pro Trp Trp
1

<210> SEQ ID NO 26
<211> LENGTH: 4
<212> TYPE: PRT
<213> ORGANISM: Artificial Sequence
<220> FEATURE:
<223> OTHER INFORMATION: peptide

<400> SEQUENCE: 26

Trp Trp Pro Trp
1

<210> SEQ ID NO 27
<211> LENGTH: 17
<212> TYPE: PRT
<213> ORGANISM: Artificial Sequence
<220> FEATURE:
<223> OTHER INFORMATION: peptide
<220> FEATURE:
<221> NAME/KEY: MOD_RES
<222> LOCATION: (2)..(2)
<223> OTHER INFORMATION: x is bAla
<220> FEATURE:
<221> NAME/KEY: MOD_RES
<222> LOCATION: (5)..(5)
<223> OTHER INFORMATION: x is bAla
<220> FEATURE:
```

```
<221> NAME/KEY: MOD_RES
<222> LOCATION: (14)..(14)
<223> OTHER INFORMATION: x is bAla
<220> FEATURE:
<221> NAME/KEY: MOD_RES
<222> LOCATION: (16)..(16)
<223> OTHER INFORMATION: x is bAla

<400> SEQUENCE: 27

Arg Xaa Arg Arg Xaa Arg Arg Phe Gln Ile Leu Tyr Arg Xaa Arg Xaa
1               5                   10                  15

Arg

<210> SEQ ID NO 28
<211> LENGTH: 16
<212> TYPE: PRT
<213> ORGANISM: Artificial Sequence
<220> FEATURE:
<223> OTHER INFORMATION: peptide
<220> FEATURE:
<221> NAME/KEY: MOD_RES
<222> LOCATION: (2)..(2)
<223> OTHER INFORMATION: x is bAla
<220> FEATURE:
<221> NAME/KEY: MOD_RES
<222> LOCATION: (5)..(5)
<223> OTHER INFORMATION: x is bAla
<220> FEATURE:
<221> NAME/KEY: MOD_RES
<222> LOCATION: (14)..(14)
<223> OTHER INFORMATION: x is bAla

<400> SEQUENCE: 28

Arg Xaa Arg Arg Xaa Arg Arg Phe Gln Ile Leu Tyr Arg Xaa Arg Arg
1               5                   10                  15

<210> SEQ ID NO 29
<211> LENGTH: 17
<212> TYPE: PRT
<213> ORGANISM: Artificial Sequence
<220> FEATURE:
<223> OTHER INFORMATION: peptide
<220> FEATURE:
<221> NAME/KEY: MOD_RES
<222> LOCATION: (2)..(2)
<223> OTHER INFORMATION: x is bAla
<220> FEATURE:
<221> NAME/KEY: MOD_RES
<222> LOCATION: (5)..(5)
<223> OTHER INFORMATION: x is bAla
<220> FEATURE:
<221> NAME/KEY: MOD_RES
<222> LOCATION: (14)..(14)
<223> OTHER INFORMATION: x is bAla
<220> FEATURE:
<221> NAME/KEY: MOD_RES
<222> LOCATION: (16)..(16)
<223> OTHER INFORMATION: x is bAla

<400> SEQUENCE: 29

Arg Xaa Arg Arg Xaa Arg Phe Gln Ile Leu Tyr Arg Xaa Arg Xaa
1               5                   10                  15

Arg

<210> SEQ ID NO 30
<211> LENGTH: 17
<212> TYPE: PRT
<213> ORGANISM: Artificial Sequence
<220> FEATURE:
<223> OTHER INFORMATION: peptide
<220> FEATURE:
```

```
<221> NAME/KEY: MOD_RES
<222> LOCATION: (2)..(2)
<223> OTHER INFORMATION: x is bAla
<220> FEATURE:
<221> NAME/KEY: MOD_RES
<222> LOCATION: (4)..(4)
<223> OTHER INFORMATION: x is bAla
<220> FEATURE:
<221> NAME/KEY: MOD_RES
<222> LOCATION: (12)..(12)
<223> OTHER INFORMATION: x is bAla
<220> FEATURE:
<221> NAME/KEY: MOD_RES
<222> LOCATION: (15)..(15)
<223> OTHER INFORMATION: x is bAla

<400> SEQUENCE: 30

Arg Xaa Arg Xaa Arg Phe Gln Ile Leu Tyr Arg Xaa Arg Arg Xaa Arg
 1               5                  10                  15

Arg

<210> SEQ ID NO 31
<211> LENGTH: 17
<212> TYPE: PRT
<213> ORGANISM: Artificial Sequence
<220> FEATURE:
<223> OTHER INFORMATION: peptide
<220> FEATURE:
<221> NAME/KEY: MOD_RES
<222> LOCATION: (2)..(2)
<223> OTHER INFORMATION: x is bAla
<220> FEATURE:
<221> NAME/KEY: MOD_RES
<222> LOCATION: (5)..(5)
<223> OTHER INFORMATION: x is bAla
<220> FEATURE:
<221> NAME/KEY: MOD_RES
<222> LOCATION: (14)..(14)
<223> OTHER INFORMATION: x is bAla
<220> FEATURE:
<221> NAME/KEY: MOD_RES
<222> LOCATION: (16)..(16)
<223> OTHER INFORMATION: x is bAla

<400> SEQUENCE: 31

Arg Xaa Arg Arg Xaa Arg Arg Tyr Gln Phe Leu Ile Arg Xaa Arg Xaa
 1               5                  10                  15

Arg

<210> SEQ ID NO 32
<211> LENGTH: 17
<212> TYPE: PRT
<213> ORGANISM: Artificial Sequence
<220> FEATURE:
<223> OTHER INFORMATION: peptide
<220> FEATURE:
<221> NAME/KEY: MOD_RES
<222> LOCATION: (2)..(2)
<223> OTHER INFORMATION: x is bAla
<220> FEATURE:
<221> NAME/KEY: MOD_RES
<222> LOCATION: (5)..(5)
<223> OTHER INFORMATION: x is bAla
<220> FEATURE:
<221> NAME/KEY: MOD_RES
<222> LOCATION: (14)..(14)
<223> OTHER INFORMATION: x is bAla
<220> FEATURE:
<221> NAME/KEY: MOD_RES
<222> LOCATION: (16)..(16)
<223> OTHER INFORMATION: x is bAla

<400> SEQUENCE: 32
```

Arg Xaa Arg Arg Xaa Arg Arg Ile Leu Phe Gln Tyr Arg Xaa Arg Xaa
1               5                   10                  15

Arg

<210> SEQ ID NO 33
<211> LENGTH: 16
<212> TYPE: PRT
<213> ORGANISM: Artificial Sequence
<220> FEATURE:
<223> OTHER INFORMATION: peptide
<220> FEATURE:
<221> NAME/KEY: MOD_RES
<222> LOCATION: (2)..(2)
<223> OTHER INFORMATION: x is bAla
<220> FEATURE:
<221> NAME/KEY: MOD_RES
<222> LOCATION: (5)..(5)
<223> OTHER INFORMATION: x is bAla
<220> FEATURE:
<221> NAME/KEY: MOD_RES
<222> LOCATION: (13)..(13)
<223> OTHER INFORMATION: x is bAla
<220> FEATURE:
<221> NAME/KEY: MOD_RES
<222> LOCATION: (15)..(15)
<223> OTHER INFORMATION: x is bAla

<400> SEQUENCE: 33

Arg Xaa Arg Arg Xaa Arg Phe Gln Ile Leu Tyr Arg Xaa Arg Xaa Arg
1               5                   10                  15

<210> SEQ ID NO 34
<211> LENGTH: 16
<212> TYPE: PRT
<213> ORGANISM: Artificial Sequence
<220> FEATURE:
<223> OTHER INFORMATION: peptide
<220> FEATURE:
<221> NAME/KEY: MOD_RES
<222> LOCATION: (2)..(2)
<223> OTHER INFORMATION: x is bAla
<220> FEATURE:
<221> NAME/KEY: MOD_RES
<222> LOCATION: (5)..(5)
<223> OTHER INFORMATION: x is bAla
<220> FEATURE:
<221> NAME/KEY: MOD_RES
<222> LOCATION: (12)..(12)
<223> OTHER INFORMATION: x is bAla
<220> FEATURE:
<221> NAME/KEY: MOD_RES
<222> LOCATION: (15)..(15)
<223> OTHER INFORMATION: x is bAla

<400> SEQUENCE: 34

Arg Xaa Arg Arg Xaa Phe Gln Ile Leu Tyr Arg Xaa Arg Arg Xaa Arg
1               5                   10                  15

<210> SEQ ID NO 35
<211> LENGTH: 15
<212> TYPE: PRT
<213> ORGANISM: Artificial Sequence
<220> FEATURE:
<223> OTHER INFORMATION: peptide
<220> FEATURE:
<221> NAME/KEY: MOD_RES
<222> LOCATION: (2)..(2)
<223> OTHER INFORMATION: x is bAla
<220> FEATURE:
<221> NAME/KEY: MOD_RES
<222> LOCATION: (5)..(5)
<223> OTHER INFORMATION: x is bAla

```
<220> FEATURE:
<221> NAME/KEY: MOD_RES
<222> LOCATION: (12)..(12)
<223> OTHER INFORMATION: x is bAla
<220> FEATURE:
<221> NAME/KEY: MOD_RES
<222> LOCATION: (14)..(14)
<223> OTHER INFORMATION: x is bAla

<400> SEQUENCE: 35

Arg Xaa Arg Arg Xaa Arg Phe Gln Ile Leu Tyr Xaa Arg Xaa Arg
1               5                   10                  15

<210> SEQ ID NO 36
<211> LENGTH: 15
<212> TYPE: PRT
<213> ORGANISM: Artificial Sequence
<220> FEATURE:
<223> OTHER INFORMATION: peptide
<220> FEATURE:
<221> NAME/KEY: MOD_RES
<222> LOCATION: (2)..(2)
<223> OTHER INFORMATION: x is bAla
<220> FEATURE:
<221> NAME/KEY: MOD_RES
<222> LOCATION: (5)..(5)
<223> OTHER INFORMATION: x is bAla
<220> FEATURE:
<221> NAME/KEY: MOD_RES
<222> LOCATION: (12)..(12)
<223> OTHER INFORMATION: x is bAla
<220> FEATURE:
<221> NAME/KEY: MOD_RES
<222> LOCATION: (14)..(14)
<223> OTHER INFORMATION: x is bAla

<400> SEQUENCE: 36

Arg Xaa Arg Arg Xaa Phe Gln Ile Leu Tyr Arg Xaa Arg Xaa Arg
1               5                   10                  15

<210> SEQ ID NO 37
<211> LENGTH: 17
<212> TYPE: PRT
<213> ORGANISM: Artificial Sequence
<220> FEATURE:
<223> OTHER INFORMATION: peptide
<220> FEATURE:
<221> NAME/KEY: MOD_RES
<222> LOCATION: (2)..(2)
<223> OTHER INFORMATION: x is bAla
<220> FEATURE:
<221> NAME/KEY: MOD_RES
<222> LOCATION: (5)..(5)
<223> OTHER INFORMATION: x is bAla
<220> FEATURE:
<221> NAME/KEY: MOD_RES
<222> LOCATION: (14)..(14)
<223> OTHER INFORMATION: x is bAla
<220> FEATURE:
<221> NAME/KEY: MOD_RES
<222> LOCATION: (16)..(16)
<223> OTHER INFORMATION: x is bAla

<400> SEQUENCE: 37

Arg Xaa Arg Arg Xaa Arg Arg Phe Gln Ile Leu Tyr Arg Xaa His Xaa
1               5                   10                  15
His

<210> SEQ ID NO 38
<211> LENGTH: 17
<212> TYPE: PRT
<213> ORGANISM: Artificial Sequence
```

```
<220> FEATURE:
<223> OTHER INFORMATION: peptide
<220> FEATURE:
<221> NAME/KEY: MOD_RES
<222> LOCATION: (2)..(2)
<223> OTHER INFORMATION: x is bAla
<220> FEATURE:
<221> NAME/KEY: MOD_RES
<222> LOCATION: (5)..(5)
<223> OTHER INFORMATION: x is bAla
<220> FEATURE:
<221> NAME/KEY: MOD_RES
<222> LOCATION: (14)..(14)
<223> OTHER INFORMATION: x is bAla
<220> FEATURE:
<221> NAME/KEY: MOD_RES
<222> LOCATION: (16)..(16)
<223> OTHER INFORMATION: x is bAla

<400> SEQUENCE: 38

Arg Xaa Arg Arg Xaa Arg Arg Phe Gln Ile Leu Tyr His Xaa His Xaa
 1               5                  10                  15

Arg

<210> SEQ ID NO 39
<211> LENGTH: 17
<212> TYPE: PRT
<213> ORGANISM: Artificial Sequence
<220> FEATURE:
<223> OTHER INFORMATION: peptide
<220> FEATURE:
<221> NAME/KEY: MOD_RES
<222> LOCATION: (2)..(2)
<223> OTHER INFORMATION: x is bAla
<220> FEATURE:
<221> NAME/KEY: MOD_RES
<222> LOCATION: (5)..(5)
<223> OTHER INFORMATION: x is bAla
<220> FEATURE:
<221> NAME/KEY: MOD_RES
<222> LOCATION: (14)..(14)
<223> OTHER INFORMATION: x is bAla
<220> FEATURE:
<221> NAME/KEY: MOD_RES
<222> LOCATION: (16)..(16)
<223> OTHER INFORMATION: x is bAla

<400> SEQUENCE: 39

Arg Xaa Arg Arg Xaa Arg Arg Phe Gln Ile Leu Tyr His Xaa Arg Xaa
 1               5                  10                  15

His

<210> SEQ ID NO 40
<211> LENGTH: 17
<212> TYPE: PRT
<213> ORGANISM: Artificial Sequence
<220> FEATURE:
<223> OTHER INFORMATION: peptide
<220> FEATURE:
<221> NAME/KEY: MOD_RES
<222> LOCATION: (2)..(2)
<223> OTHER INFORMATION: x is bAla
<220> FEATURE:
<221> NAME/KEY: MOD_RES
<222> LOCATION: (5)..(5)
<223> OTHER INFORMATION: x is bAla
<220> FEATURE:
<221> NAME/KEY: MOD_RES
<222> LOCATION: (14)..(14)
<223> OTHER INFORMATION: x is bAla
<220> FEATURE:
<221> NAME/KEY: MOD_RES
<222> LOCATION: (16)..(16)
```

<223> OTHER INFORMATION: x is bAla

<400> SEQUENCE: 40

Arg Xaa Arg Arg Xaa Arg Arg Tyr Gln Phe Leu Ile Arg Xaa His Xaa
1               5                   10                  15

His

<210> SEQ ID NO 41
<211> LENGTH: 17
<212> TYPE: PRT
<213> ORGANISM: Artificial Sequence
<220> FEATURE:
<223> OTHER INFORMATION: peptide
<220> FEATURE:
<221> NAME/KEY: MOD_RES
<222> LOCATION: (2)..(2)
<223> OTHER INFORMATION: x is bAla
<220> FEATURE:
<221> NAME/KEY: MOD_RES
<222> LOCATION: (5)..(5)
<223> OTHER INFORMATION: x is bAla
<220> FEATURE:
<221> NAME/KEY: MOD_RES
<222> LOCATION: (14)..(14)
<223> OTHER INFORMATION: x is bAla
<220> FEATURE:
<221> NAME/KEY: MOD_RES
<222> LOCATION: (16)..(16)
<223> OTHER INFORMATION: x is bAla

<400> SEQUENCE: 41

Arg Xaa Arg Arg Xaa Arg Arg Ile Leu Phe Gln Tyr Arg Xaa His Xaa
1               5                   10                  15

His

<210> SEQ ID NO 42
<211> LENGTH: 17
<212> TYPE: PRT
<213> ORGANISM: Artificial Sequence
<220> FEATURE:
<223> OTHER INFORMATION: peptide
<220> FEATURE:
<221> NAME/KEY: MOD_RES
<222> LOCATION: (2)..(2)
<223> OTHER INFORMATION: x is bAla
<220> FEATURE:
<221> NAME/KEY: MOD_RES
<222> LOCATION: (5)..(5)
<223> OTHER INFORMATION: x is bAla
<220> FEATURE:
<221> NAME/KEY: MOD_RES
<222> LOCATION: (14)..(14)
<223> OTHER INFORMATION: x is bAla
<220> FEATURE:
<221> NAME/KEY: MOD_RES
<222> LOCATION: (16)..(16)
<223> OTHER INFORMATION: x is bAla

<400> SEQUENCE: 42

Arg Xaa Arg His Xaa His Arg Phe Gln Ile Leu Tyr Arg Xaa Arg Xaa
1               5                   10                  15

Arg

<210> SEQ ID NO 43
<211> LENGTH: 17
<212> TYPE: PRT
<213> ORGANISM: Artificial Sequence
<220> FEATURE:
<223> OTHER INFORMATION: peptide
<220> FEATURE:

```
<221> NAME/KEY: MOD_RES
<222> LOCATION: (2)..(2)
<223> OTHER INFORMATION: x is bAla
<220> FEATURE:
<221> NAME/KEY: MOD_RES
<222> LOCATION: (4)..(4)
<223> OTHER INFORMATION: x is bAla
<220> FEATURE:
<221> NAME/KEY: MOD_RES
<222> LOCATION: (5)..(5)
<223> OTHER INFORMATION: x is bAla
<220> FEATURE:
<221> NAME/KEY: MOD_RES
<222> LOCATION: (14)..(14)
<223> OTHER INFORMATION: x is bAla
<220> FEATURE:
<221> NAME/KEY: MOD_RES
<222> LOCATION: (16)..(16)
<223> OTHER INFORMATION: x is bAla

<400> SEQUENCE: 43

Arg Xaa Arg Xaa Xaa His Arg Phe Gln Ile Leu Tyr Arg Xaa His Xaa
1               5                   10                  15

His

<210> SEQ ID NO 44
<211> LENGTH: 16
<212> TYPE: PRT
<213> ORGANISM: Artificial Sequence
<220> FEATURE:
<223> OTHER INFORMATION: peptide
<220> FEATURE:
<221> NAME/KEY: MOD_RES
<222> LOCATION: (2)..(2)
<223> OTHER INFORMATION: x is bAla
<220> FEATURE:
<221> NAME/KEY: MOD_RES
<222> LOCATION: (5)..(5)
<223> OTHER INFORMATION: x is bAla
<220> FEATURE:
<221> NAME/KEY: MOD_RES
<222> LOCATION: (13)..(13)
<223> OTHER INFORMATION: x is bAla
<220> FEATURE:
<221> NAME/KEY: MOD_RES
<222> LOCATION: (15)..(15)
<223> OTHER INFORMATION: x is bAla

<400> SEQUENCE: 44

Arg Xaa Arg Arg Xaa Arg Phe Gln Ile Leu Tyr Arg Xaa His Xaa His
1               5                   10                  15

<210> SEQ ID NO 45
<211> LENGTH: 16
<212> TYPE: PRT
<213> ORGANISM: Artificial Sequence
<220> FEATURE:
<223> OTHER INFORMATION: peptide
<220> FEATURE:
<221> NAME/KEY: MOD_RES
<222> LOCATION: (2)..(2)
<223> OTHER INFORMATION: x is bAla
<220> FEATURE:
<221> NAME/KEY: MOD_RES
<222> LOCATION: (5)..(5)
<223> OTHER INFORMATION: x is bAla
<220> FEATURE:
<221> NAME/KEY: MOD_RES
<222> LOCATION: (13)..(13)
<223> OTHER INFORMATION: x is bAla
<220> FEATURE:
<221> NAME/KEY: MOD_RES
<222> LOCATION: (15)..(15)
<223> OTHER INFORMATION: x is bAla
```

```
<400> SEQUENCE: 45

Arg Xaa Arg Arg Xaa Arg Phe Gln Ile Leu Tyr His Xaa His Xaa His
1               5                   10                  15

<210> SEQ ID NO 46
<211> LENGTH: 16
<212> TYPE: PRT
<213> ORGANISM: Artificial Sequence
<220> FEATURE:
<223> OTHER INFORMATION: peptide
<220> FEATURE:
<221> NAME/KEY: MOD_RES
<222> LOCATION: (2)..(2)
<223> OTHER INFORMATION: x is bAla
<220> FEATURE:
<221> NAME/KEY: MOD_RES
<222> LOCATION: (5)..(5)
<223> OTHER INFORMATION: x is bAla
<220> FEATURE:
<221> NAME/KEY: MOD_RES
<222> LOCATION: (13)..(13)
<223> OTHER INFORMATION: x is bAla
<220> FEATURE:
<221> NAME/KEY: MOD_RES
<222> LOCATION: (15)..(15)
<223> OTHER INFORMATION: x is bAla

<400> SEQUENCE: 46

Arg Xaa Arg Arg Xaa His Phe Gln Ile Leu Tyr Arg Xaa His Xaa His
1               5                   10                  15

<210> SEQ ID NO 47
<211> LENGTH: 16
<212> TYPE: PRT
<213> ORGANISM: Artificial Sequence
<220> FEATURE:
<223> OTHER INFORMATION: peptide
<220> FEATURE:
<221> NAME/KEY: MOD_RES
<222> LOCATION: (2)..(2)
<223> OTHER INFORMATION: x is bAla
<220> FEATURE:
<221> NAME/KEY: MOD_RES
<222> LOCATION: (5)..(5)
<223> OTHER INFORMATION: x is bAla
<220> FEATURE:
<221> NAME/KEY: MOD_RES
<222> LOCATION: (13)..(13)
<223> OTHER INFORMATION: x is bAla
<220> FEATURE:
<221> NAME/KEY: MOD_RES
<222> LOCATION: (15)..(15)
<223> OTHER INFORMATION: x is bAla

<400> SEQUENCE: 47

His Xaa Arg Arg Xaa Arg Phe Gln Ile Leu Tyr Arg Xaa His Xaa His
1               5                   10                  15

<210> SEQ ID NO 48
<211> LENGTH: 15
<212> TYPE: PRT
<213> ORGANISM: Artificial Sequence
<220> FEATURE:
<223> OTHER INFORMATION: peptide
<220> FEATURE:
<221> NAME/KEY: MOD_RES
<222> LOCATION: (2)..(2)
<223> OTHER INFORMATION: x is bAla
<220> FEATURE:
<221> NAME/KEY: MOD_RES
<222> LOCATION: (5)..(5)
<223> OTHER INFORMATION: x is bAla
```

```
<220> FEATURE:
<221> NAME/KEY: MOD_RES
<222> LOCATION: (12)..(12)
<223> OTHER INFORMATION: x is bAla
<220> FEATURE:
<221> NAME/KEY: MOD_RES
<222> LOCATION: (14)..(14)
<223> OTHER INFORMATION: x is bAla

<400> SEQUENCE: 48

Arg Xaa Arg Arg Xaa Phe Gln Ile Leu Tyr Arg Xaa His Xaa His
1               5                   10                  15

<210> SEQ ID NO 49
<211> LENGTH: 15
<212> TYPE: PRT
<213> ORGANISM: Artificial Sequence
<220> FEATURE:
<223> OTHER INFORMATION: peptide
<220> FEATURE:
<221> NAME/KEY: MOD_RES
<222> LOCATION: (2)..(2)
<223> OTHER INFORMATION: x is bAla
<220> FEATURE:
<221> NAME/KEY: MOD_RES
<222> LOCATION: (5)..(5)
<223> OTHER INFORMATION: x is bAla
<220> FEATURE:
<221> NAME/KEY: MOD_RES
<222> LOCATION: (12)..(12)
<223> OTHER INFORMATION: x is bAla
<220> FEATURE:
<221> NAME/KEY: MOD_RES
<222> LOCATION: (14)..(14)
<223> OTHER INFORMATION: x is bAla

<400> SEQUENCE: 49

Arg Xaa Arg Arg Xaa Arg Phe Gln Ile Leu Tyr Xaa His Xaa His
1               5                   10                  15

<210> SEQ ID NO 50
<211> LENGTH: 16
<212> TYPE: PRT
<213> ORGANISM: Artificial Sequence
<220> FEATURE:
<223> OTHER INFORMATION: peptide
<220> FEATURE:
<221> NAME/KEY: MOD_RES
<222> LOCATION: (2)..(2)
<223> OTHER INFORMATION: x is bAla
<220> FEATURE:
<221> NAME/KEY: MOD_RES
<222> LOCATION: (5)..(5)
<223> OTHER INFORMATION: x is bAla
<220> FEATURE:
<221> NAME/KEY: MOD_RES
<222> LOCATION: (13)..(13)
<223> OTHER INFORMATION: x is bAla
<220> FEATURE:
<221> NAME/KEY: MOD_RES
<222> LOCATION: (15)..(15)
<223> OTHER INFORMATION: x is bAla

<400> SEQUENCE: 50

Arg Xaa Arg Arg Xaa Arg Tyr Gln Phe Leu Ile His Xaa His Xaa His
1               5                   10                  15

<210> SEQ ID NO 51
<211> LENGTH: 16
<212> TYPE: PRT
<213> ORGANISM: Artificial Sequence
<220> FEATURE:
<223> OTHER INFORMATION: peptide
```

```
<220> FEATURE:
<221> NAME/KEY: MOD_RES
<222> LOCATION: (2)..(2)
<223> OTHER INFORMATION: x is bAla
<220> FEATURE:
<221> NAME/KEY: MOD_RES
<222> LOCATION: (5)..(5)
<223> OTHER INFORMATION: x is bAla
<220> FEATURE:
<221> NAME/KEY: MOD_RES
<222> LOCATION: (13)..(13)
<223> OTHER INFORMATION: x is bAla
<220> FEATURE:
<221> NAME/KEY: MOD_RES
<222> LOCATION: (15)..(15)
<223> OTHER INFORMATION: x is bAla

<400> SEQUENCE: 51

Arg Xaa Arg Arg Xaa Arg Ile Leu Phe Gln Tyr His Xaa His Xaa His
1               5                   10                  15

<210> SEQ ID NO 52
<211> LENGTH: 17
<212> TYPE: PRT
<213> ORGANISM: Artificial Sequence
<220> FEATURE:
<223> OTHER INFORMATION: peptide
<220> FEATURE:
<221> NAME/KEY: MOD_RES
<222> LOCATION: (2)..(2)
<223> OTHER INFORMATION: x is bAla
<220> FEATURE:
<221> NAME/KEY: MOD_RES
<222> LOCATION: (5)..(5)
<223> OTHER INFORMATION: x is bAla
<220> FEATURE:
<221> NAME/KEY: MOD_RES
<222> LOCATION: (14)..(14)
<223> OTHER INFORMATION: x is bAla
<220> FEATURE:
<221> NAME/KEY: MOD_RES
<222> LOCATION: (16)..(16)
<223> OTHER INFORMATION: x is bAla

<400> SEQUENCE: 52

Arg Xaa Arg Arg Xaa Arg Arg Phe Gln Ile Leu Tyr His Xaa His Xaa
1               5                   10                  15

His

<210> SEQ ID NO 53
<211> LENGTH: 15
<212> TYPE: PRT
<213> ORGANISM: Artificial Sequence
<220> FEATURE:
<223> OTHER INFORMATION: peptide
<220> FEATURE:
<221> NAME/KEY: MOD_RES
<222> LOCATION: (2)..(2)
<223> OTHER INFORMATION: x is bAla
<220> FEATURE:
<221> NAME/KEY: MOD_RES
<222> LOCATION: (5)..(5)
<223> OTHER INFORMATION: x is bAla
<220> FEATURE:
<221> NAME/KEY: MOD_RES
<222> LOCATION: (12)..(12)
<223> OTHER INFORMATION: x is bAla
<220> FEATURE:
<221> NAME/KEY: MOD_RES
<222> LOCATION: (14)..(14)
<223> OTHER INFORMATION: x is bAla

<400> SEQUENCE: 53
```

Arg Xaa Arg Arg Xaa Arg Phe Gln Ile Leu Tyr Xaa Arg Xaa Ser
1               5                   10                  15

<210> SEQ ID NO 54
<211> LENGTH: 15
<212> TYPE: PRT
<213> ORGANISM: Artificial Sequence
<220> FEATURE:
<223> OTHER INFORMATION: peptide
<220> FEATURE:
<221> NAME/KEY: MOD_RES
<222> LOCATION: (2)..(2)
<223> OTHER INFORMATION: x is bAla
<220> FEATURE:
<221> NAME/KEY: MOD_RES
<222> LOCATION: (5)..(5)
<223> OTHER INFORMATION: x is bAla
<220> FEATURE:
<221> NAME/KEY: MOD_RES
<222> LOCATION: (12)..(12)
<223> OTHER INFORMATION: x is bAla
<220> FEATURE:
<221> NAME/KEY: MOD_RES
<222> LOCATION: (14)..(14)
<223> OTHER INFORMATION: x is bAla
<220> FEATURE:
<221> NAME/KEY: MOD_RES
<222> LOCATION: (15)..(15)
<223> OTHER INFORMATION: x hydroxyproline

<400> SEQUENCE: 54

Arg Xaa Arg Arg Xaa Arg Phe Gln Ile Leu Tyr Xaa Arg Xaa Xaa
1               5                   10                  15

<210> SEQ ID NO 55
<211> LENGTH: 15
<212> TYPE: PRT
<213> ORGANISM: Artificial Sequence
<220> FEATURE:
<223> OTHER INFORMATION: peptide
<220> FEATURE:
<221> NAME/KEY: MOD_RES
<222> LOCATION: (2)..(2)
<223> OTHER INFORMATION: x is bAla
<220> FEATURE:
<221> NAME/KEY: MOD_RES
<222> LOCATION: (5)..(5)
<223> OTHER INFORMATION: x is bAla
<220> FEATURE:
<221> NAME/KEY: MOD_RES
<222> LOCATION: (12)..(12)
<223> OTHER INFORMATION: x is bAla
<220> FEATURE:
<221> NAME/KEY: MOD_RES
<222> LOCATION: (14)..(14)
<223> OTHER INFORMATION: x is hydroxyproline

<400> SEQUENCE: 55

Arg Xaa Arg Arg Xaa Arg Phe Gln Ile Leu Tyr Xaa Arg Xaa Arg
1               5                   10                  15

<210> SEQ ID NO 56
<211> LENGTH: 16
<212> TYPE: PRT
<213> ORGANISM: Artificial Sequence
<220> FEATURE:
<223> OTHER INFORMATION: peptide
<220> FEATURE:
<221> NAME/KEY: MOD_RES
<222> LOCATION: (3)..(3)
<223> OTHER INFORMATION: x is bAla
<220> FEATURE:
<221> NAME/KEY: MOD_RES
<222> LOCATION: (6)..(6)

```
<223> OTHER INFORMATION: x is bAla
<220> FEATURE:
<221> NAME/KEY: MOD_RES
<222> LOCATION: (13)..(13)
<223> OTHER INFORMATION: x is bAla
<220> FEATURE:
<221> NAME/KEY: MOD_RES
<222> LOCATION: (15)..(15)
<223> OTHER INFORMATION: x is bAla

<400> SEQUENCE: 56

Arg Arg Xaa Arg Arg Xaa Arg Phe Gln Ile Leu Tyr Xaa Arg Xaa Arg
1               5                   10                  15

<210> SEQ ID NO 57
<211> LENGTH: 15
<212> TYPE: PRT
<213> ORGANISM: Artificial Sequence
<220> FEATURE:
<223> OTHER INFORMATION: peptide
<220> FEATURE:
<221> NAME/KEY: MOD_RES
<222> LOCATION: (1)..(1)
<223> OTHER INFORMATION: x is bAla
<220> FEATURE:
<221> NAME/KEY: MOD_RES
<222> LOCATION: (4)..(4)
<223> OTHER INFORMATION: x is bAla
<220> FEATURE:
<221> NAME/KEY: MOD_RES
<222> LOCATION: (12)..(12)
<223> OTHER INFORMATION: x is bAla
<220> FEATURE:
<221> NAME/KEY: MOD_RES
<222> LOCATION: (14)..(14)
<223> OTHER INFORMATION: x is bAla

<400> SEQUENCE: 57

Xaa Arg Arg Xaa Arg Arg Phe Gln Ile Leu Tyr Xaa Arg Xaa Arg
1               5                   10                  15

<210> SEQ ID NO 58
<211> LENGTH: 13
<212> TYPE: PRT
<213> ORGANISM: Artificial Sequence
<220> FEATURE:
<223> OTHER INFORMATION: peptide
<220> FEATURE:
<221> NAME/KEY: MOD_RES
<222> LOCATION: (2)..(2)
<223> OTHER INFORMATION: x is bAla
<220> FEATURE:
<221> NAME/KEY: MOD_RES
<222> LOCATION: (5)..(5)
<223> OTHER INFORMATION: x is bAla
<220> FEATURE:
<221> NAME/KEY: MOD_RES
<222> LOCATION: (10)..(10)
<223> OTHER INFORMATION: x is bAla
<220> FEATURE:
<221> NAME/KEY: MOD_RES
<222> LOCATION: (12)..(12)
<223> OTHER INFORMATION: x is bAla

<400> SEQUENCE: 58

Arg Xaa Arg Arg Xaa Arg Trp Trp Trp Xaa Arg Xaa Arg
1               5                   10

<210> SEQ ID NO 59
<211> LENGTH: 15
<212> TYPE: PRT
<213> ORGANISM: Artificial Sequence
<220> FEATURE:
```

```
<223> OTHER INFORMATION: peptide
<220> FEATURE:
<221> NAME/KEY: MOD_RES
<222> LOCATION: (2)..(2)
<223> OTHER INFORMATION: x is bAla
<220> FEATURE:
<221> NAME/KEY: MOD_RES
<222> LOCATION: (5)..(5)
<223> OTHER INFORMATION: x is bAla
<220> FEATURE:
<221> NAME/KEY: MOD_RES
<222> LOCATION: (12)..(12)
<223> OTHER INFORMATION: x is bAla
<220> FEATURE:
<221> NAME/KEY: MOD_RES
<222> LOCATION: (14)..(14)
<223> OTHER INFORMATION: x is bAla

<400> SEQUENCE: 59

Arg Xaa Arg Arg Xaa Arg Trp Trp Pro Trp Trp Xaa Arg Xaa Arg
1               5                   10                  15

<210> SEQ ID NO 60
<211> LENGTH: 14
<212> TYPE: PRT
<213> ORGANISM: Artificial Sequence
<220> FEATURE:
<223> OTHER INFORMATION: peptide
<220> FEATURE:
<221> NAME/KEY: MOD_RES
<222> LOCATION: (2)..(2)
<223> OTHER INFORMATION: x is bAla
<220> FEATURE:
<221> NAME/KEY: MOD_RES
<222> LOCATION: (5)..(5)
<223> OTHER INFORMATION: x is bAla
<220> FEATURE:
<221> NAME/KEY: MOD_RES
<222> LOCATION: (11)..(11)
<223> OTHER INFORMATION: x is bAla
<220> FEATURE:
<221> NAME/KEY: MOD_RES
<222> LOCATION: (13)..(13)
<223> OTHER INFORMATION: x is bAla

<400> SEQUENCE: 60

Arg Xaa Arg Arg Xaa Arg Trp Pro Trp Trp Xaa Arg Xaa Arg
1               5                   10

<210> SEQ ID NO 61
<211> LENGTH: 14
<212> TYPE: PRT
<213> ORGANISM: Artificial Sequence
<220> FEATURE:
<223> OTHER INFORMATION: peptide
<220> FEATURE:
<221> NAME/KEY: MOD_RES
<222> LOCATION: (2)..(2)
<223> OTHER INFORMATION: x is bAla
<220> FEATURE:
<221> NAME/KEY: MOD_RES
<222> LOCATION: (5)..(5)
<223> OTHER INFORMATION: x is bAla
<220> FEATURE:
<221> NAME/KEY: MOD_RES
<222> LOCATION: (11)..(11)
<223> OTHER INFORMATION: x is bAla
<220> FEATURE:
<221> NAME/KEY: MOD_RES
<222> LOCATION: (13)..(13)
<223> OTHER INFORMATION: x is bAla

<400> SEQUENCE: 61

Arg Xaa Arg Arg Xaa Arg Trp Trp Pro Trp Xaa Arg Xaa Arg
```

```
1               5                   10
```

<210> SEQ ID NO 62
<211> LENGTH: 15
<212> TYPE: PRT
<213> ORGANISM: Artificial Sequence
<220> FEATURE:
<223> OTHER INFORMATION: peptide
<220> FEATURE:
<221> NAME/KEY: MOD_RES
<222> LOCATION: (2)..(2)
<223> OTHER INFORMATION: x is bAla
<220> FEATURE:
<221> NAME/KEY: MOD_RES
<222> LOCATION: (5)..(5)
<223> OTHER INFORMATION: x is bAla
<220> FEATURE:
<221> NAME/KEY: MOD_RES
<222> LOCATION: (12)..(12)
<223> OTHER INFORMATION: x is bAla
<220> FEATURE:
<221> NAME/KEY: MOD_RES
<222> LOCATION: (14)..(14)
<223> OTHER INFORMATION: x is bAla

<400> SEQUENCE: 62

Arg Xaa Arg Arg Xaa Arg Arg Trp Trp Trp Arg Xaa Arg Xaa Arg
1               5                   10                  15

<210> SEQ ID NO 63
<211> LENGTH: 17
<212> TYPE: PRT
<213> ORGANISM: Artificial Sequence
<220> FEATURE:
<223> OTHER INFORMATION: peptide
<220> FEATURE:
<221> NAME/KEY: MOD_RES
<222> LOCATION: (2)..(2)
<223> OTHER INFORMATION: x is bAla
<220> FEATURE:
<221> NAME/KEY: MOD_RES
<222> LOCATION: (5)..(5)
<223> OTHER INFORMATION: x is bAla
<220> FEATURE:
<221> NAME/KEY: MOD_RES
<222> LOCATION: (14)..(14)
<223> OTHER INFORMATION: x is bAla
<220> FEATURE:
<221> NAME/KEY: MOD_RES
<222> LOCATION: (16)..(16)
<223> OTHER INFORMATION: x is bAla

<400> SEQUENCE: 63

Arg Xaa Arg Arg Xaa Arg Arg Trp Trp Pro Trp Arg Xaa Arg Xaa
1               5                   10                  15

Arg

<210> SEQ ID NO 64
<211> LENGTH: 16
<212> TYPE: PRT
<213> ORGANISM: Artificial Sequence
<220> FEATURE:
<223> OTHER INFORMATION: peptide
<220> FEATURE:
<221> NAME/KEY: MOD_RES
<222> LOCATION: (2)..(2)
<223> OTHER INFORMATION: x is bAla
<220> FEATURE:
<221> NAME/KEY: MOD_RES
<222> LOCATION: (5)..(5)
<223> OTHER INFORMATION: x is bAla
<220> FEATURE:
<221> NAME/KEY: MOD_RES -continued

```
<222> LOCATION: (13)..(13)
<223> OTHER INFORMATION: x is bAla
<220> FEATURE:
<221> NAME/KEY: MOD_RES
<222> LOCATION: (15)..(15)
<223> OTHER INFORMATION: x is bAla

<400> SEQUENCE: 64

Arg Xaa Arg Arg Xaa Arg Arg Trp Pro Trp Trp Arg Xaa Arg Xaa Arg
1               5                   10                  15

<210> SEQ ID NO 65
<211> LENGTH: 16
<212> TYPE: PRT
<213> ORGANISM: Artificial Sequence
<220> FEATURE:
<223> OTHER INFORMATION: peptide
<220> FEATURE:
<221> NAME/KEY: MOD_RES
<222> LOCATION: (2)..(2)
<223> OTHER INFORMATION: x is bAla
<220> FEATURE:
<221> NAME/KEY: MOD_RES
<222> LOCATION: (5)..(5)
<223> OTHER INFORMATION: x is bAla
<220> FEATURE:
<221> NAME/KEY: MOD_RES
<222> LOCATION: (13)..(13)
<223> OTHER INFORMATION: x is bAla
<220> FEATURE:
<221> NAME/KEY: MOD_RES
<222> LOCATION: (15)..(15)
<223> OTHER INFORMATION: x is bAla

<400> SEQUENCE: 65

Arg Xaa Arg Arg Xaa Arg Arg Trp Trp Pro Trp Arg Xaa Arg Xaa Arg
1               5                   10                  15

<210> SEQ ID NO 66
<211> LENGTH: 16
<212> TYPE: PRT
<213> ORGANISM: Artificial Sequence
<220> FEATURE:
<223> OTHER INFORMATION: peptide
<220> FEATURE:
<221> NAME/KEY: MOD_RES
<222> LOCATION: (2)..(2)
<223> OTHER INFORMATION: x is bAla
<220> FEATURE:
<221> NAME/KEY: MOD_RES
<222> LOCATION: (5)..(5)
<223> OTHER INFORMATION: x is bAla
<220> FEATURE:
<221> NAME/KEY: MOD_RES
<222> LOCATION: (13)..(13)
<223> OTHER INFORMATION: x is bAla
<220> FEATURE:
<221> NAME/KEY: MOD_RES
<222> LOCATION: (15)..(15)
<223> OTHER INFORMATION: x is bAla

<400> SEQUENCE: 66

Arg Xaa Arg Arg Xaa Arg Arg Phe Gln Ile Leu Tyr Xaa Arg Xaa Arg
1               5                   10                  15

<210> SEQ ID NO 67
<211> LENGTH: 15
<212> TYPE: PRT
<213> ORGANISM: Artificial Sequence
<220> FEATURE:
<223> OTHER INFORMATION: peptide
<220> FEATURE:
<221> NAME/KEY: MOD_RES
```

```
<222> LOCATION: (2)..(2)
<223> OTHER INFORMATION: x is bAla
<220> FEATURE:
<221> NAME/KEY: MOD_RES
<222> LOCATION: (5)..(5)
<223> OTHER INFORMATION: x is bAla
<220> FEATURE:
<221> NAME/KEY: MOD_RES
<222> LOCATION: (14)..(14)
<223> OTHER INFORMATION: x is bAla

<400> SEQUENCE: 67

Arg Xaa Arg Arg Xaa Arg Arg Phe Gln Ile Leu Tyr Arg Xaa Arg
1               5                   10                  15

<210> SEQ ID NO 68
<211> LENGTH: 16
<212> TYPE: PRT
<213> ORGANISM: Artificial Sequence
<220> FEATURE:
<223> OTHER INFORMATION: peptide
<220> FEATURE:
<221> NAME/KEY: MOD_RES
<222> LOCATION: (1)..(1)
<223> OTHER INFORMATION: x is bAla
<220> FEATURE:
<221> NAME/KEY: MOD_RES
<222> LOCATION: (3)..(3)
<223> OTHER INFORMATION: x is bAla
<220> FEATURE:
<221> NAME/KEY: MOD_RES
<222> LOCATION: (5)..(5)
<223> OTHER INFORMATION: x is bAla
<220> FEATURE:
<221> NAME/KEY: MOD_RES
<222> LOCATION: (12)..(12)
<223> OTHER INFORMATION: x is bAla
<220> FEATURE:
<221> NAME/KEY: MOD_RES
<222> LOCATION: (15)..(15)
<223> OTHER INFORMATION: x is bAla

<400> SEQUENCE: 68

Xaa Arg Xaa Arg Xaa Trp Trp Pro Trp Trp Arg Xaa Arg Arg Xaa Arg
1               5                   10                  15

<210> SEQ ID NO 69
<211> LENGTH: 16
<212> TYPE: PRT
<213> ORGANISM: Artificial Sequence
<220> FEATURE:
<223> OTHER INFORMATION: peptide
<220> FEATURE:
<221> NAME/KEY: MOD_RES
<222> LOCATION: (2)..(2)
<223> OTHER INFORMATION: x is bAla
<220> FEATURE:
<221> NAME/KEY: MOD_RES
<222> LOCATION: (5)..(5)
<223> OTHER INFORMATION: x is bAla
<220> FEATURE:
<221> NAME/KEY: MOD_RES
<222> LOCATION: (13)..(13)
<223> OTHER INFORMATION: x is bAla
<220> FEATURE:
<221> NAME/KEY: MOD_RES
<222> LOCATION: (15)..(15)
<223> OTHER INFORMATION: x is bAla

<400> SEQUENCE: 69

Arg Xaa Arg Arg Xaa Arg Arg Phe Gln Ile Leu Tyr Xaa His Xaa His
1               5                   10                  15
```

```
<210> SEQ ID NO 70
<211> LENGTH: 16
<212> TYPE: PRT
<213> ORGANISM: Artificial Sequence
<220> FEATURE:
<223> OTHER INFORMATION: peptide
<220> FEATURE:
<221> NAME/KEY: MOD_RES
<222> LOCATION: (2)..(2)
<223> OTHER INFORMATION: x is bAla
<220> FEATURE:
<221> NAME/KEY: MOD_RES
<222> LOCATION: (5)..(5)
<223> OTHER INFORMATION: x is bAla
<220> FEATURE:
<221> NAME/KEY: MOD_RES
<222> LOCATION: (13)..(13)
<223> OTHER INFORMATION: x is bAla
<220> FEATURE:
<221> NAME/KEY: MOD_RES
<222> LOCATION: (15)..(15)
<223> OTHER INFORMATION: x is bAla

<400> SEQUENCE: 70

Arg Xaa Arg Arg Xaa Arg Arg Phe Gln Ile Tyr Arg Xaa His Xaa His
1               5                   10                  15

<210> SEQ ID NO 71
<211> LENGTH: 15
<212> TYPE: PRT
<213> ORGANISM: Artificial Sequence
<220> FEATURE:
<223> OTHER INFORMATION: peptide
<220> FEATURE:
<221> NAME/KEY: MOD_RES
<222> LOCATION: (2)..(2)
<223> OTHER INFORMATION: x is bAla
<220> FEATURE:
<221> NAME/KEY: MOD_RES
<222> LOCATION: (5)..(5)
<223> OTHER INFORMATION: x is bAla
<220> FEATURE:
<221> NAME/KEY: MOD_RES
<222> LOCATION: (12)..(12)
<223> OTHER INFORMATION: x is bAla
<220> FEATURE:
<221> NAME/KEY: MOD_RES
<222> LOCATION: (14)..(14)
<223> OTHER INFORMATION: x is bAla

<400> SEQUENCE: 71

Arg Xaa Arg Arg Xaa Arg Phe Gln Ile Leu Tyr Xaa Arg Xaa His
1               5                   10                  15

<210> SEQ ID NO 72
<211> LENGTH: 16
<212> TYPE: PRT
<213> ORGANISM: Artificial Sequence
<220> FEATURE:
<223> OTHER INFORMATION: peptide
<220> FEATURE:
<221> NAME/KEY: MOD_RES
<222> LOCATION: (2)..(2)
<223> OTHER INFORMATION: x is bAla
<220> FEATURE:
<221> NAME/KEY: MOD_RES
<222> LOCATION: (5)..(5)
<223> OTHER INFORMATION: x is bAla
<220> FEATURE:
<221> NAME/KEY: MOD_RES
<222> LOCATION: (13)..(13)
<223> OTHER INFORMATION: x is hydroxyproline
<220> FEATURE:
<221> NAME/KEY: MOD_RES
<222> LOCATION: (15)..(15)
```

<223> OTHER INFORMATION: x is hydroxyproline

<400> SEQUENCE: 72

Arg Xaa Arg Arg Xaa Arg Phe Gln Ile Leu Tyr Arg Xaa His Xaa His
1               5                   10                  15

<210> SEQ ID NO 73
<211> LENGTH: 16
<212> TYPE: PRT
<213> ORGANISM: Artificial Sequence
<220> FEATURE:
<223> OTHER INFORMATION: peptide
<220> FEATURE:
<221> NAME/KEY: MOD_RES
<222> LOCATION: (2)..(2)
<223> OTHER INFORMATION: x is hydroxyproline
<220> FEATURE:
<221> NAME/KEY: MOD_RES
<222> LOCATION: (5)..(5)
<223> OTHER INFORMATION: x is hydroxyproline
<220> FEATURE:
<221> NAME/KEY: MOD_RES
<222> LOCATION: (13)..(13)
<223> OTHER INFORMATION: x is bAla
<220> FEATURE:
<221> NAME/KEY: MOD_RES
<222> LOCATION: (15)..(15)
<223> OTHER INFORMATION: x is bAla

<400> SEQUENCE: 73

Arg Xaa Arg Arg Xaa Arg Phe Gln Ile Leu Tyr Arg Xaa His Xaa His
1               5                   10                  15

<210> SEQ ID NO 74
<211> LENGTH: 16
<212> TYPE: PRT
<213> ORGANISM: Artificial Sequence
<220> FEATURE:
<223> OTHER INFORMATION: peptide
<220> FEATURE:
<221> NAME/KEY: MOD_RES
<222> LOCATION: (2)..(2)
<223> OTHER INFORMATION: x is hydroxyproline
<220> FEATURE:
<221> NAME/KEY: MOD_RES
<222> LOCATION: (5)..(5)
<223> OTHER INFORMATION: x is hydroxyproline
<220> FEATURE:
<221> NAME/KEY: MOD_RES
<222> LOCATION: (13)..(13)
<223> OTHER INFORMATION: x is hydroxyproline
<220> FEATURE:
<221> NAME/KEY: MOD_RES
<222> LOCATION: (15)..(15)
<223> OTHER INFORMATION: x is hydroxyproline

<400> SEQUENCE: 74

Arg Xaa Arg Arg Xaa Arg Phe Gln Ile Leu Tyr Arg Xaa His Xaa His
1               5                   10                  15

<210> SEQ ID NO 75
<211> LENGTH: 14
<212> TYPE: PRT
<213> ORGANISM: Artificial Sequence
<220> FEATURE:
<223> OTHER INFORMATION: peptide
<220> FEATURE:
<221> NAME/KEY: MOD_RES
<222> LOCATION: (2)..(2)
<223> OTHER INFORMATION: x is bAla
<220> FEATURE:
<221> NAME/KEY: MOD_RES
<222> LOCATION: (5)..(5)

```
<223> OTHER INFORMATION: x is bAla
<220> FEATURE:
<221> NAME/KEY: MOD_RES
<222> LOCATION: (11)..(11)
<223> OTHER INFORMATION: x is bAla
<220> FEATURE:
<221> NAME/KEY: MOD_RES
<222> LOCATION: (13)..(13)
<223> OTHER INFORMATION: x is bAla

<400> SEQUENCE: 75

Arg Xaa Arg Arg Xaa Arg Trp Trp Trp Arg Xaa His Xaa His
1               5                   10

<210> SEQ ID NO 76
<211> LENGTH: 14
<212> TYPE: PRT
<213> ORGANISM: Artificial Sequence
<220> FEATURE:
<223> OTHER INFORMATION: peptide
<220> FEATURE:
<221> NAME/KEY: MOD_RES
<222> LOCATION: (2)..(2)
<223> OTHER INFORMATION: x is bAla
<220> FEATURE:
<221> NAME/KEY: MOD_RES
<222> LOCATION: (5)..(5)
<223> OTHER INFORMATION: x is bAla
<220> FEATURE:
<221> NAME/KEY: MOD_RES
<222> LOCATION: (11)..(11)
<223> OTHER INFORMATION: x is bAla
<220> FEATURE:
<221> NAME/KEY: MOD_RES
<222> LOCATION: (13)..(13)
<223> OTHER INFORMATION: x is bAla

<400> SEQUENCE: 76

Arg Xaa Arg Arg Xaa Arg Trp Trp Pro Arg Xaa His Xaa His
1               5                   10

<210> SEQ ID NO 77
<211> LENGTH: 14
<212> TYPE: PRT
<213> ORGANISM: Artificial Sequence
<220> FEATURE:
<223> OTHER INFORMATION: peptide
<220> FEATURE:
<221> NAME/KEY: MOD_RES
<222> LOCATION: (2)..(2)
<223> OTHER INFORMATION: x is bAla
<220> FEATURE:
<221> NAME/KEY: MOD_RES
<222> LOCATION: (5)..(5)
<223> OTHER INFORMATION: x is bAla
<220> FEATURE:
<221> NAME/KEY: MOD_RES
<222> LOCATION: (11)..(11)
<223> OTHER INFORMATION: x is bAla
<220> FEATURE:
<221> NAME/KEY: MOD_RES
<222> LOCATION: (13)..(13)
<223> OTHER INFORMATION: x is bAla

<400> SEQUENCE: 77

Arg Xaa Arg Arg Xaa Arg Pro Trp Trp Arg Xaa His Xaa His
1               5                   10

<210> SEQ ID NO 78
<211> LENGTH: 16
<212> TYPE: PRT
<213> ORGANISM: Artificial Sequence
<220> FEATURE:
```

```
<223> OTHER INFORMATION: peptide
<220> FEATURE:
<221> NAME/KEY: MOD_RES
<222> LOCATION: (2)..(2)
<223> OTHER INFORMATION: x is bAla
<220> FEATURE:
<221> NAME/KEY: MOD_RES
<222> LOCATION: (5)..(5)
<223> OTHER INFORMATION: x is bAla
<220> FEATURE:
<221> NAME/KEY: MOD_RES
<222> LOCATION: (13)..(13)
<223> OTHER INFORMATION: x is bAla
<220> FEATURE:
<221> NAME/KEY: MOD_RES
<222> LOCATION: (15)..(15)
<223> OTHER INFORMATION: x is bAla

<400> SEQUENCE: 78

Arg Xaa Arg Arg Xaa Arg Trp Trp Pro Trp Trp Arg Xaa His Xaa His
1               5                   10                  15

<210> SEQ ID NO 79
<211> LENGTH: 15
<212> TYPE: PRT
<213> ORGANISM: Artificial Sequence
<220> FEATURE:
<223> OTHER INFORMATION: peptide
<220> FEATURE:
<221> NAME/KEY: MOD_RES
<222> LOCATION: (2)..(2)
<223> OTHER INFORMATION: x is bAla
<220> FEATURE:
<221> NAME/KEY: MOD_RES
<222> LOCATION: (5)..(5)
<223> OTHER INFORMATION: x is bAla
<220> FEATURE:
<221> NAME/KEY: MOD_RES
<222> LOCATION: (12)..(12)
<223> OTHER INFORMATION: x is bAla
<220> FEATURE:
<221> NAME/KEY: MOD_RES
<222> LOCATION: (14)..(14)
<223> OTHER INFORMATION: x is bAla

<400> SEQUENCE: 79

Arg Xaa Arg Arg Xaa Arg Trp Trp Pro Trp Arg Xaa His Xaa His
1               5                   10                  15

<210> SEQ ID NO 80
<211> LENGTH: 15
<212> TYPE: PRT
<213> ORGANISM: Artificial Sequence
<220> FEATURE:
<223> OTHER INFORMATION: peptide
<220> FEATURE:
<221> NAME/KEY: MOD_RES
<222> LOCATION: (2)..(2)
<223> OTHER INFORMATION: x is bAla
<220> FEATURE:
<221> NAME/KEY: MOD_RES
<222> LOCATION: (5)..(5)
<223> OTHER INFORMATION: x is bAla
<220> FEATURE:
<221> NAME/KEY: MOD_RES
<222> LOCATION: (12)..(12)
<223> OTHER INFORMATION: x is bAla
<220> FEATURE:
<221> NAME/KEY: MOD_RES
<222> LOCATION: (14)..(14)
<223> OTHER INFORMATION: x is bAla

<400> SEQUENCE: 80

Arg Xaa Arg Arg Xaa Arg Trp Pro Trp Trp Arg Xaa His Xaa His
```

```
<210> SEQ ID NO 81
<211> LENGTH: 15
<212> TYPE: PRT
<213> ORGANISM: Artificial Sequence
<220> FEATURE:
<223> OTHER INFORMATION: peptide
<220> FEATURE:
<221> NAME/KEY: MOD_RES
<222> LOCATION: (2)..(2)
<223> OTHER INFORMATION: x is bAla
<220> FEATURE:
<221> NAME/KEY: MOD_RES
<222> LOCATION: (5)..(5)
<223> OTHER INFORMATION: x is bAla
<220> FEATURE:
<221> NAME/KEY: MOD_RES
<222> LOCATION: (12)..(12)
<223> OTHER INFORMATION: x is bAla
<220> FEATURE:
<221> NAME/KEY: MOD_RES
<222> LOCATION: (14)..(14)
<223> OTHER INFORMATION: x is bAla

<400> SEQUENCE: 81

Arg Xaa Arg Arg Xaa Arg Arg Trp Trp Trp Arg Xaa His Xaa His
1               5                   10                  15

<210> SEQ ID NO 82
<211> LENGTH: 17
<212> TYPE: PRT
<213> ORGANISM: Artificial Sequence
<220> FEATURE:
<223> OTHER INFORMATION: peptide
<220> FEATURE:
<221> NAME/KEY: MOD_RES
<222> LOCATION: (2)..(2)
<223> OTHER INFORMATION: x is bAla
<220> FEATURE:
<221> NAME/KEY: MOD_RES
<222> LOCATION: (5)..(5)
<223> OTHER INFORMATION: x is bAla
<220> FEATURE:
<221> NAME/KEY: MOD_RES
<222> LOCATION: (14)..(14)
<223> OTHER INFORMATION: x is bAla
<220> FEATURE:
<221> NAME/KEY: MOD_RES
<222> LOCATION: (16)..(16)
<223> OTHER INFORMATION: x is bAla

<400> SEQUENCE: 82

Arg Xaa Arg Arg Xaa Arg Arg Trp Trp Pro Trp Trp Arg Xaa His Xaa
1               5                   10                  15

His

<210> SEQ ID NO 83
<211> LENGTH: 16
<212> TYPE: PRT
<213> ORGANISM: Artificial Sequence
<220> FEATURE:
<223> OTHER INFORMATION: peptide
<220> FEATURE:
<221> NAME/KEY: MOD_RES
<222> LOCATION: (2)..(2)
<223> OTHER INFORMATION: x is bAla
<220> FEATURE:
<221> NAME/KEY: MOD_RES
<222> LOCATION: (5)..(5)
<223> OTHER INFORMATION: x is bAla
<220> FEATURE:
<221> NAME/KEY: MOD_RES
```

<222> LOCATION: (13)..(13)
<223> OTHER INFORMATION: x is bAla
<220> FEATURE:
<221> NAME/KEY: MOD_RES
<222> LOCATION: (15)..(15)
<223> OTHER INFORMATION: x is bAla

<400> SEQUENCE: 83

Arg Xaa Arg Arg Xaa Arg Arg Trp Pro Trp Trp Arg Xaa His Xaa His
1               5                   10                  15

<210> SEQ ID NO 84
<211> LENGTH: 16
<212> TYPE: PRT
<213> ORGANISM: Artificial Sequence
<220> FEATURE:
<223> OTHER INFORMATION: peptide
<220> FEATURE:
<221> NAME/KEY: MOD_RES
<222> LOCATION: (2)..(2)
<223> OTHER INFORMATION: x is bAla
<220> FEATURE:
<221> NAME/KEY: MOD_RES
<222> LOCATION: (5)..(5)
<223> OTHER INFORMATION: x is bAla
<220> FEATURE:
<221> NAME/KEY: MOD_RES
<222> LOCATION: (13)..(13)
<223> OTHER INFORMATION: x is bAla
<220> FEATURE:
<221> NAME/KEY: MOD_RES
<222> LOCATION: (15)..(15)
<223> OTHER INFORMATION: x is bAla

<400> SEQUENCE: 84

Arg Xaa Arg Arg Xaa Arg Arg Trp Trp Pro Trp Arg Xaa His Xaa His
1               5                   10                  15

<210> SEQ ID NO 85
<211> LENGTH: 17
<212> TYPE: PRT
<213> ORGANISM: Artificial Sequence
<220> FEATURE:
<223> OTHER INFORMATION: peptide
<220> FEATURE:
<221> NAME/KEY: MOD_RES
<222> LOCATION: (3)..(3)
<223> OTHER INFORMATION: x is bAla
<220> FEATURE:
<221> NAME/KEY: MOD_RES
<222> LOCATION: (6)..(6)
<223> OTHER INFORMATION: x is bAla
<220> FEATURE:
<221> NAME/KEY: MOD_RES
<222> LOCATION: (14)..(14)
<223> OTHER INFORMATION: x is bAla
<220> FEATURE:
<221> NAME/KEY: MOD_RES
<222> LOCATION: (16)..(16)
<223> OTHER INFORMATION: x is bAla

<400> SEQUENCE: 85

Arg Arg Xaa Arg Arg Xaa Arg Phe Gln Ile Leu Tyr Arg Xaa His Xaa
1               5                   10                  15

His

<210> SEQ ID NO 86
<211> LENGTH: 16
<212> TYPE: PRT
<213> ORGANISM: Artificial Sequence
<220> FEATURE:
<223> OTHER INFORMATION: peptide

```
<220> FEATURE:
<221> NAME/KEY: MOD_RES
<222> LOCATION: (1)..(1)
<223> OTHER INFORMATION: x is bAla
<220> FEATURE:
<221> NAME/KEY: MOD_RES
<222> LOCATION: (4)..(4)
<223> OTHER INFORMATION: x is bAla
<220> FEATURE:
<221> NAME/KEY: MOD_RES
<222> LOCATION: (13)..(13)
<223> OTHER INFORMATION: x is bAla
<220> FEATURE:
<221> NAME/KEY: MOD_RES
<222> LOCATION: (15)..(15)
<223> OTHER INFORMATION: x is bAla

<400> SEQUENCE: 86

Xaa Arg Arg Xaa Arg Arg Phe Gln Ile Leu Tyr Arg Xaa His Xaa His
1               5                   10                  15

<210> SEQ ID NO 87
<211> LENGTH: 16
<212> TYPE: PRT
<213> ORGANISM: Artificial Sequence
<220> FEATURE:
<223> OTHER INFORMATION: peptide
<220> FEATURE:
<221> NAME/KEY: MOD_RES
<222> LOCATION: (3)..(3)
<223> OTHER INFORMATION: x is bAla
<220> FEATURE:
<221> NAME/KEY: MOD_RES
<222> LOCATION: (6)..(6)
<223> OTHER INFORMATION: x is bAla
<220> FEATURE:
<221> NAME/KEY: MOD_RES
<222> LOCATION: (13)..(13)
<223> OTHER INFORMATION: x is bAla
<220> FEATURE:
<221> NAME/KEY: MOD_RES
<222> LOCATION: (15)..(15)
<223> OTHER INFORMATION: x is bAla

<400> SEQUENCE: 87

Arg Arg Xaa Arg Arg Xaa Arg Phe Gln Ile Leu Tyr Xaa His Xaa His
1               5                   10                  15

<210> SEQ ID NO 88
<211> LENGTH: 15
<212> TYPE: PRT
<213> ORGANISM: Artificial Sequence
<220> FEATURE:
<223> OTHER INFORMATION: peptide
<220> FEATURE:
<221> NAME/KEY: MOD_RES
<222> LOCATION: (1)..(1)
<223> OTHER INFORMATION: x is bAla
<220> FEATURE:
<221> NAME/KEY: MOD_RES
<222> LOCATION: (4)..(4)
<223> OTHER INFORMATION: x is bAla
<220> FEATURE:
<221> NAME/KEY: MOD_RES
<222> LOCATION: (12)..(12)
<223> OTHER INFORMATION: x is bAla
<220> FEATURE:
<221> NAME/KEY: MOD_RES
<222> LOCATION: (14)..(14)
<223> OTHER INFORMATION: x is bAla

<400> SEQUENCE: 88

Xaa Arg Arg Xaa Arg Arg Phe Gln Ile Leu Tyr Xaa His Xaa His
1               5                   10                  15
```

```
<210> SEQ ID NO 89
<211> LENGTH: 17
<212> TYPE: PRT
<213> ORGANISM: Artificial Sequence
<220> FEATURE:
<223> OTHER INFORMATION: peptide
<220> FEATURE:
<221> NAME/KEY: MOD_RES
<222> LOCATION: (2)..(2)
<223> OTHER INFORMATION: x is bAla
<220> FEATURE:
<221> NAME/KEY: MOD_RES
<222> LOCATION: (5)..(5)
<223> OTHER INFORMATION: x is bAla
<220> FEATURE:
<221> NAME/KEY: MOD_RES
<222> LOCATION: (14)..(14)
<223> OTHER INFORMATION: x is bAla
<220> FEATURE:
<221> NAME/KEY: MOD_RES
<222> LOCATION: (16)..(16)
<223> OTHER INFORMATION: x is bAla

<400> SEQUENCE: 89

Arg Xaa Arg Arg Xaa His Arg Phe Gln Ile Leu Tyr Arg Xaa His Xaa
1               5                   10                  15

His

<210> SEQ ID NO 90
<211> LENGTH: 25
<212> TYPE: DNA
<213> ORGANISM: Artificial Sequence
<220> FEATURE:
<223> OTHER INFORMATION: 25-mer PMO antisense sequence for mouse
      dystrophin exon-23

<400> SEQUENCE: 90
ggccaaacct cggcttacct gaaat                                           25

<210> SEQ ID NO 91
<211> LENGTH: 22
<212> TYPE: DNA
<213> ORGANISM: Artificial Sequence
<220> FEATURE:
<223> OTHER INFORMATION: Exon20Fo primer

<400> SEQUENCE: 91
cagaattctg ccaattgctg ag                                              22

<210> SEQ ID NO 92
<211> LENGTH: 20
<212> TYPE: DNA
<213> ORGANISM: Artificial Sequence
<220> FEATURE:
<223> OTHER INFORMATION: Exon26Ro primer

<400> SEQUENCE: 92
ttcttcagct tgtgtcatcc                                                 20

<210> SEQ ID NO 93
<211> LENGTH: 24
<212> TYPE: DNA
<213> ORGANISM: Artificial Sequence
<220> FEATURE:
<223> OTHER INFORMATION: Exon20Fi primer

<400> SEQUENCE: 93
```
cccagtctac caccctatca gagc                                               24

<210> SEQ ID NO 94
<211> LENGTH: 20
<212> TYPE: DNA
<213> ORGANISM: Artificial Sequence
<220> FEATURE:
<223> OTHER INFORMATION: Exon26Ri primer

<400> SEQUENCE: 94
cctgccttta aggcttcctt                                                    20

<210> SEQ ID NO 95
<211> LENGTH: 20
<212> TYPE: DNA
<213> ORGANISM: Artificial Sequence
<220> FEATURE:
<223> OTHER INFORMATION: mDMD23-24 primer 1

<400> SEQUENCE: 95
caggccattc ctctttcagg                                                    20

<210> SEQ ID NO 96
<211> LENGTH: 21
<212> TYPE: DNA
<213> ORGANISM: Artificial Sequence
<220> FEATURE:
<223> OTHER INFORMATION: mDMD23-24 primer 2

<400> SEQUENCE: 96
gaaactttcc tcccagttgg t                                                  21

<210> SEQ ID NO 97
<211> LENGTH: 29
<212> TYPE: DNA
<213> ORGANISM: Artificial Sequence
<220> FEATURE:
<223> OTHER INFORMATION: mDMD23-24 probe
<220> FEATURE:
<221> NAME/KEY: misc_feature
<222> LOCATION: (1)..(1)
<223> OTHER INFORMATION: Labelled with FAM
<220> FEATURE:
<221> NAME/KEY: misc_feature
<222> LOCATION: (9)..(10)
<223> OTHER INFORMATION: Residues no. 9 and no. 10 are linked through an
      internal quencher ZEN
<220> FEATURE:
<221> NAME/KEY: misc_feature
<222> LOCATION: (29)..(29)
<223> OTHER INFORMATION: Labelled with IABkFQ

<400> SEQUENCE: 97
tcaacttcag ccatccattt ctgtaaggt                                          29

<210> SEQ ID NO 98
<211> LENGTH: 30
<212> TYPE: DNA
<213> ORGANISM: Artificial Sequence
<220> FEATURE:
<223> OTHER INFORMATION: mDMD22-24 primer 1

<400> SEQUENCE: 98
ctgaatatga aataatggag gagagactcg                                         30

<210> SEQ ID NO 99
<211> LENGTH: 25
<212> TYPE: DNA

```
<213> ORGANISM: Artificial Sequence
<220> FEATURE:
<223> OTHER INFORMATION: mDMD22-24 primer 2

<400> SEQUENCE: 99
cttcagccat ccatttctgt aaggt                                                25

<210> SEQ ID NO 100
<211> LENGTH: 19
<212> TYPE: DNA
<213> ORGANISM: Artificial Sequence
<220> FEATURE:
<223> OTHER INFORMATION: mDMD22-24 probe
<220> FEATURE:
<221> NAME/KEY: misc_feature
<222> LOCATION: (1)..(1)
<223> OTHER INFORMATION: Labelled with FAM
<220> FEATURE:
<221> NAME/KEY: misc_feature
<222> LOCATION: (9)..(10)
<223> OTHER INFORMATION: residues no. 9 and no. 10 are linked through an
      internal quencher ZEN
<220> FEATURE:
<221> NAME/KEY: misc_feature
<222> LOCATION: (19)..(19)
<223> OTHER INFORMATION: Labelled with IABkFQ

<400> SEQUENCE: 100
atgtgattct gtaatttcc                                                      19

<210> SEQ ID NO 101
<211> LENGTH: 15
<212> TYPE: PRT
<213> ORGANISM: Artificial Sequence
<220> FEATURE:
<223> OTHER INFORMATION: peptide
<220> FEATURE:
<221> NAME/KEY: MISC_FEATURE
<222> LOCATION: (2)..(2)
<223> OTHER INFORMATION: x is bAa
<220> FEATURE:
<221> NAME/KEY: MISC_FEATURE
<222> LOCATION: (5)..(5)
<223> OTHER INFORMATION: x is bAa
<220> FEATURE:
<221> NAME/KEY: MISC_FEATURE
<222> LOCATION: (12)..(12)
<223> OTHER INFORMATION: x is hydroxyproline
<220> FEATURE:
<221> NAME/KEY: MISC_FEATURE
<222> LOCATION: (14)..(14)
<223> OTHER INFORMATION: x is hydroxyproline

<400> SEQUENCE: 101

Arg Xaa Arg Arg Xaa Arg Phe Gln Ile Leu Tyr Xaa Arg Xaa Arg
1               5                   10                  15

<210> SEQ ID NO 102
<211> LENGTH: 15
<212> TYPE: PRT
<213> ORGANISM: Artificial Sequence
<220> FEATURE:
<223> OTHER INFORMATION: peptide
<220> FEATURE:
<221> NAME/KEY: MISC_FEATURE
<222> LOCATION: (2)..(2)
<223> OTHER INFORMATION: x is hydroxyproline
<220> FEATURE:
<221> NAME/KEY: MISC_FEATURE
<222> LOCATION: (5)..(5)
<223> OTHER INFORMATION: x is hydroxyproline
<220> FEATURE:
<221> NAME/KEY: MISC_FEATURE
```

```
<222> LOCATION: (12)..(12)
<223> OTHER INFORMATION: x is bAla
<220> FEATURE:
<221> NAME/KEY: MISC_FEATURE
<222> LOCATION: (14)..(14)
<223> OTHER INFORMATION: x is bAla

<400> SEQUENCE: 102

Arg Xaa Arg Arg Xaa Arg Phe Gln Ile Leu Tyr Xaa Arg Xaa Arg
1               5                   10                  15

<210> SEQ ID NO 103
<211> LENGTH: 15
<212> TYPE: PRT
<213> ORGANISM: Artificial Sequence
<220> FEATURE:
<223> OTHER INFORMATION: peptide
<220> FEATURE:
<221> NAME/KEY: MISC_FEATURE
<222> LOCATION: (2)..(2)
<223> OTHER INFORMATION: x is hydroxyproline
<220> FEATURE:
<221> NAME/KEY: MISC_FEATURE
<222> LOCATION: (5)..(5)
<223> OTHER INFORMATION: x is hydroxyproline
<220> FEATURE:
<221> NAME/KEY: MISC_FEATURE
<222> LOCATION: (12)..(12)
<223> OTHER INFORMATION: x is hydroxyproline
<220> FEATURE:
<221> NAME/KEY: MISC_FEATURE
<222> LOCATION: (14)..(14)
<223> OTHER INFORMATION: x is hydroxyproline

<400> SEQUENCE: 103

Arg Xaa Arg Arg Xaa Arg Phe Gln Ile Leu Tyr Xaa Arg Xaa Arg
1               5                   10                  15

<210> SEQ ID NO 104
<211> LENGTH: 13
<212> TYPE: PRT
<213> ORGANISM: Artificial Sequence
<220> FEATURE:
<223> OTHER INFORMATION: peptide
<220> FEATURE:
<221> NAME/KEY: MISC_FEATURE
<222> LOCATION: (2)..(2)
<223> OTHER INFORMATION: x is bAla
<220> FEATURE:
<221> NAME/KEY: MISC_FEATURE
<222> LOCATION: (5)..(5)
<223> OTHER INFORMATION: x is bAla
<220> FEATURE:
<221> NAME/KEY: MISC_FEATURE
<222> LOCATION: (10)..(10)
<223> OTHER INFORMATION: x is bAla
<220> FEATURE:
<221> NAME/KEY: MISC_FEATURE
<222> LOCATION: (12)..(12)
<223> OTHER INFORMATION: x is bAla

<400> SEQUENCE: 104

Arg Xaa Arg Arg Xaa Arg Trp Trp Trp Xaa Arg Xaa Arg
1               5                   10

<210> SEQ ID NO 105
<211> LENGTH: 15
<212> TYPE: PRT
<213> ORGANISM: Artificial Sequence
<220> FEATURE:
<223> OTHER INFORMATION: peptide
<220> FEATURE:
<221> NAME/KEY: MISC_FEATURE
```

```
<222> LOCATION: (2)..(2)
<223> OTHER INFORMATION: x is bAla
<220> FEATURE:
<221> NAME/KEY: MISC_FEATURE
<222> LOCATION: (5)..(5)
<223> OTHER INFORMATION: x is bAla
<220> FEATURE:
<221> NAME/KEY: MISC_FEATURE
<222> LOCATION: (12)..(12)
<223> OTHER INFORMATION: x is bAla
<220> FEATURE:
<221> NAME/KEY: MISC_FEATURE
<222> LOCATION: (14)..(14)
<223> OTHER INFORMATION: x is bAla

<400> SEQUENCE: 105

Arg Xaa Arg Arg Xaa Arg Trp Trp Pro Trp Trp Xaa Arg Xaa Arg
1               5                   10                  15

<210> SEQ ID NO 106
<211> LENGTH: 11
<212> TYPE: PRT
<213> ORGANISM: Artificial Sequence
<220> FEATURE:
<223> OTHER INFORMATION: peptide
<220> FEATURE:
<221> NAME/KEY: MISC_FEATURE
<222> LOCATION: (2)..(2)
<223> OTHER INFORMATION: x is bAla
<220> FEATURE:
<221> NAME/KEY: MISC_FEATURE
<222> LOCATION: (4)..(4)
<223> OTHER INFORMATION: x is bAla
<220> FEATURE:
<221> NAME/KEY: MISC_FEATURE
<222> LOCATION: (6)..(6)
<223> OTHER INFORMATION: glucosylated serine residue
<220> FEATURE:
<221> NAME/KEY: MISC_FEATURE
<222> LOCATION: (8)..(8)
<223> OTHER INFORMATION: x is bAla
<220> FEATURE:
<221> NAME/KEY: MISC_FEATURE
<222> LOCATION: (10)..(10)
<223> OTHER INFORMATION: x is bAla

<400> SEQUENCE: 106

Arg Xaa Arg Xaa Arg Ser Arg Xaa Arg Xaa Arg
1               5                   10

<210> SEQ ID NO 107
<211> LENGTH: 21
<212> TYPE: DNA
<213> ORGANISM: Artificial Sequence
<220> FEATURE:
<223> OTHER INFORMATION: 21-mer PMO antisense sequence

<400> SEQUENCE: 107
cagcagcagc agcagcagca g                                            21

<210> SEQ ID NO 108
<211> LENGTH: 21
<212> TYPE: DNA
<213> ORGANISM: Artificial Sequence
<220> FEATURE:
<223> OTHER INFORMATION: primer Mbnl1.F

<400> SEQUENCE: 108
gctgcccaat accaggtcaa c                                            21

<210> SEQ ID NO 109
```

```
<211> LENGTH: 22
<212> TYPE: DNA
<213> ORGANISM: Artificial Sequence
<220> FEATURE:
<223> OTHER INFORMATION: primer Mbnl1.R

<400> SEQUENCE: 109
tggtgggaga aatgctgtat gc                                              22

<210> SEQ ID NO 110
<211> LENGTH: 20
<212> TYPE: DNA
<213> ORGANISM: Artificial Sequence
<220> FEATURE:
<223> OTHER INFORMATION: primer DMD.F

<400> SEQUENCE: 110
ttagaggagg tgatggagca                                                 20

<210> SEQ ID NO 111
<211> LENGTH: 20
<212> TYPE: DNA
<213> ORGANISM: Artificial Sequence
<220> FEATURE:
<223> OTHER INFORMATION: primer DMD.R

<400> SEQUENCE: 111
gatactaagg actccatcgc                                                 20

<210> SEQ ID NO 112
<211> LENGTH: 21
<212> TYPE: PRT
<213> ORGANISM: Artificial Sequence
<220> FEATURE:
<223> OTHER INFORMATION: peptide
<220> FEATURE:
<221> NAME/KEY: MISC_FEATURE
<222> LOCATION: (2)..(2)
<223> OTHER INFORMATION: x is aminohexanoic acid
<220> FEATURE:
<221> NAME/KEY: MISC_FEATURE
<222> LOCATION: (5)..(5)
<223> OTHER INFORMATION: x is bAla
<220> FEATURE:
<221> NAME/KEY: MISC_FEATURE
<222> LOCATION: (8)..(8)
<223> OTHER INFORMATION: x is aminohexanoic acid
<220> FEATURE:
<221> NAME/KEY: MISC_FEATURE
<222> LOCATION: (16)..(16)
<223> OTHER INFORMATION: x is aminohexanoic acid
<220> FEATURE:
<221> NAME/KEY: MISC_FEATURE
<222> LOCATION: (18)..(18)
<223> OTHER INFORMATION: x is bAla
<220> FEATURE:
<221> NAME/KEY: MISC_FEATURE
<222> LOCATION: (20)..(20)
<223> OTHER INFORMATION: x is aminohexanoic acid

<400> SEQUENCE: 112

Arg Xaa Arg Arg Xaa Arg Arg Xaa Arg Tyr Gln Phe Leu Ile Arg Xaa
1               5                   10                  15

Arg Xaa Arg Xaa Arg
            20

<210> SEQ ID NO 113
<211> LENGTH: 17
<212> TYPE: PRT
<213> ORGANISM: Artificial Sequence
```

```
<220> FEATURE:
<223> OTHER INFORMATION: peptide
<220> FEATURE:
<221> NAME/KEY: MISC_FEATURE
<222> LOCATION: (2)..(2)
<223> OTHER INFORMATION: x is aminohexanoic acid
<220> FEATURE:
<221> NAME/KEY: MISC_FEATURE
<222> LOCATION: (5)..(5)
<223> OTHER INFORMATION: x is bAla
<220> FEATURE:
<221> NAME/KEY: MISC_FEATURE
<222> LOCATION: (14)..(14)
<223> OTHER INFORMATION: x is bAla
<220> FEATURE:
<221> NAME/KEY: MISC_FEATURE
<222> LOCATION: (16)..(16)
<223> OTHER INFORMATION: x is aminohexanoic acid

<400> SEQUENCE: 113

Arg Xaa Arg Arg Xaa Arg Arg Phe Gln Ile Leu Tyr Arg Xaa Arg Xaa
1               5                   10                  15

Arg

<210> SEQ ID NO 114
<211> LENGTH: 6
<212> TYPE: PRT
<213> ORGANISM: Artificial Sequence
<220> FEATURE:
<223> OTHER INFORMATION: peptide

<400> SEQUENCE: 114

Arg Arg Arg Arg Arg Arg
1               5

<210> SEQ ID NO 115
<211> LENGTH: 7
<212> TYPE: PRT
<213> ORGANISM: Artificial Sequence
<220> FEATURE:
<223> OTHER INFORMATION: synthetic construct

<400> SEQUENCE: 115

Arg Arg Arg Arg Arg Arg Gly
1               5
```